US012291710B2

(12) United States Patent
Kawano et al.

(10) Patent No.: US 12,291,710 B2
(45) Date of Patent: May 6, 2025

(54) ANTISENSE OLIGONUCLEOTIDE TARGETING ATN1 mRNA OR PRE-mRNA

(71) Applicants: NIPPON SHINYAKU CO., LTD., Kyoto (JP); NIIGATA UNIVERSITY, Niigata (JP)

(72) Inventors: Takao Kawano, Kyoto (JP); Toshiaki Ode, Kyoto (JP); Akie Chiba, Ibaraki (JP); Osamu Onodera, Niigata (JP); Taisuke Kato, Niigata (JP); Sachiko Hirokawa, Niigata (JP)

(73) Assignees: Nippon Shinyaku Co., Ltd., Kyoto (JP); Niigata University, Niigata (JP)

( * ) Notice: Subject to any disclaimer, the term of this patent is extended or adjusted under 35 U.S.C. 154(b) by 0 days.

(21) Appl. No.: 18/741,110

(22) Filed: Jun. 12, 2024

(65) Prior Publication Data

US 2024/0318181 A1 Sep. 26, 2024

Related U.S. Application Data

(63) Continuation of application No. PCT/JP2022/045921, filed on Dec. 13, 2022.

(30) Foreign Application Priority Data

Dec. 13, 2021 (JP) ................................ 2021-201756
Nov. 18, 2022 (JP) ................................ 2022-184853

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/11* (2013.01); *C12N 2310/315* (2013.01); *C12N 2310/321* (2013.01); *C12N 2310/341* (2013.01); *C12N 2310/3525* (2013.01)

(58) Field of Classification Search
CPC ............. C12N 15/113; C12N 2310/11; C12N 2310/315; C12N 2310/321; C12N 2310/341; C12N 2310/3525; A61P 25/28; A61P 25/00; A61P 25/08; A61P 25/14; C07K 14/47; A61K 31/7088; A61K 31/712; A61K 31/7125; A61K 48/00
See application file for complete search history.

(56) References Cited

U.S. PATENT DOCUMENTS

2013/0198877 A1 8/2013 Van Roon-Mom et al.
2021/0054377 A1 2/2021 Masaki et al.
2023/0127437 A1 4/2023 Hashimoto et al.

FOREIGN PATENT DOCUMENTS

CA 3169474 A1 * 8/2021 ............. A61P 25/00
WO WO-2019/182037 A1 9/2019
WO WO-2021/153747 A1 8/2021
WO WO-2022/211129 A1 10/2022
WO WO-2023/164656 A2 8/2023
WO WO-2023/201281 A2 10/2023

OTHER PUBLICATIONS

Nowak (et al. 2023. Atrophin-1 Function and Dysfunction in Dentatorubral-Pallidoluysian Atrophy. Movement Disorders 38[4]:526-536) (Year: 2023).*
Tenchov (et al. 2024. Polyglutamine [PolyQ] Diseases: Navigating the Landscape of Neurodegeneration. ACS Chem. Neurosci. 15:2665-2694) (Year: 2024).*
Fujita et al, "Attempts to Treat DRPLA Model Mice with Antisense Oligonucleotides (Poster)," The 38th Annual Meeting of the Japan Neuroscience Society, Jul. 29, 2015, Kobe International Exhibition Hall (Year: 2015).*
Evers et al., "Targeting Several CAG Expansion Diseases by a Single Antisense Oligonucleotide," PLoS One, Sep. 2011, 6(9):e24308, 1-11.
Hu et al., "Allele-Selective Inhibition of Mutant Atrophin-1 Expression by Duplex and Single-Stranded RNAs," Biochemistry, Jul. 1, 2014, 53(28):4510-4518.
Onodera, Osamu, "Search for Candidates for polyglutamine disease using In vitro disease model system," Entrusted labor science research project, May 13, 2016, with English machine translation.
Scholefield et al., "Therapeutic gene silencing strategies for polyglutamine disorders," Trends in Genetics, Jan. 2010 (online Dec. 3, 2009), 26(1):29-38.
Veneziano et al., Gene Reviews [Internet], Aug. 6, 1999 (updated Jun. 6, 2016, 1993-2021, 1-17.

* cited by examiner

*Primary Examiner* — Nancy J Leith
*Assistant Examiner* — Ruth Sophia Arieti
(74) *Attorney, Agent, or Firm* — Foley & Lardner LLP

(57) ABSTRACT

The present invention provides an antisense oligonucleotide that is formed of 15-22 nucleotides and that is complementary to a nucleic acid including at least 15 consecutive bases in a specific target region of a base sequence of SEQ ID NO: 471 (which encodes atrophin 1; ATN1), or a pharmaceutically acceptable salt thereof, or a hydrate thereof.

18 Claims, No Drawings

Specification includes a Sequence Listing.

ANTISENSE OLIGONUCLEOTIDE TARGETING ATN1 mRNA OR PRE-mRNA

CROSS-REFERENCE TO RELATED APPLICATIONS

This application is a Continuation of PCT/JP2022/045921, filed Dec. 13, 2022, which claims priority to JP 2021-201756, filed Dec. 13, 2021 and JP 2022-184853, filed Nov. 18, 2022, the entire contents of which are incorporated herein by reference.

The instant application contains a Sequence Listing which has been submitted in XML format and is hereby incorporated by reference in its entirety. Said XML copy, created on Jun. 11, 2024, is named G2861WOsequencelisting.xml and is 598,487 bytes.

TECHNICAL FIELD

The present invention relates to an antisense oligonucleotide targeting an ATN1 mRNA or pre-mRNA, or a pharmaceutically acceptable salt thereof, or a hydrate thereof, and a pharmaceutical composition or the like comprising the antisense oligonucleotide or a pharmaceutically acceptable salt thereof, or a hydrate thereof.

BACKGROUND ART

Dentatorubral-pallidoluysian atrophy (DRPLA) is a progressive disease that causes ataxia, involuntary movement designated as myoclonus, epilepsy, progressive intellectual deterioration and the like in a child patient, and causes ataxia, choreoathetosis, dementia, personality change or the like in an adult patient (Non Patent Literature 1).

DRPLA is a disease (repeat disease) caused due to RNA or protein functional abnormality caused by abnormal elongation of a repeat sequence present in the genome of a specific gene. DRPLA is known, among repeat diseases, as a disease in which a protein exhibits toxicity. DRPLA is divided into adult-onset type that develops at the age of 20 or older, and childhood-onset type that develops at the age younger than 20 depending on the time of onset, and early developing childhood-onset type is caused and the degree of seriousness is high in a patient having the number of repeats of about 65 or more.

Currently, although there are some symptomatic drugs for some of the symptoms of DRPLA, that is, epilepsy, a psychiatric symptom, ataxia, and the like, treatment satisfaction of these is low, and it is impossible to cope with molecular mechanism underlying DRPLA.

CITATION LIST

Non Patent Literature

Non Patent Literature 1: Liana Veneziano et al., Gene Reviews [Internet] 1999 Aug. 6 [updated 2016 Jun. 9], 1993-2021

SUMMARY OF INVENTION

Under these circumstances, it is desired to provide a DRPLA therapeutic agent exhibiting more excellent therapeutic effects.

The present invention provides an antisense oligonucleotide targeting an ATN1 mRNA or pre-mRNA, or a pharmaceutically acceptable salt thereof, or a hydrate thereof, and a pharmaceutical composition or the like comprising the antisense oligonucleotide, or a pharmaceutically acceptable salt thereof, or a hydrate thereof as follows.

(1-1) An antisense oligonucleotide consisting of 15 to 22 nucleotides complementary to a nucleic acid comprising at least 15 consecutive bases in a target region selected from the group consisting of positions 1 to 84, 142 to 168, 197 to 224, 286 to 317, 324 to 370, 391 to 434, 519 to 540, 623 to 643, 690 to 780, 824 to 855, 860 to 897, 948 to 987, 1044 to 1072, 1125 to 1174, 1181 to 1213, 1228 to 1255, 1265 to 1327, 1334 to 1356, 1416 to 1440, 1447 to 1631, 1638 to 1667, 1675 to 1705, 1748 to 1823, 1838 to 1861, 1870 to 1913, 1920 to 1941, 2000 to 2040, 2047 to 2075, 2086 to 2120, 2129 to 2187, 2194 to 2415, 2451 to 2497, 2592 to 2759, 2766 to 2870, 2928 to 2948, 2955 to 2989, 3021 to 3086, 3133 to 3209, 3217 to 3284, 3295 to 3350, 3384 to 3436, 3562 to 3771, 3858 to 3905, 3931 to 4039, 4067 to 4134, 4170 to 4232, 4241 to 4283, and 4286 to 4355 of a base sequence of SEQ ID NO: 471, or a pharmaceutically acceptable salt thereof, or a hydrate thereof.

(1-2) The antisense oligonucleotide, or a pharmaceutically acceptable salt thereof, or a hydrate thereof according to (1-1), wherein the antisense oligonucleotide is complementary to a nucleic acid comprising at least 15 consecutive bases in a target region selected from the group consisting of positions 1 to 84, 142 to 168, 391 to 434, 697 to 780, 962 to 980, 1125 to 1174, 1181 to 1213, 1228 to 1255, 1265 to 1320, 1454 to 1631, 1682 to 1705, 1748 to 1816, 1870 to 1913, 2015 to 2040, 2086 to 2120, 2129 to 2187, 2201 to 2408, 2592 to 2759, 2773 to 2870, 2955 to 2982, 3028 to 3079, 3133 to 3209, 3224 to 3277, 3295 to 3350, 3391 to 3429, 3562 to 3771, 3865 to 3898, 3938 to 4032, 4074 to 4127, and 4170 to 4225 of the base sequence of SEQ ID NO: 471.

(2-1) The antisense oligonucleotide or a pharmaceutically acceptable salt thereof, or a hydrate thereof according to (1-1), wherein the antisense oligonucleotide is complementary to a nucleic acid comprising at least 15 consecutive bases in a target region selected from the group consisting of positions 1 to 69, 331 to 363, 398 to 427, 697 to 773, 867 to 890, 955 to 980, 1132 to 1167, 1272 to 1320, 1454 to 1624, 1682 to 1705, 1748 to 1816, 1877 to 1906, 2007 to 2033, 2093 to 2113, 2136 to 2180, 2201 to 2408, 2458 to 2490, 2599 to 2752, 2773 to 2863, 2962 to 2982, 3028 to 3079, 3140 to 3202, 3224 to 3277, 3302 to 3343, 3391 to 3429, 3569 to 3764, 3865 to 3898, 3938 to 4032, 4074 to 4127, 4177 to 4225, 4248 to 4276, and 4293 to 4355 of the base sequence of SEQ ID NO: 471.

(2-2) The antisense oligonucleotide, or a pharmaceutically acceptable salt thereof, or a hydrate thereof according to (1-1), wherein the antisense oligonucleotide is complementary to a nucleic acid comprising at least 15 consecutive bases in a target region selected from the group consisting of positions 1 to 69, 398 to 427, 697 to 773, 1132 to 1167, 1272 to 1320, 1454 to 1624, 1682 to 1705, 1748 to 1816, 1877 to 1906, 2093 to 2113, 2136 to 2180, 2201 to 2408, 2599 to 2752, 2773 to 2863, 2962 to 2982, 3028 to 3079, 3140 to 3202, 3224 to 3277, 3302 to 3343, 3391 to 3429, 3569 to 3764, 3865 to 3898, 3938 to 4032, and 4177 to 4225 of the base sequence of SEQ ID NO: 471.

(3) The antisense oligonucleotide or a pharmaceutically acceptable salt thereof, or a hydrate thereof according to (1-1), wherein the antisense oligonucleotide is complementary to a nucleic acid comprising at least 15 consecutive bases in a target region selected from the group consisting of positions 14 to 33, 34 to 53, 54 to 73, 148 to 167, 397 to 432, 723 to 742, 747 to 778, 965 to 984, 1127 to 1146, 1148 to 1173, 1182 to 1213, 1228 to 1254, 1270 to 1308, 1484 to 1564, 1578 to 1629, 1686 to 1705, 1748 to 1767, 1768 to 1787, 1794 to 1813, 1870 to 1913, 2015 to 2034, 2086 to 2118, 2129 to 2148, 2151 to 2184, 2206 to 2225, 2239 to 2272, 2287 to 2336, 2337 to 2373, 2387 to 2406, 2598 to 2757, 2775 to 2809, 2826 to 2866, 2959 to 2982, 3032 to 3051, 3052 to 3071, 3136 to 3155, 3168 to 3187, 3188 to 3207, 3232 to 3270, 3298 to 3344, 3408 to 3427, 3563 to 3582, 3590 to 3728, 3739 to 3769, 3877 to 3896, 3949 to 4030, and 4170 to 4225 of the base sequence of SEQ ID NO: 471.

(4) The antisense oligonucleotide or a pharmaceutically acceptable salt thereof, or a hydrate thereof according to (3), wherein the antisense oligonucleotide is complementary to a nucleic acid comprising at least 15 consecutive bases in a target region selected from the group consisting of positions 14 to 33, 34 to 53, 54 to 73, 148 to 167, 397 to 416, 398 to 417, 399 to 418, 400 to 419, 401 to 420, 402 to 421, 403 to 422, 404 to 423, 405 to 424, 406 to 425, 407 to 426, 408 to 427, 413 to 432, 723 to 742, 747 to 766, 756 to 775, 759 to 778, 965 to 984, 1127 to 1146, 1148 to 1167, 1151 to 1170, 1154 to 1173, 1182 to 1201, 1185 to 1204, 1188 to 1207, 1191 to 1210, 1194 to 1213, 1228 to 1247, 1231 to 1250, 1235 to 1254, 1270 to 1289, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1579 to 1598, 1580 to 1599, 1581 to 1600, 1582 to 1601, 1583 to 1602, 1584 to 1603, 1585 to 1604, 1586 to 1605, 1587 to 1606, 1588 to 1607, 1589 to 1608, 1590 to 1609, 1591 to 1610, 1592 to 1611, 1593 to 1612, 1594 to 1613, 1595 to 1614, 1596 to 1615, 1597 to 1616, 1598 to 1617, 1599 to 1618, 1600 to 1619, 1601 to 1620, 1602 to 1621, 1603 to 1622, 1604 to 1623, 1605 to 1624, 1607 to 1626, 1610 to 1629, 1686 to 1705, 1748 to 1767, 1768 to 1787, 1794 to 1813, 1870 to 1889, 1871 to 1890, 1874 to 1893, 1877 to 1896, 1878 to 1897, 1879 to 1898, 1880 to 1899, 1881 to 1900, 1882 to 1901, 1883 to 1902, 1884 to 1903, 1885 to 1904, 1886 to 1905, 1887 to 1906, 1889 to 1908, 1894 to 1913, 2015 to 2034, 2086 to 2105, 2093 to 2112, 2094 to 2113, 2097 to 2116, 2099 to 2118, 2129 to 2148, 2151 to 2170, 2165 to 2184, 2206 to 2225, 2239 to 2258, 2253 to 2272, 2287 to 2306, 2301 to 2320, 2317 to 2336, 2337 to 2356, 2354 to 2373, 2387 to 2406, 2598 to 2617, 2613 to 2632, 2614 to 2633, 2615 to 2634, 2616 to 2635, 2617 to 2636, 2618 to 2637, 2619 to 2638, 2620 to 2639, 2621 to 2640, 2622 to 2641, 2623 to 2642, 2624 to 2643, 2625 to 2644, 2626 to 2645, 2627 to 2646, 2628 to 2647, 2629 to 2648, 2630 to 2649, 2631 to 2650, 2632 to 2651, 2633 to 2652, 2634 to 2653, 2635 to 2654, 2636 to 2655, 2637 to 2656, 2638 to 2657, 2639 to 2658, 2640 to 2659, 2641 to 2660, 2642 to 2661, 2643 to 2662, 2644 to 2663, 2645 to 2664, 2646 to 2665, 2647 to 2666, 2648 to 2667, 2649 to 2668, 2663 to 2682, 2672 to 2691, 2673 to 2692, 2674 to 2693, 2675 to 2694, 2676 to 2695, 2677 to 2696, 2678 to 2697, 2679 to 2698, 2680 to 2699, 2681 to 2700, 2682 to 2701, 2683 to 2702, 2684 to 2703, 2685 to 2704, 2686 to 2705, 2687 to 2706, 2688 to 2707, 2689 to 2708, 2690 to 2709, 2691 to 2710, 2692 to 2711, 2693 to 2712, 2694 to 2713, 2695 to 2714, 2696 to 2715, 2697 to 2716, 2698 to 2717, 2699 to 2718, 2700 to 2719, 2701 to 2720, 2702 to 2721, 2703 to 2722, 2704 to 2723, 2705 to 2724, 2706 to 2725, 2707 to 2726, 2708 to 2727, 2709 to 2728, 2710 to 2729, 2711 to 2730, 2712 to 2731, 2713 to 2732, 2714 to 2733, 2715 to 2734, 2716 to 2735, 2717 to 2736, 2718 to 2737, 2719 to 2738, 2720 to 2739, 2721 to 2740, 2722 to 2741, 2723 to 2742, 2724 to 2743, 2725 to 2744, 2726 to 2745, 2727 to 2746, 2728 to 2747, 2729 to 2748, 2730 to 2749, 2731 to 2750, 2732 to 2751, 2733 to 2752, 2738 to 2757, 2775 to 2794, 2790 to 2809, 2826 to 2845, 2827 to 2846, 2828 to 2847, 2829 to 2848, 2830 to 2849, 2831 to 2850, 2832 to 2851, 2833 to 2852, 2834 to 2853, 2835 to 2854, 2836 to 2855, 2837 to 2856, 2838 to 2857, 2839 to 2858, 2840 to 2859, 2841 to 2860, 2842 to 2861, 2843 to 2862, 2844 to 2863, 2847 to 2866, 2959 to 2978, 2962 to 2981, 2963 to 2982, 3032 to 3051, 3052 to 3071, 3136 to 3155, 3168 to 3187, 3188 to 3207, 3232 to 3251, 3251 to 3270, 3298 to 3317, 3302 to 3321, 3303 to 3322, 3304 to 3323, 3305 to 3324, 3306 to 3325, 3307 to 3326, 3308 to 3327, 3309 to 3328, 3310 to 3329, 3311 to 3330, 3312 to 3331, 3313 to 3332, 3314 to 3333, 3315 to 3334, 3316 to 3335, 3317 to 3336, 3318 to 3337, 3319 to 3338, 3320 to 3339, 3321 to 3340, 3322 to 3341, 3323 to 3342, 3324 to 3343, 3325 to 3344, 3408 to 3427, 3563 to 3582, 3590 to 3609, 3608 to 3627, 3617 to 3636, 3618 to 3637, 3619 to 3638, 3620 to 3639, 3621 to 3640, 3622 to 3641, 3623 to 3642, 3624 to 3643, 3625 to 3644, 3626 to 3645, 3627 to 3646, 3628 to 3647, 3629 to 3648, 3630 to 3649, 3631 to 3650, 3632 to 3651, 3633 to 3652, 3634 to 3653, 3635 to 3654, 3636 to 3655, 3637 to 3656, 3638 to 3657, 3639 to 3658, 3640 to 3659, 3641 to 3660, 3642 to 3661, 3643 to 3662, 3644 to 3663, 3645 to 3664, 3646 to 3665, 3647 to 3666, 3648 to 3667, 3649 to 3668, 3650 to 3669, 3651 to 3670, 3652 to 3671, 3653 to 3672, 3654 to 3673, 3671 to 3690, 3672 to 3691, 3673 to 3692, 3674 to 3693, 3675 to 3694, 3676 to 3695, 3677 to 3696, 3678 to 3697, 3679 to 3698, 3680 to 3699, 3681 to 3700, 3682 to 3701, 3683 to 3702, 3684 to 3703, 3685 to 3704, 3686 to 3705, 3687 to 3706, 3688 to 3707, 3689 to 3708, 3690 to 3709, 3691 to 3710, 3692 to 3711, 3693 to 3712, 3694 to 3713, 3695 to 3714, 3696 to 3715, 3697 to 3716, 3698 to 3717, 3699 to 3718, 3700 to 3719, 3701 to 3720, 3702 to 3721, 3703 to 3722, 3704 to 3723, 3705 to 3724, 3706 to 3725, 3707 to 3726, 3708 to 3727, 3709 to 3728, 3739 to 3758, 3740 to 3759, 3741 to 3760, 3742 to 3761, 3743 to 3762, 3744 to 3763, 3745 to 3764, 3750 to 3769, 3877 to 3896, 3949 to 3968, 3964 to 3983, 3965 to 3984, 3966 to 3985, 3967 to 3986, 3968 to 3987, 3969 to 3988, 3970 to 3989, 3971 to 3990, 3972 to 3991, 3973 to 3992, 3974 to 3993, 3975 to 3994, 3976 to 3995, 3977 to 3996, 3978 to 3997, 3979 to 3998, 3980 to 3999, 3981 to 4000, 3982 to 4001, 3983 to 4002, 3984 to 4003, 3985 to 4004, 3986 to 4005, 3987 to 4006, 3988 to 4007, 3989 to 4008, 3990 to 4009, 3991 to 4010, 3992 to 4011, 3993 to 4012, 3994 to 4013, 3995 to 4014, 3996 to 4015, 3997 to 4016, 3998 to 4017, 3999 to 4018, 4011 to 4030, 4170 to 4189, 4173 to 4192, 4176 to 4195, 4177 to 4196, 4178 to 4197, 4179 to 4198, 4180 to 4199, 4181 to 4200, 4182 to 4201, 4183 to 4202, 4184 to 4203, 4185 to 4204, 4186 to 4205, 4187 to 4206, 4188 to 4207, 4189 to 4208, 4190 to 4209, 4191 to 4210, 4192 to 4211, 4193 to 4212, 4194 to 4213, 4195 to 4214, 4196 to 4215, 4197 to 4216, 4198 to 4217, 4199 to 4218, 4200 to 4219, 4201 to 4220, 4202 to 4221, 4203 to 4222, 4204 to 4223, 4205 to 4224, and 4206 to 4225 of the base sequence of SEQ ID NO: 471.

(5) The antisense oligonucleotide or a pharmaceutically acceptable salt thereof, or a hydrate thereof according to (2-1) or (3), wherein the antisense oligonucleotide is complementary to a nucleic acid comprising at least 15 consecutive bases in a target region selected from the group consisting of positions 14 to 33, 34 to 53, 398 to 427, 723 to 742, 747 to 766, 1148 to 1167, 1289 to 1308, 1484 to 1564, 1578 to 1624, 1686 to 1705, 1748 to 1767, 1768 to 1787, 1794 to 1813, 1877 to 1906, 2093 to 2113, 2151 to 2170, 2206 to 2225, 2239 to 2272, 2287 to 2336, 2337 to 2373, 2387 to 2406, 2613 to 2752, 2775 to 2809, 2826 to 2863, 2962 to 2982, 3032 to 3051, 3052 to 3071, 3168 to 3187, 3232 to 3270, 3302 to 3343, 3408 to 3427, 3590 to 3728, 3739 to 3764, 3877 to 3896, 3949 to 4030, and 4177 to 4225 of the base sequence of SEQ ID NO: 471.

(6) The antisense oligonucleotide or a pharmaceutically acceptable salt thereof, or a hydrate thereof according to (5), wherein the antisense oligonucleotide is complementary to a nucleic acid comprising at least 15 consecutive bases in a target region selected from the group consisting of positions 14 to 33, 34 to 53, 398 to 417, 399 to 418, 400 to 419, 401 to 420, 402 to 421, 403 to 422, 404 to 423, 405 to 424, 406 to 425, 407 to 426, 408 to 427, 723 to 742, 747 to 766, 1148 to 1167, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1579 to 1598, 1580 to 1599, 1581 to 1600, 1582 to 1601, 1583 to 1602, 1584 to 1603, 1585 to 1604, 1586 to 1605, 1587 to 1606, 1588 to 1607, 1589 to 1608, 1590 to 1609, 1591 to 1610, 1592 to 1611, 1593 to 1612, 1594 to 1613, 1595 to 1614, 1596 to 1615, 1597 to 1616, 1598 to 1617, 1599 to 1618, 1600 to 1619, 1601 to 1620, 1602 to 1621, 1603 to 1622, 1604 to 1623, 1605 to 1624, 1686 to 1705, 1748 to 1767, 1768 to 1787, 1794 to 1813, 1877 to 1896, 1878 to 1897, 1879 to 1898, 1880 to 1899, 1881 to 1900, 1882 to 1901, 1883 to 1902, 1884 to 1903, 1885 to 1904, 1886 to 1905, 1887 to 1906, 2093 to 2112, 2094 to 2113, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2613 to 2632, 2614 to 2633, 2615 to 2634, 2616 to 2635, 2617 to 2636, 2618 to 2637, 2619 to 2638, 2620 to 2639, 2621 to 2640, 2622 to 2641, 2623 to 2642, 2624 to 2643, 2625 to 2644, 2626 to 2645, 2627 to 2646, 2628 to 2647, 2629 to 2648, 2630 to 2649, 2631 to 2650, 2632 to 2651, 2633 to 2652, 2634 to 2653, 2635 to 2654, 2636 to 2655, 2637 to 2656, 2638 to 2657, 2639 to 2658, 2640 to 2659, 2641 to 2660, 2642 to 2661, 2643 to 2662, 2644 to 2663, 2645 to 2664, 2646 to 2665, 2647 to 2666, 2648 to 2667, 2649 to 2668, 2663 to 2682, 2672 to 2691, 2673 to 2692, 2674 to 2693, 2675 to 2694, 2676 to 2695, 2677 to 2696, 2678 to 2697, 2679 to 2698, 2680 to 2699, 2681 to 2700, 2682 to 2701, 2683 to 2702, 2684 to 2703, 2685 to 2704, 2686 to 2705, 2687 to 2706, 2688 to 2707, 2689 to 2708, 2690 to 2709, 2691 to 2710, 2692 to 2711, 2693 to 2712, 2694 to 2713, 2695 to 2714, 2696 to 2715, 2697 to 2716, 2698 to 2717, 2699 to 2718, 2700 to 2719, 2701 to 2720, 2702 to 2721, 2703 to 2722, 2704 to 2723, 2705 to 2724, 2706 to 2725, 2707 to 2726, 2708 to 2727, 2709 to 2728, 2710 to 2729, 2711 to 2730, 2712 to 2731, 2713 to 2732, 2714 to 2733, 2715 to 2734, 2716 to 2735, 2717 to 2736, 2718 to 2737, 2719 to 2738, 2720 to 2739, 2721 to 2740, 2722 to 2741, 2723 to 2742, 2724 to 2743, 2725 to 2744, 2726 to 2745, 2727 to 2746, 2728 to 2747, 2729 to 2748, 2730 to 2749, 2731 to 2750, 2732 to 2751, 2733 to 2752, 2775 to 2794, 2790 to 2809, 2826 to 2845, 2827 to 2846, 2828 to 2847, 2829 to 2848, 2830 to 2849, 2831 to 2850, 2832 to 2851, 2833 to 2852, 2834 to 2853, 2835 to 2854, 2836 to 2855, 2837 to 2856, 2838 to 2857, 2839 to 2858, 2840 to 2859, 2841 to 2860, 2842 to 2861, 2843 to 2862, 2844 to 2863, 2962 to 2981, 2963 to 2982, 3032 to 3051, 3052 to 3071, 3168 to 3187, 3232 to 3251, 3251 to 3270, 3302 to 3321, 3303 to 3322, 3304 to 3323, 3305 to 3324, 3306 to 3325, 3307 to 3326, 3308 to 3327, 3309 to 3328, 3310 to 3329, 3311 to 3330, 3312 to 3331, 3313 to 3332, 3314 to 3333, 3315 to 3334, 3316 to 3335, 3317 to 3336, 3318 to 3337, 3319 to 3338, 3320 to 3339, 3321 to 3340, 3322 to 3341, 3323 to 3342, 3324 to 3343, 3408 to 3427, 3590 to 3609, 3608 to 3627, 3617 to 3636, 3618 to 3637, 3619 to 3638, 3620 to 3639, 3621 to 3640, 3622 to 3641, 3623 to 3642, 3624 to 3643, 3625 to 3644, 3626 to 3645, 3627 to 3646, 3628 to 3647, 3629 to 3648, 3630 to 3649, 3631 to 3650, 3632 to 3651, 3633 to 3652, 3634 to 3653, 3635 to 3654, 3636 to 3655, 3637 to 3656, 3638 to 3657, 3639 to 3658, 3640 to 3659, 3641 to 3660, 3642 to 3661, 3643 to 3662, 3644 to 3663, 3645 to 3664, 3646 to 3665, 3647 to 3666, 3648 to 3667, 3649 to 3668, 3650 to 3669, 3651 to 3670, 3652 to 3671, 3653 to 3672, 3654 to 3673, 3671 to 3690, 3672 to 3691, 3673 to 3692, 3674 to 3693, 3675 to 3694, 3676 to 3695, 3677 to 3696, 3678 to 3697, 3679 to 3698, 3680 to 3699, 3681 to 3700, 3682 to 3701, 3683 to 3702, 3684 to 3703, 3685 to 3704, 3686 to 3705, 3687 to 3706, 3688 to 3707, 3689 to 3708, 3690 to 3709, 3691 to 3710, 3692 to 3711, 3693 to 3712, 3694 to 3713, 3695 to 3714, 3696 to 3715, 3697 to 3716, 3698 to 3717, 3699 to 3718, 3700 to 3719, 3701 to 3720, 3702 to 3721, 3703 to 3722, 3704 to 3723, 3705 to 3724, 3706 to 3725, 3707 to 3726, 3708 to 3727, 3709 to 3728, 3739 to 3758, 3740 to 3759, 3741 to 3760, 3742 to 3761, 3743 to 3762, 3744 to 3763, 3745 to 3764, 3877 to 3896, 3949 to 3968, 3964 to 3983, 3965 to 3984, 3966 to 3985, 3967 to 3986, 3968 to 3987, 3969 to 3988, 3970 to 3989, 3971 to 3990, 3972 to 3991, 3973 to 3992, 3974 to 3993, 3975 to 3994, 3976 to 3995, 3977 to 3996, 3978 to 3997, 3979 to 3998, 3980 to 3999, 3981 to 4000, 3982 to 4001, 3983 to 4002, 3984 to 4003, 3985 to 4004, 3986 to 4005, 3987 to 4006, 3988 to 4007, 3989 to 4008, 3990 to 4009, 3991 to 4010, 3992 to 4011, 3993 to 4012, 3994 to 4013, 3995 to 4014, 3996 to 4015, 3997 to 4016, 3998 to 4017, 3999 to 4018, 4011 to 4030, 4177 to 4196, 4178 to 4197, 4179 to 4198, 4180 to 4199, 4181 to 4200, 4182 to 4201, 4183 to 4202, 4184 to 4203, 4185 to 4204, 4186 to 4205, 4187 to 4206, 4188 to 4207, 4189 to 4208, 4190 to 4209, 4191 to 4210, 4192 to 4211, 4193 to 4212, 4194 to 4213, 4195 to 4214, 4196 to 4215, 4197 to 4216, 4198 to 4217, 4199 to 4218, 4200 to 4219, 4201 to 4220, 4202 to 4221, 4203 to 4222, 4204 to 4223, 4205 to 4224, and 4206 to 4225 of the base sequence of SEQ ID NO: 471.

(7) The antisense oligonucleotide or a pharmaceutically acceptable salt thereof, or a hydrate thereof according to (3), wherein the antisense oligonucleotide is complementary to a nucleic acid comprising at least 15 consecutive bases in a target region selected from the group consisting of positions 14 to 33, 34 to 53, 54 to 73, 148 to 167, 397 to 432, 747 to 778, 965 to 984, 1127 to 1146, 1148 to 1173, 1182 to 1213, 1228 to 1254, 1270 to 1308, 1484 to 1564, 1578 to 1629, 1686 to 1705, 1748 to 1767, 1768 to 1787, 1794 to 1813, 1870 to 1913, 2015 to 2034, 2086 to 2118, 2129 to 2148, 2151 to 2170, 2206 to 2225, 2239 to 2272, 2287 to 2336, 2337 to 2373, 2387 to 2406, 2598 to 2632, 2633 to 2668, 2672 to 2691, 2699 to 2757, 2775 to 2809, 2826 to 2866, 2959 to 2978, 3032 to 3051, 3052 to 3071, 3136 to 3155, 3168 to 3187, 3188 to 3207, 3232 to 3270, 3298 to 3317, 3325 to 3344, 3408 to 3427, 3590 to 3690, 3691 to 3728, 3739 to 3769, 3877 to 3896, 3949 to 3983, 3984 to 4030, and 4170 to 4198 of the base sequence of SEQ ID NO: 471.

(8) The antisense oligonucleotide or a pharmaceutically acceptable salt thereof, or a hydrate thereof according to (7), wherein the antisense oligonucleotide is complementary to a nucleic acid comprising at least 15 consecutive bases in a target region selected from the group consisting of positions 14 to 33, 34 to 53, 54 to 73, 148 to 167, 397 to 416, 413 to 432, 747 to 766, 756 to 775, 759 to 778, 965 to 984, 1127 to 1146, 1148 to 1167, 1151 to 1170, 1154 to 1173, 1182 to 1201, 1185 to 1204, 1188 to 1207, 1191 to 1210, 1194 to 1213, 1228 to 1247, 1231 to 1250, 1235 to 1254, 1270 to 1289, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1586 to 1605, 1589 to 1608, 1592 to 1611, 1595 to 1614, 1598 to 1617, 1601 to 1620, 1604 to 1623, 1607 to 1626, 1610 to 1629, 1686 to 1705, 1748 to 1767, 1768 to 1787, 1794 to 1813, 1870 to 1889, 1871 to 1890, 1874 to 1893, 1877 to 1896, 1880 to 1899, 1883 to 1902, 1886 to 1905, 1889 to 1908, 1894 to 1913, 2015 to 2034, 2086 to 2105, 2097 to 2116, 2099 to 2118, 2129 to 2148, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2598 to 2617, 2613 to 2632, 2633 to 2652, 2649 to 2668, 2672 to 2691, 2699 to 2718, 2702 to 2721, 2705 to 2724, 2708 to 2727, 2711 to 2730, 2714 to 2733, 2717 to 2736, 2720 to 2739, 2723 to 2742, 2726 to 2745, 2729 to 2748, 2738 to 2757, 2775 to 2794, 2790 to 2809, 2826 to 2845, 2829 to 2848, 2832 to 2851, 2835 to 2854, 2838 to 2857, 2841 to 2860, 2847 to 2866, 2959 to 2978, 3032 to 3051, 3052 to 3071, 3136 to 3155, 3168 to 3187, 3188 to 3207, 3232 to 3251, 3251 to 3270, 3298 to 3317, 3325 to 3344, 3408 to 3427, 3590 to 3609, 3608 to 3627, 3617 to 3636, 3635 to 3654, 3654 to 3673, 3671 to 3690, 3691 to 3710, 3709 to 3728, 3739 to 3758, 3750 to 3769, 3877 to 3896, 3949 to 3968, 3964 to 3983, 3984 to 4003, 3999 to 4018, 4011 to 4030, 4170 to 4189, 4173 to 4192, 4176 to 4195, and 4179 to 4198 of the base sequence of SEQ ID NO: 471.

(9) The antisense oligonucleotide or a pharmaceutically acceptable salt thereof, or a hydrate thereof according to (5) or (7), wherein the antisense oligonucleotide is complementary to a nucleic acid comprising at least 15 consecutive bases in a target region selected from the group consisting of positions 14 to 33, 34 to 53, 747 to 766, 1148 to 1167, 1289 to 1308, 1484 to 1564, 1578 to 1623, 1686 to 1705, 1748 to 1767, 1768 to 1787, 1794 to 1813, 1877 to 1905, 2151 to 2170, 2206 to 2225, 2239 to 2272, 2287 to 2336, 2337 to 2373, 2387 to 2406, 2613 to 2632, 2633 to 2668, 2672 to 2691, 2699 to 2748, 2775 to 2809, 2826 to 2860, 3032 to 3051, 3052 to 3071, 3168 to 3187, 3232 to 3270, 3408 to 3427, 3590 to 3690, 3691 to 3728, 3739 to 3758, 3877 to 3896, 3949 to 3983, 3984 to 4030, and 4179 to 4198 of the base sequence of SEQ ID NO: 471.

(10-1) The antisense oligonucleotide or a pharmaceutically acceptable salt thereof, or a hydrate thereof according to (9), wherein the antisense oligonucleotide is complementary to a nucleic acid comprising at least 15 consecutive bases in a target region selected from the group consisting of positions 14 to 33, 34 to 53, 747 to 766, 1148 to 1167, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1586 to 1605, 1589 to 1608, 1592 to 1611, 1595 to 1614, 1598 to 1617, 1601 to 1620, 1604 to 1623, 1686 to 1705, 1748 to 1767, 1768 to 1787, 1794 to 1813, 1877 to 1896, 1880 to 1899, 1883 to 1902, 1886 to 1905, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2613 to 2632, 2633 to 2652, 2649 to 2668, 2672 to 2691, 2699 to 2718, 2702 to 2721, 2705 to 2724, 2708 to 2727, 2711 to 2730, 2714 to 2733, 2717 to 2736, 2720 to 2739, 2723 to 2742, 2726 to 2745, 2729 to 2748, 2775 to 2794, 2790 to 2809, 2826 to 2845, 2829 to 2848, 2832 to 2851, 2835 to 2854, 2838 to 2857, 2841 to 2860, 3032 to 3051, 3052 to 3071, 3168 to 3187, 3232 to 3251, 3251 to 3270, 3408 to 3427, 3590 to 3609, 3608 to 3627, 3617 to 3636, 3635 to 3654, 3654 to 3673, 3671 to 3690, 3691 to 3710, 3709 to 3728, 3739 to 3758, 3877 to 3896, 3949 to 3968, 3964 to 3983, 3984 to 4003, 3999 to 4018, 4011 to 4030, and 4179 to 4198 of the base sequence of SEQ ID NO: 471.

(10-2) The antisense oligonucleotide or a pharmaceutically acceptable salt thereof, or a hydrate thereof according to (7), wherein the antisense oligonucleotide is complementary to a nucleic acid comprising at least 15 consecutive bases in a target region selected from the group consisting of positions 397 to 416, 759 to 778, 1127 to 1146, 1148 to 1173, 1182 to 1213, 1488 to 1525, 1586 to 1629, 1686 to 1705, 1768 to 1787, 1870 to 1908, 2097 to 2118, 2151 to 2170, 2239 to 2258, 2287 to 2306, 2317 to 2336, 2633 to 2652, 2702 to 2745, 2832 to 2866, 2959 to 2978, 3298 to 3317, 3635 to 3654, 3671 to 3690, 3691 to 3710, 3750 to 3983, 3984 to 4003, and 4170 to 4198 of the base sequence of SEQ ID NO: 471.

(10-3) The antisense oligonucleotide or a pharmaceutically acceptable salt thereof, or a hydrate thereof according to (7) or (8), wherein the antisense oligonucleotide is complementary to a nucleic acid comprising at least 15 consecutive bases in a target region selected from the group consisting of positions 397 to 416, 759 to 778, 1127 to 1146, 1148 to 1167, 1151 to 1170, 1154 to 1173, 1182 to 1201, 1185 to 1204, 1194 to 1213, 1488 to 1507, 1491 to 1510, 1506 to 1525, 1586 to 1605, 1589 to 1608, 1595 to 1614, 1598 to 1617, 1601 to 1620, 1604 to 1623, 1607 to 1626, 1610 to 1629, 1686 to 1705, 1768 to 1787, 1870 to 1889, 1871 to 1890, 1874 to 1893, 1877 to 1896, 1886 to 1905, 1889 to 1908, 2097 to 2116, 2099 to 2118, 2151 to 2170, 2239 to 2258, 2287 to 2306, 2317 to 2336, 2633 to 2652, 2702 to 2721, 2705 to 2724, 2708 to 2727, 2711 to 2730, 2714 to 2733, 2717 to 2736, 2720 to 2739, 2726 to 2745, 2832 to 2851, 2835 to 2854, 2841 to 2860, 2847 to 2866, 2959 to 2978, 3298 to 3317, 3635 to 3654, 3671 to 3690, 3691 to 3710, 3750 to 3769, 3964 to 3983, 3984 to 4003, 4170 to 4189, 4173 to 4192, 4176 to 4195, and 4179 to 4198 of the base sequence of SEQ ID NO: 471.

(10-4) The antisense oligonucleotide or a pharmaceutically acceptable salt thereof, or a hydrate thereof according to (7), wherein the antisense oligonucleotide is complementary to a nucleic acid comprising at least 15 consecutive bases in a target region selected from the group consisting of positions 397 to 416, 1194 to 1213, 1506 to 1525, 1586 to 1626, 1870 to 1896, 2097 to 2116, 2317 to 2336, 2633 to 2652, 2702 to 2739, 2841 to 2978, 3298 to 3317, 3635 to 3654, 3691 to 3710, 3750 to 3769, 3984 to 4003, and 4170 to 4198 of the base sequence of SEQ ID NO: 471.

(10-5) The antisense oligonucleotide or a pharmaceutically acceptable salt thereof, or a hydrate thereof according to (7) or (8), wherein the antisense oligonucleotide is complementary to a nucleic acid comprising at least 15 consecutive bases in a target region selected from the group consisting of positions 397 to 416, 1194 to 1213, 1506 to 1525, 1586 to 1605, 1595 to 1614, 1598 to 1617, 1604 to 1623, 1607 to 1626, 1870 to 1889, 1871 to 1890, 1874 to 1893, 1877 to 1896, 2097 to 2116, 2317 to 2336, 2633 to 2652, 2702 to 2721, 2708 to 2727, 2711 to 2730, 2714 to 2733, 2717 to 2736, 2720 to 2739, 2841 to 2860, 2959 to 2978, 3298 to 3317, 3635 to 3654, 3691 to 3710, 3750 to 3769, 3984 to 4003, 4170 to 4189, 4173 to 4192, 4176 to 4195, and 4179 to 4198 of the base sequence of SEQ ID NO: 471.

(11) The antisense oligonucleotide or a pharmaceutically acceptable salt thereof, or a hydrate thereof according to (7), wherein the antisense oligonucleotide is complementary to a nucleic acid comprising at least 15 consecutive bases in a target region selected from the group consisting of positions 1598 to 1626, 1870 to 1890, 2097 to 2116, 2711 to 2736, 2841 to 2860, and 4170 to 4198 of the base sequence of SEQ ID NO: 471.

(12) The antisense oligonucleotide or a pharmaceutically acceptable salt thereof, or a hydrate thereof according to (7) or (8), wherein the antisense oligonucleotide is complementary to a nucleic acid comprising at least 15 consecutive bases in a target region selected from the group consisting of positions 1598 to 1617, 1604 to 1623, 1607 to 1626, 1870 to 1889, 1871 to 1890, 2097 to 2116, 2711 to 2730, 2714 to 2733, 2717 to 2736, 2841 to 2860, 4170 to 4189, 4173 to 4192, and 4179 to 4198 of the base sequence of SEQ ID NO: 471.

(12'-1) The antisense oligonucleotide or a pharmaceutically acceptable salt thereof, or a hydrate thereof according to (5), wherein the antisense oligonucleotide is complementary to a nucleic acid comprising at least 15 consecutive bases in a target region selected from the group consisting of positions 400 to 425, 1581 to 1624, 1878 to 1898, 2094 to 2113, 2629 to 2656, 2700 to 2741, 2839 to 2863, 2962 to 2981, 3302 to 3325, 3631 to 3658, 3687 to 3714, 3745 to 3764, 3980 to 4007, 4177 to 4199, and 4204 to 4223 of the base sequence of SEQ ID NO: 471.

(12'-2) The antisense oligonucleotide or a pharmaceutically acceptable salt thereof, or a hydrate thereof according to (5) or (6), wherein the antisense oligonucleotide is complementary to a nucleic acid comprising at least 15 consecutive bases in a target region selected from the group consisting of positions 400 to 419, 403 to 422, 406 to 425, 1581 to 1600, 1582 to 1601, 1583 to 1602, 1584 to 1603, 1585 to 1604, 1587 to 1606, 1588 to 1607, 1590 to 1609, 1591 to 1610, 1592 to 1611, 1593 to 1612, 1594 to 1613, 1596 to 1615, 1597 to 1616, 1599 to 1618, 1600 to 1619, 1602 to 1621, 1603 to 1622, 1605 to 1624, 1878 to 1897, 1879 to 1898, 2094 to 2113, 2629 to 2648, 2637 to 2656, 2700 to 2719, 2701 to 2720, 2703 to 2722, 2704 to 2723, 2706 to 2725, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 2722 to 2741, 2839 to 2858, 2840 to 2859, 2842 to 2861, 2843 to 2862, 2844 to 2863, 2962 to 2981, 3302 to 3321, 3306 to 3325, 3631 to 3650, 3632 to 3651, 3633 to 3652, 3634 to 3653, 3636 to 3655, 3637 to 3656, 3638 to 3657, 3639 to 3658, 3687 to 3706, 3695 to 3714, 3745 to 3764, 3980 to 3999, 3988 to 4007, 4177 to 4196, 4178 to 4197, 4180 to 4199, and 4204 to 4223 of the base sequence of SEQ ID NO: 471.

(12'-3) The antisense oligonucleotide or a pharmaceutically acceptable salt thereof, or a hydrate thereof according to (5), wherein the antisense oligonucleotide is complementary to a nucleic acid comprising at least 15 consecutive bases in a target region selected from the group consisting of positions 400 to 425, 1581 to 1624, 1878 to 1898, 2637 to 2656, 2700 to 2741, 2839 to 2863, 2962 to 2981, 3302 to 3325, 3631 to 3658, 3687 to 3706, 3745 to 3764, 4177 to 4199, and 4204 to 4223 of the base sequence of SEQ ID NO: 471.

(12'-4) The antisense oligonucleotide or a pharmaceutically acceptable salt thereof, or a hydrate thereof according to (5) or (6), wherein the antisense oligonucleotide is complementary to a nucleic acid comprising at least 15 consecutive bases in a target region selected from the group consisting of positions 400 to 419, 403 to 422, 406 to 425, 1581 to 1600, 1582 to 1601, 1583 to 1602, 1584 to 1603, 1585 to 1604, 1587 to 1606, 1588 to 1607, 1591 to 1610, 1592 to 1611, 1593 to 1612, 1594 to 1613, 1596 to 1615, 1597 to 1616, 1600 to 1619, 1602 to 1621, 1603 to 1622, 1605 to 1624, 1878 to 1897, 1879 to 1898, 2637 to 2656, 2700 to 2719, 2701 to 2720, 2703 to 2722, 2704 to 2723, 2706 to 2725, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 2722 to 2741, 2839 to 2858, 2840 to 2859, 2842 to 2861, 2843 to 2862, 2844 to 2863, 2962 to 2981, 3302 to 3321, 3306 to 3325, 3631 to 3650, 3632 to 3651, 3633 to 3652, 3634 to 3653, 3636 to 3655, 3637 to 3656, 3638 to 3657, 3639 to 3658, 3687 to 3706, 3745 to 3764, 4177 to 4196, 4178 to 4197, 4180 to 4199, and 4204 to 4223 of the base sequence of SEQ ID NO: 471.

(12'-5) The antisense oligonucleotide or a pharmaceutically acceptable salt thereof, or a hydrate thereof according to (5), wherein the antisense oligonucleotide is complementary to a nucleic acid comprising at least 15 consecutive bases in a target region selected from the group consisting of positions 1581 to 1624, 2703 to 2740, 3633 to 3655, and 4177 to 4199 of the base sequence of SEQ ID NO: 471.

(12'-6) The antisense oligonucleotide or a pharmaceutically acceptable salt thereof, or a hydrate thereof according to (5) or (6), wherein the antisense oligonucleotide is complementary to a nucleic acid comprising at least 15 consecutive bases in a target region selected from the group consisting of positions 1581 to 1600, 1582 to 1601, 1584 to 1603, 1585 to 1604, 1587 to 1606, 1588 to 1607, 1594 to 1613, 1596 to 1615, 1597 to 1616, 1602 to 1621, 1603 to 1622, 1605 to 1624, 2703 to 2722, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 3633 to 3652, 3634 to 3653, 3636 to 3655, 4177 to 4196, 4178 to 4197, and 4180 to 4199 of the base sequence of SEQ ID NO: 471.

(12'-7) The antisense oligonucleotide or a pharmaceutically acceptable salt thereof, or a hydrate thereof according to (5), wherein the antisense oligonucleotide is complementary to a nucleic acid comprising at least 15 consecutive bases in a target region selected from the group consisting of positions 1587 to 1616, 2712 to 2735, and 4180 to 4199 of the base sequence of SEQ ID NO: 471.

(12'-8) The antisense oligonucleotide or a pharmaceutically acceptable salt thereof, or a hydrate thereof according to (5) or (6), wherein the antisense oligonucleotide is complementary to a nucleic acid comprising at least 15 consecutive bases in a target region selected from the group consisting of positions 1587 to 1606, 1597 to 1616, 2712 to 2731, 2716 to 2735, and 4180 to 4199 of the base sequence of SEQ ID NO: 471.

(13) The antisense oligonucleotide or a pharmaceutically acceptable salt thereof, or a hydrate thereof according to any one of (1) to (12), wherein the antisense oligonucleotide is complementary to a nucleic acid comprising at least 20 consecutive bases in the target region.

(14) The antisense oligonucleotide or a pharmaceutically acceptable salt thereof, or a hydrate thereof according to (3) or (4), comprising:

(i) a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464;

(ii) a base sequence having addition, deletion, or substitution of one or several base(s) in a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464; or (iii) a base sequence having 90% or more sequence identity with a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464.

(15) The antisense oligonucleotide or a pharmaceutically acceptable salt thereof, or a hydrate thereof according to (5) or (6), comprising:

(i) a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464;

(ii) a base sequence having addition, deletion, or substitution of one or several base(s) in a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464; or (iii) a base sequence having 90% or more sequence identity with a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464.

(16) The antisense oligonucleotide or a pharmaceutically acceptable salt thereof, or a hydrate thereof according to (7) or (8), comprising:

(i) a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163;

(ii) a base sequence having addition, deletion, or substitution of one or several base(s) in a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163; or (iii) a base sequence having 90% or more sequence identity with a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163.

(17-1) The antisense oligonucleotide or a pharmaceutically acceptable salt thereof, or a hydrate thereof according to (9) or (10-1), comprising:

(i) a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163;

(ii) a base sequence having addition, deletion, or substitution of one or several base(s) in a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163; or (iii) a base sequence having 90% or more sequence identity with a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163.

(17-2) The antisense oligonucleotide or a pharmaceutically acceptable salt thereof, or a hydrate thereof according to (10-2) or (10-3), comprising:

(i) a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163;

(ii) a base sequence having addition, deletion, or substitution of one or several base(s) in a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163; or (iii) a base sequence having 90% or more sequence identity with a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163.

(17-3) The antisense oligonucleotide or a pharmaceutically acceptable salt thereof, or a hydrate thereof according to (10-4) or (10-5), comprising:

(i) a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163;

(ii) a base sequence having addition, deletion, or substitution of one or several base(s) in a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163; or (iii) a base sequence having 90% or more sequence identity with a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163.

(18) The antisense oligonucleotide or a pharmaceutically acceptable salt thereof, or a hydrate thereof according to (11) or (12), comprising:

(i) a base sequence selected from the group consisting of SEQ ID NOs: 98, 100, 101, 104, 105, 116, 131 to 133, 143, 160, 161, and 163;

(ii) a base sequence having addition, deletion, or substitution of one or several base(s) in a base sequence selected from the group consisting of SEQ ID NOs: 98, 100, 101, 104, 105, 116, 131 to 133, 143, 160, 161, and 163; or (iii) a base sequence having 90% or more sequence identity with a base sequence selected from the group consisting of SEQ ID NOs: 98, 100, 101, 104, 105, 116, 131 to 133, 143, 160, 161, and 163.

(19-1) The antisense oligonucleotide or a pharmaceutically acceptable salt thereof, or a hydrate thereof according to (12'-1) or (12'-2), comprising:

(i) a base sequence selected from the group consisting of SEQ ID NOs: 21, 164 to 222, 233, 234, and 350 to 355;

(ii) a base sequence having addition, deletion, or substitution of one or several base(s) in a base sequence selected from the group consisting of SEQ ID NOs: 21, 164 to 222, 233, 234, and 350 to 355; or (iii) a base sequence having 90% or more sequence identity with a base sequence selected from the group consisting of SEQ ID NOs: 21, 164 to 222, 233, 234, and 350 to 355.

(19-2) The antisense oligonucleotide or a pharmaceutically acceptable salt thereof, or a hydrate thereof according to (12'-3) or (12'-4), comprising:

(i) a base sequence selected from the group consisting of SEQ ID NOs: 21, 164 to 171, 173 to 177, 179 to 184, 187 to 214, 216, 219 to 222, 233 to 234, and 350 to 355;

(ii) a base sequence having addition, deletion, or substitution of one or several base(s) in a base sequence selected from the group consisting of SEQ ID NOs: 21, 164 to 171, 173 to 177, 179 to 184, 187 to 214, 216, 219 to 222, 233 to 234, and 350 to 355; or (iii) a base sequence having 90% or more sequence identity with a base sequence selected from the group consisting of SEQ ID NOs: 21, 164 to 171, 173 to 177, 179 to 184, 187 to 214, 216, 219 to 222, 233 to 234, and 350 to 355.

(19-3) The antisense oligonucleotide or a pharmaceutically acceptable salt thereof, or a hydrate thereof according to (12'-5) or (12'-6), comprising:

(i) a base sequence selected from the group consisting of SEQ ID NOs: 167 to 171, 175 to 177, 180 to 182, 190, 193 to 202, 219 to 221, 233, and 351 to 353;

(ii) a base sequence having addition, deletion, or substitution of one or several base(s) in a base sequence selected from the group consisting of SEQ ID NOs: 167 to 171, 175 to 177, 180 to 182, 190, 193 to 202, 219 to 221, 233, and 351 to 353; or (iii) a base sequence having 90% or more sequence identity with a base sequence selected from the group consisting of SEQ ID NOs: 167 to 171, 175 to 177, 180 to 182, 190, 193 to 202, 219 to 221, 233, and 351 to 353.

(20) The antisense oligonucleotide or a pharmaceutically acceptable salt thereof, or a hydrate thereof according to (12'-7) or (12'-8), comprising:

(i) a base sequence selected from the group consisting of SEQ ID NOs: 170, 177, 196, 199, and 221;

(ii) a base sequence having addition, deletion, or substitution of one or several base(s) in a base sequence selected from the group consisting of SEQ ID NOs: 170, 177, 196, 199, and 221; or (iii) a base sequence having 90% or more sequence identity with a base sequence selected from the group consisting of SEQ ID NOs: 170, 177, 196, 199, and 221.

(21) The antisense oligonucleotide or a pharmaceutically acceptable salt thereof, or a hydrate thereof according to any one of (14) to (20), comprising the base sequence (i).

(22) An antisense oligonucleotide consisting of 15 to 22 nucleotides complementary to a nucleic acid comprising at least 15 consecutive bases in a target region selected from the group consisting of positions 468 to 487, 474 to 493, 583 to 602, 586 to 605, 619 to 638, 770 to 789, 774 to 793, 775 to 794, 778 to 797, 804 to 823, 851 to 870, 1160 to 1179, 1162 to 1181, 1170 to 1189, 1173 to 1192, 1205 to 1224, 1210 to 1229, 1216 to 1235, 1217 to 1236, 1219 to 1238, 1385 to 1404, 1441 to 1460, 1818 to 1837, 1902 to 1921, 1905 to 1924, 1908 to 1927, 1914 to 1933, 1931 to 1950, 2117 to 2136, 2749 to 2768, 3100 to 3119, and 4125 to 4144 of a base sequence of SEQ ID NO: 471, or a pharmaceutically acceptable salt thereof, or a hydrate thereof.

(23) The antisense oligonucleotide or a pharmaceutically acceptable salt thereof, or a hydrate thereof according to (22), comprising:

(i) a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159;

(ii) a base sequence having addition, deletion, or substitution of one or several base(s) in a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159; or (iii) a base sequence having 90% or more sequence identity with a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159.

(24) The antisense oligonucleotide or a pharmaceutically acceptable salt thereof, or a hydrate thereof according to (23), comprising the base sequence (i).

(25) The antisense oligonucleotide or a pharmaceutically acceptable salt thereof, or a hydrate thereof according to any one of (1) to (24), wherein the antisense oligonucleotide consists of 20 nucleotides.

(26) The antisense oligonucleotide or a pharmaceutically acceptable salt thereof, or a hydrate thereof according to any one of (1) to (25), wherein a sugar moiety and/or a phosphate-binding region of at least one nucleotide constituting the oligonucleotide is modified.

(27-1) The antisense oligonucleotide or a pharmaceutically acceptable salt thereof, or a hydrate thereof according to (26), wherein the antisense oligonucleotide is a gapmer comprising a gap region at the center, and two wing regions adjacent to the gap region on the 5' end side and the 3' end side (a 5' wing region and a 3' wing region).

(27-2) The antisense oligonucleotide or a pharmaceutically acceptable salt thereof, or a hydrate thereof according to (27-1), wherein the antisense oligonucleotide comprises, from the 5' to 3' direction, a 5' wing region of 5 nucleotides long, a gap region of 10 nucleotides long, and a 3' wing region of 5 nucleotides long.

(28) The antisense oligonucleotide or a pharmaceutically acceptable salt thereof, or a hydrate thereof according to (27-1) or (27-2), wherein bonds between nucleosides are all phosphorothioate bonds.

(29) The antisense oligonucleotide or a pharmaceutically acceptable salt thereof, or a hydrate thereof according to (27-1) or (27-2), wherein one or more of a bond between the 2nd and 3rd nucleosides, a bond between the 3rd and 4th nucleosides, and a bond between the 4th and 5th nucleosides from the 5' side of the 5' wing region are phosphodiester bonds, and/or one or more of a bond between the 1st and 2nd nucleosides, a bond between the 2nd and 3rd nucleosides, and a bond between the 3rd and 4th nucleosides from the 5' side of the 3' wing region are phosphodiester bonds, and bonds between the other nucleosides are all phosphorothioate bonds.

(30) The antisense oligonucleotide or a pharmaceutically acceptable salt thereof, or a hydrate thereof according to (29), wherein the bond between the 2nd and 3rd nucleosides, and the bond between the 4th and 5th nucleosides from the 5' side of the 5' wing region are phosphodiester bonds, and/or the bond between the 1st and 2nd nucleosides, and the bond between the 3rd and 4th nucleosides from the 5' side of the 3' wing region are phosphodiester bonds, and bonds between the other nucleosides are all phosphorothioate bonds.

(31) The antisense oligonucleotide or a pharmaceutically acceptable salt thereof, or a hydrate thereof according to (29), wherein the bond between the 2nd and 3rd nucleosides, the bond between the 3rd and 4th nucleosides, and the bond between the 4th and 5th nucleosides from the 5' side of the 5' wing region are phosphodiester bonds, and/or the bond between the 1st and 2nd nucleosides, the bond between the 2nd and 3rd nucleosides, and the bond between the 3rd and 4th nucleosides from the 5' side of the 3' wing region are phosphodiester bonds, and bonds between the other nucleosides are all phosphorothioate bonds.

(32) The antisense oligonucleotide or a pharmaceutically acceptable salt thereof, or a hydrate thereof according to any one of (27-1) to (31), wherein the wing region comprises a 2'-OMe (2'-O—$CH_3$) group and/or a 2'-O-MOE (2'-O—$CH_2CH_2OCH_3$) group.

(33) A pharmaceutical composition comprising the antisense oligonucleotide or a pharmaceutically acceptable salt thereof, or a hydrate thereof according to any one of (1) to (32).

(34) The antisense oligonucleotide or a pharmaceutically acceptable salt thereof, or a hydrate thereof according to any one of (1) to (32), or the pharmaceutical composition according to (33), for treating and/or preventing dentatorubral-pallidoluysian atrophy (DRPLA).

(35) A method for treating and/or preventing dentatorubral-pallidoluysian atrophy (DRPLA) comprising administering, to a subject, the antisense oligonucleotide or a pharmaceutically acceptable salt thereof, or a hydrate thereof according to any one of (1) to (32), or the pharmaceutical composition according to (33) or (34).

The present invention provides an antisense oligonucleotide targeting an ATN1 mRNA or pre-mRNA, or a pharmaceutically acceptable salt thereof, or a hydrate thereof, and a composition or the like comprising the antisense oligonucleotide or a pharmaceutically acceptable salt thereof, or a hydrate thereof.

Since mutant ATN1 that is a causative gene for DRPLA is directly inhibited in the present invention, a DRPLA therapeutic agent having high treatment satisfaction may be provided. In the present invention, since the antisense oligonucleotide can be designed with targeting mutant ATN1 that is a causative gene for DRPLA, a DRPLA therapeutic agent with few side effects may be provided in a preferred embodiment of the present invention. In one embodiment of the present invention, personalized medicine based on genetic information of individual patients can be provided.

DESCRIPTION OF EMBODIMENTS

In one embodiment, the present invention relates to an antisense oligonucleotide consisting of 15 to 22 nucleotides complementary to a nucleic acid comprising at least 15 consecutive bases in a target region selected from the group consisting of positions 1 to 84, 142 to 168, 197 to 224, 286 to 317, 324 to 370, 391 to 434, 519 to 540, 623 to 643, 690 to 780, 824 to 855, 860 to 897, 948 to 987, 1044 to 1072, 1125 to 1174, 1181 to 1213, 1228 to 1255, 1265 to 1327, 1334 to 1356, 1416 to 1440, 1447 to 1631, 1638 to 1667, 1675 to 1705, 1748 to 1823, 1838 to 1861, 1870 to 1913, 1920 to 1941, 2000 to 2040, 2047 to 2075, 2086 to 2120, 2129 to 2187, 2194 to 2415, 2451 to 2497, 2592 to 2759, 2766 to 2870, 2928 to 2948, 2955 to 2989, 3021 to 3086, 3133 to 3209, 3217 to 3284, 3295 to 3350, 3384 to 3436, 3562 to 3771, 3858 to 3905, 3931 to 4039, 4067 to 4134, 4170 to 4232, 4241 to 4283, and 4286 to 4355 of a base sequence of SEQ ID NO: 471, or a pharmaceutically acceptable salt thereof, or a hydrate thereof.

SEQ ID NO: 471 is a sequence of mRNA of human atrophin-1 (ATN1) (Gen Bank: NM 001007026). The sequence of SEQ ID NO: 471 is a base sequence comprising 4355 nucleotides, and a region consisting of positions 1691 to 1747 of SEQ ID NO: 1 corresponds to a repeat region comprising CAG/CAA repeat sequences. In one embodiment, a target sequence of the antisense oligonucleotide of the present invention does not comprise a repeat region comprising the CAG/CAA repeat sequences.

In one embodiment, the antisense oligonucleotide of the present invention is complementary to a nucleic acid comprising or consisting of at least 15, at least 16, at least 17, at least 18, at least 19, at least 20, and for example 20 consecutive bases in the target region.

As used herein, an antisense oligonucleotide "complementary" to a given nucleic acid is not limited to an antisense oligonucleotide that forms Watson-Crick base pairs with the intended nucleic acid, but also includes an antisense oligonucleotide that forms wobble base pairs therewith. Herein, the Watson-Crick base pair means a base pair that forms a hydrogen bond between adenine and thymine, between adenine and uracil, or between guanine and cytosine, and the wobble base pair means a base pair that forms a hydrogen bond between guanine and uracil, between inosine and uracil, between inosine and adenine, or between inosine and cytosine. The term "complementary base sequence" does not have to have 100% complementarity with the intended base sequence, and may comprise, for example, 1, 2, 3, 4, or 5 noncomplementary nucleotides based on the intended base sequence, or may be a base sequence shorter by 1 nucleotide, 2 nucleotides, 3 nucleotides, 4 nucleotides, or 5 nucleotides than the intended base sequence. In one embodiment, an antisense oligonucleotide "complementary" to a given nucleic acid has at least 90%, 91%, 92%, 93%, 94%, 95%, 96%, 97%, 98%, 99%, or 100% complementarity with the intended nucleic acid. Complementarity can be easily determined by those skilled in the art, and can be calculated, for example, by aligning two sequences, counting the number of nucleotides forming Watson-Crick base pairs or wobble base pairs between these sequences, dividing the number of nucleotides forming the base pairs by the total number of nucleotides of the sequence, and multiplying the resultant by 100.

An example of an antisense oligonucleotide "complementary" to a given nucleic acid includes an antisense oligonucleotide that can hybridize under stringent conditions to the nucleic acid. As used herein, the term "stringent conditions" may be any of low stringent conditions, moderate stringent conditions, and high stringent conditions. The term "low stringent conditions" is conditions of, for example, 5×SSC, 5×Denhardt's solution, 0.5% SDS, 50% formamide at 32° C. The term "moderate stringent conditions" is conditions of, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent conditions" is conditions of, for example, 5×SSC, 5×Denhardt's solution, 0.5% SDS, 50% formamide at 50° C., or 0.2×SSC, 0.1% SDS at 65° C. Under these conditions, base sequences with higher sequence identity are expected to be obtained efficiently at higher temperatures. Multiple factors are, however, involved in hybridization stringency including temperature, probe concentration, probe length, ionic strength, time, salt concentration and others, and those skilled in the art may appropriately select these factors to achieve similar stringency.

When commercially available kits are used for hybridization, for example, an AlkPhos Direct Labelling and Detection System (GE Healthcare) may be used. In this case, according to the attached protocol, after incubation with a labeled probe overnight, the membrane can be washed with a primary wash buffer containing 0.1% (w/v) SDS at 55° C., thereby detecting hybridization. Alternatively, when a probe is labeled with digoxigenin (DIG) using a commercially available reagent (e.g., a PCR Labelling Mix (Roche Diagnostics)) in producing the probe based on a target sequence, hybridization can be detected with a DIG Nucleic Acid Detection Kit (Roche Diagnostics) or the like.

The identity between base sequences may be determined using algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called BLASTN and BLASTX based on the BLAST algorithm have been developed (Altschul S F, et al.: J. Mol. Biol. 215: 403, 1990). When a base sequence is analyzed using BLASTN, the parameters are, for example, score=100 and wordlength=12. When BLAST and Gapped BLAST programs are used, the default parameters for each program are employed.

In one embodiment, the antisense oligonucleotide of the present invention may be, for example, 15 or more nucleotides long, 16 or more nucleotides long, 17 or more nucleotides long, 18 or more nucleotides long, 19 or more nucleotides long, 20 or more nucleotides long, 21 or more nucleotides long, 22 or more nucleotides long, 23 or more nucleotides long, 24 or more nucleotides long, 25 or more nucleotides long, 26 or more nucleotides long, 27 or more nucleotides long, 28 or more nucleotides long, 29 or more nucleotides long, or 30 nucleotides long, and may be 30 or less nucleotides long, 29 or less nucleotides long, 28 or less nucleotides long, 27 or less nucleotides long, 26 or less nucleotides long, 25 or less nucleotides long, 24 or less nucleotides long, 23 or less nucleotides long, 22 or less nucleotides long, 21 or less nucleotides long, 20 or less nucleotides long, 19 or less nucleotides long, 18 or less nucleotides long, 17 or less nucleotides long, 16 or less nucleotides long, or 15 nucleotides long. The antisense oligonucleotide of the present invention may consist of, for example, 15 to 30 nucleotides, 15 to 25 nucleotides, 15 to 24 nucleotides, 15 to 23 nucleotides, 15 to 22 nucleotides, 15 to 21 nucleotides, 15 to 20 nucleotides, 16 to 25 nucleotides, 17 to 25 nucleotides, 18 to 25 nucleotides, 19 to 25 nucleotides, 20 to 25 nucleotides, 16 to 24 nucleotides, 17 to 23 nucleotides, 18 to 22 nucleotides, 19 to 21 nucleotides, and for example, 20 nucleotides.

Examples of the pharmaceutically acceptable salt of the antisense oligonucleotide of the present invention are alkali metal salts such as salts of sodium, potassium and lithium; alkaline earth metal salts such as salts of calcium and magnesium; metal salts such as salts of aluminum, iron, zinc, copper, nickel, cobalt, etc.; ammonium salts; organic amine salts such as salts of t-octylamine, dibenzylamine, morpholine, glucosamine, phenylglycine alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium, and tris(hydroxymethyl)aminomethane; hydrohalide salts such as salts of hydrofluorates, hydrochlorides, hydrobromides, and hydroiodides; inorganic acid salts such as nitrates, perchlorates, sulfates, and phosphates; lower alkane sulfonates such as methanesulfonates, trifluoromethanesulfonates and ethanesulfonates; arylsulfonates such as benzenesulfonates, and p-toluenesulfonates; organic acid salts such as acetates, malates, fumarates, succinates, citrates, tartrates, oxalates, and maleates; and amino acid salts such as salts of glycine, lysine, arginine, ornithine, glutamic acid, and aspartic acid. These salts may be produced by known methods. Alternatively, the antisense oligonucleotide of the present invention may be in the form of a hydrate thereof.

The antisense oligonucleotide of the present invention is composed of nucleotides as constituent units, and such nucleotides may be any of ribonucleotides, deoxyribonucleotides, and modified nucleotides.

The modified nucleotide refers to one fully or partly modified in a nucleobase, a sugar moiety and a phosphate-binding region that constitute the ribonucleotide or deoxyribonucleotide.

The nucleobase includes, for example, adenine, guanine, hypoxanthine, cytosine, thymine, uracil, and modified bases thereof. Examples of such modified bases include, but are not limited to, pseudouracil, 3-methyluracil, dihydrouracil, 5-alkylcytosines (e.g., 5-methylcytosine), 5-alkyluracils (e.g., 5-ethyluracil), 5-halouracils (e.g., 5-bromouracil), 6-azapyrimidine, 6-alkylpyrimidines (e.g., 6-methyluracil), 2-thiouracil, 4-thiouracil, 4-acetylcytosine, 5-(carboxyhydroxymethyl) uracil, 5-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, and xanthine.

As used herein, thymine "T" and uracil "U" are interchangeable with each other. Neither "T" nor "U" essentially influences the activity of the antisense oligonucleotide of the present invention, and therefore, in the base sequences shown in this specification, cases where "T" is "U" are also included, and these are indicated by the same sequence number. Besides, as used herein, a sequence comprising a modified base and a sequence not comprising the modified base are represented by the same SEQ ID NO. For example, "cytosine" and "methylcytosine" are interchangeable with each other, and cases where "cytosine" is "methylcytosine" are also included, and these are indicated by the same sequence number.

Modification of the sugar moiety may include, for example, modifications at the 2'-position of ribose, and modifications of the other portions of the sugar. The modification at the 2'-position of ribose includes a modification of replacing the 2'-OH of ribose with —OR, —OROR, —R, —R'OR, —SH, —SR, $—NH_2$, —NHR, $—NR_2$, $—N_3$, —CN, —F, —Cl, —Br or —I, for example, —OMe(—O—$CH_3$) or —O— methoxyethyl (—O-MOE: —O—$CH_2CH_2OCH_3$). Here, R represents an alkyl, a cycloalkyl, an acyl, or an aryl, and R' represents an alkylene.

The modification for the other portions of the sugar includes, for example, replacement of 0 at the 4'-position of ribose or deoxyribose with S, bridging between 2'- and 4'-positions of the sugar, such as LNA (locked nucleic acid) or ENA (2'-O,4'-C-ethylene-bridged nucleic acids), but is not limited thereto.

The modification for the phosphate-binding region includes, for example, a modification of replacing phosphodiester bond with a phosphorothioate bond, a phosphorodithioate bond, an alkyl phosphonate bond, a phosphoramidate bond, or a boranophosphate bond (cf., e.g., Enya et al.: Bioorganic & Medicinal Chemistry, 2008, 18, 9154-9160) (cf., e.g., Japan Domestic Re-Publications of PCT Application Nos. 2006/129594 and 2006/038608).

As used herein, the alkyl is preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may optionally be substituted, and examples of such substituents are a halogen, an alkoxy, a cyano and a nitro. The alkyl may be substituted with 1 to 3 substituents.

As used herein, the cycloalkyl is preferably a cycloalkyl having 3 to 12 carbon atoms. Specific examples include cyclopropyl, cyclobutyl, cyclopentyl, cyclohexyl, cycloheptyl, cyclooctyl, cyclodecyl, and cyclododecyl.

As used herein, examples of the halogen include fluorine, chlorine, bromine, and iodine.

As used herein, the alkoxy is a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, and isohexyloxy. Among others, an alkoxy having 1 to 3 carbon atoms is preferred.

As used herein, the aryl is preferably an aryl having 6 to 10 carbon atoms. Specific examples include phenyl, α-naphthyl, and β-naphthyl. Among others, phenyl is preferred. The aryl may optionally be substituted, and examples of such substituents include an alkyl, a halogen, an alkoxy, a cyano and a nitro. The aryl may be substituted with 1 to 3 substituents.

As used herein, the alkylene is preferably a straight or branched alkylene having 1 to 6 carbon atoms. Specific examples include methylene, ethylene, trimethylene, tetramethylene, pentamethylene, hexamethylene, 2-(ethyl) trimethylene, and 1-(methyl) tetramethylene.

As used herein, the acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, and hexanoyl. Examples of the aroyl include benzoyl, toluoyl, and naphthoyl. The aroyl may optionally be substituted at substitutable positions, and may be substituted with an alkyl(s).

In one embodiment, the antisense oligonucleotide of the present invention is a gapmer comprising a gap region at the center, and two wing regions adjacent to the gap region on the 5' end side and the 3' end side (referred to also as the 5' wing region and the 3' wing region, respectively). The gap region is a region recognized by RNase H, and having a sugar moiety constituted by deoxyribonucleotide not modified. The wing region contains at least one modified nucleotide, and is, for example, fully constituted by a modified nucleotide (e.g., a ribonucleotide having modification at the 2'-position of ribose). In one embodiment, each of nucleosides of the 5' wing region and the 3' wing region comprises at least one, for example, two or more, three or more, four or more, or five or more modified sugar moieties, such as a 2'-OMe group and/or a 2'-O-MOE group, and for example, all nucleosides of the 5' wing region and the 3' wing region may comprise a 2'-OMe group and/or a 2'-O-MOE group. Besides, the nucleosides of the 5' wing region and the 3' wing region may comprise a modification in the base moiety, and may comprise, for example, at least one methylcytosine.

The length of the gap region is not limited, and may be, for example, 5 to 15, 8 to 12, 9 to 11, or 10 nucleotides long. The lengths of the 5' wing region and the 3' wing region are not limited, and may be, for example, independently 2 to 10, 3 to 8, 4 to 6, or 5 nucleotides long. In one embodiment, the length of the gap region is 10 nucleotides long, and the lengths of the 5' wing region and the 3' wing region are 5 nucleotides long.

In one embodiment, the gapmer of the present invention comprises one or more modifications of phosphate-binding regions, e.g., phosphorothioate bonds, and for example, one or more, two or more, three or more, four or more, five or more, ten or more, fifteen or more, and for example, all of bonds between nucleotides may be phosphorothioate bonds. In one embodiment, bonds between nucleosides are all phosphorothioate bonds in the gapmer of the present invention. In one embodiment, the gapmer of the present invention comprises, for example, in the 5' wing region and/or the 3' wing region, one or more, two or more, three or more, four or more, five or more, six or more, seven or more, eight or more, nine or more, or ten or more (e.g., two to six) phosphodiester bonds, and bonds between the other nucleosides are all phosphorothioate bonds. In one embodiment, one or more of a bond between the 2nd and 3rd nucleosides, a bond between the 3rd and 4th nucleosides, and a bond between the 4th and 5th nucleosides from the 5' side of the 5' wing region are phosphodiester bonds, and/or one or more of a bond between the 1st and 2nd nucleosides, a bond between the 2nd and 3rd nucleosides, and a bond between the 3rd and 4th nucleosides from the 5' side of the 3' wing region are phosphodiester bonds, and bonds between the other nucleosides are all phosphorothioate bonds. In one embodiment, the bond between the 2nd and 3rd nucleosides, and the bond between the 4th and 5th nucleosides from the 5' side of the 5' wing region are phosphodiester bonds, and/or the bond between the 1st and 2nd nucleosides, and the bond between the 3rd and 4th nucleosides from the 5' side of the 3' wing region are phosphodiester bonds, and bonds between the other nucleosides are all phosphorothioate bonds. In one embodiment, the bond between the 2nd and 3rd nucleosides, the bond between the 3rd and 4th nucleosides, and the bond between the 4th and 5th nucleosides from the 5' side of the 5' wing region are phosphodiester bonds, and/or the bond between the 1st and 2nd nucleosides, the bond between the 2nd and 3rd nucleosides, and the bond between the 3rd and 4th nucleosides from the 5' side of the 3' wing region are phosphodiester bonds, and bonds between the other nucleosides are all phosphorothioate bonds. In one embodiment, the bond between the 2nd and 3rd nucleosides, and the bond between the 3rd and 4th nucleosides from the 5' side of the 5' wing region are phosphodiester bonds, and/or the bond between the 2nd and 3rd nucleosides, and the bond between the 3rd and 4th nucleosides from the 5' side of the 3' wing region are phosphodiester bonds, and bonds between the other nucleosides are all phosphorothioate bonds. In one embodiment, the bond between the 3rd and 4th nucleosides, and the bond between the 4th and 5th nucleosides from the 5' side of the 5' wing region are phosphodiester bonds, and/or the bond between the 1st and 2nd nucleosides, and the bond between the 2nd and the 3rd nucleosides from the 5' side of the 3' wing region are phosphodiester bonds, and bonds between the other nucleosides are all phosphorothioate bonds. In one embodiment, the bond between the 2nd and 3rd nucleosides from the 5' side of the 5' wing region is a phosphodiester bond, and/or the bond between the 3rd and 4th nucleosides from the 5' side of the 3' wing region is a phosphodiester bond, and bonds between the other nucleosides are all phosphorothioate bonds. In one embodiment, the bond between the 3rd and 4th nucleosides from the 5' side of the 5' wing region is a phosphodiester bond, and/or the bond between the 2nd and 3rd nucleosides from the 5' side of the 3' wing region is a phosphodiester bond, and bonds between the other nucleosides are all phosphorothioate bonds. In one embodiment, the bond between the 4th and 5th nucleosides from the 5' side of the 5' wing region is a phosphodiester bonds, and/or the bond between the 1st and 2nd nucleosides from the 5' side of the 3' wing region is a phosphodiester bond, and bonds between the other nucleosides are all phosphorothioate bonds. In one embodiment, the gapmer of the present invention does not comprise a modification of a phosphate-binding region, and bonds between nucleosides may be all phosphodiester bonds.

In one embodiment, the antisense oligonucleotide of the present invention is complementary to a nucleic acid comprising at least 15 consecutive bases in a target region selected from the group consisting of positions 1 to 84, 142 to 168, 197 to 224, 286 to 317, 324 to 370, 391 to 434, 519 to 540, 623 to 643, 690 to 780, 824 to 855, 860 to 897, 948 to 987, 1044 to 1072, 1125 to 1174, 1181 to 1213, 1228 to 1255, 1265 to 1327, 1334 to 1356, 1416 to 1440, 1447 to 1631, 1638 to 1667, 1675 to 1705, 1748 to 1823, 1838 to 1861, 1870 to 1913, 1920 to 1941, 2000 to 2040, 2047 to 2075, 2086 to 2120, 2129 to 2187, 2194 to 2415, 2451 to 2497, 2592 to 2759, 2766 to 2870, 2928 to 2948, 2955 to 2989, 3021 to 3086, 3133 to 3209, 3217 to 3284, 3295 to 3350, 3384 to 3436, 3562 to 3771, 3858 to 3905, 3931 to 4039, 4067 to 4134, 4170 to 4232, 4241 to 4283, and 4286 to 4355 of the base sequence of SEQ ID NO: 471.

In one embodiment, the antisense oligonucleotide of the present invention is complementary to a nucleic acid comprising at least 15 consecutive bases in a target region selected from the group consisting of positions 1 to 84, 142 to 168, 391 to 434, 697 to 780, 962 to 980, 1125 to 1174, 1181 to 1213, 1228 to 1255, 1265 to 1320, 1454 to 1631, 1682 to 1705, 1748 to 1816, 1870 to 1913, 2015 to 2040, 2086 to 2120, 2129 to 2187, 2201 to 2408, 2592 to 2759, 2773 to 2870, 2955 to 2982, 3028 to 3079, 3133 to 3209, 3224 to 3277, 3295 to 3350, 3391 to 3429, 3562 to 3771, 3865 to 3898, 3938 to 4032, 4074 to 4127, and 4170 to 4225 of the base sequence of SEQ ID NO: 471.

In one embodiment, the antisense oligonucleotide of the present invention is complementary to a nucleic acid comprising at least 15 consecutive bases in a target region selected from the group consisting of positions 1 to 69, 331 to 363, 398 to 427, 697 to 773, 867 to 890, 955 to 980, 1132 to 1167, 1272 to 1320, 1454 to 1624, 1682 to 1705, 1748 to 1816, 1877 to 1906, 2007 to 2033, 2093 to 2113, 2136 to 2180, 2201 to 2408, 2458 to 2490, 2599 to 2752, 2773 to 2863, 2962 to 2982, 3028 to 3079, 3140 to 3202, 3224 to 3277, 3302 to 3343, 3391 to 3429, 3569 to 3764, 3865 to 3898, 3938 to 4032, 4074 to 4127, 4177 to 4225, 4248 to 4276, and 4293 to 4355 of the base sequence of SEQ ID NO: 471.

In one embodiment, the antisense oligonucleotide of the present invention is complementary to a nucleic acid comprising at least 15 consecutive bases in a target region selected from the group consisting of positions 1 to 69, 398 to 427, 697 to 773, 1132 to 1167, 1272 to 1320, 1454 to 1624, 1682 to 1705, 1748 to 1816, 1877 to 1906, 2093 to 2113, 2136 to 2180, 2201 to 2408, 2599 to 2752, 2773 to 2863, 2962 to 2982, 3028 to 3079, 3140 to 3202, 3224 to 3277, 3302 to 3343, 3391 to 3429, 3569 to 3764, 3865 to 3898, 3938 to 4032, and 4177 to 4225 of the base sequence of SEQ ID NO: 471.

In one embodiment, the antisense oligonucleotide of the present invention is complementary to a nucleic acid comprising at least 15 consecutive bases in a target region selected from the group consisting of positions 14 to 33, 34 to 53, 54 to 73, 148 to 167, 397 to 432, 723 to 742, 747 to 778, 965 to 984, 1127 to 1146, 1148 to 1173, 1182 to 1213, 1228 to 1254, 1270 to 1308, 1484 to 1564, 1578 to 1629, 1686 to 1705, 1748 to 1767, 1768 to 1787, 1794 to 1813, 1870 to 1913, 2015 to 2034, 2086 to 2118, 2129 to 2148, 2151 to 2184, 2206 to 2225, 2239 to 2272, 2287 to 2336, 2337 to 2373, 2387 to 2406, 2598 to 2757, 2775 to 2809, 2826 to 2866, 2959 to 2982, 3032 to 3051, 3052 to 3071, 3136 to 3155, 3168 to 3187, 3188 to 3207, 3232 to 3270, 3298 to 3344, 3408 to 3427, 3563 to 3582, 3590 to 3728, 3739 to 3769, 3877 to 3896, 3949 to 4030, and 4170 to 4225 of the base sequence of SEQ ID NO: 471.

In one embodiment, the antisense oligonucleotide of the present invention is complementary to a nucleic acid comprising at least 15 consecutive bases in a target region selected from the group consisting of positions 14 to 33, 34 to 53, 54 to 73, 148 to 167, 397 to 416, 398 to 417, 399 to 418, 400 to 419, 401 to 420, 402 to 421, 403 to 422, 404 to 423, 405 to 424, 406 to 425, 407 to 426, 408 to 427, 413 to 432, 723 to 742, 747 to 766, 756 to 775, 759 to 778, 965 to 984, 1127 to 1146, 1148 to 1167, 1151 to 1170, 1154 to 1173, 1182 to 1201, 1185 to 1204, 1188 to 1207, 1191 to 1210, 1194 to 1213, 1228 to 1247, 1231 to 1250, 1235 to 1254, 1270 to 1289, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1579 to 1598, 1580 to 1599, 1581 to 1600, 1582 to 1601, 1583 to 1602, 1584 to 1603, 1585 to 1604, 1586 to 1605, 1587 to 1606, 1588 to 1607, 1589 to 1608, 1590 to 1609, 1591 to 1610, 1592 to 1611, 1593 to 1612, 1594 to 1613, 1595 to 1614, 1596 to 1615, 1597 to 1616, 1598 to 1617, 1599 to 1618, 1600 to 1619, 1601 to 1620, 1602 to 1621, 1603 to 1622, 1604 to 1623, 1605 to 1624, 1607 to 1626, 1610 to 1629, 1686 to 1705, 1748 to 1767, 1768 to 1787, 1794 to 1813, 1870 to 1889, 1871 to 1890, 1874 to 1893, 1877 to 1896, 1878 to 1897, 1879 to 1898, 1880 to 1899, 1881 to 1900, 1882 to 1901, 1883 to 1902, 1884 to 1903, 1885 to 1904, 1886 to 1905, 1887 to 1906, 1889 to 1908, 1894 to 1913, 2015 to 2034, 2086 to 2105, 2093 to 2112, 2094 to 2113, 2097 to 2116, 2099 to 2118, 2129 to 2148, 2151 to 2170, 2165 to 2184, 2206 to 2225, 2239 to 2258, 2253 to 2272, 2287 to 2306, 2301 to 2320, 2317 to 2336, 2337 to 2356, 2354 to 2373, 2387 to 2406, 2598 to 2617, 2613 to 2632, 2614 to 2633, 2615 to 2634, 2616 to 2635, 2617 to 2636, 2618 to 2637, 2619 to 2638, 2620 to 2639, 2621 to 2640, 2622 to 2641, 2623 to 2642, 2624 to 2643, 2625 to 2644, 2626 to 2645, 2627 to 2646, 2628 to 2647, 2629 to 2648, 2630 to 2649, 2631 to 2650, 2632 to 2651, 2633 to 2652, 2634 to 2653, 2635 to 2654, 2636 to 2655, 2637 to 2656, 2638 to 2657, 2639 to 2658, 2640 to 2659, 2641 to 2660, 2642 to 2661, 2643 to 2662, 2644 to 2663, 2645 to 2664, 2646 to 2665, 2647 to 2666, 2648 to 2667, 2649 to 2668, 2663 to 2682, 2672 to 2691, 2673 to 2692, 2674 to 2693, 2675 to 2694, 2676 to 2695, 2677 to 2696, 2678 to 2697, 2679 to 2698, 2680 to 2699, 2681 to 2700, 2682 to 2701, 2683 to 2702, 2684 to 2703, 2685 to 2704, 2686 to 2705, 2687 to 2706, 2688 to 2707, 2689 to 2708, 2690 to 2709, 2691 to 2710, 2692 to 2711, 2693 to 2712, 2694 to 2713, 2695 to 2714, 2696 to 2715, 2697 to 2716, 2698 to 2717, 2699 to 2718, 2700 to 2719, 2701 to 2720, 2702 to 2721, 2703 to 2722, 2704 to 2723, 2705 to 2724, 2706 to 2725, 2707 to 2726, 2708 to 2727, 2709 to 2728, 2710 to 2729, 2711 to 2730, 2712 to 2731, 2713 to 2732, 2714 to 2733, 2715 to 2734, 2716 to 2735, 2717 to 2736, 2718 to 2737, 2719 to 2738, 2720 to 2739, 2721 to 2740, 2722 to 2741, 2723 to 2742, 2724 to 2743, 2725 to 2744, 2726 to 2745, 2727 to 2746, 2728 to 2747, 2729 to 2748, 2730 to 2749, 2731 to 2750, 2732 to 2751, 2733 to 2752, 2738 to 2757, 2775 to 2794, 2790 to 2809, 2826 to 2845, 2827 to 2846, 2828 to 2847, 2829 to 2848, 2830 to 2849, 2831 to 2850, 2832 to 2851, 2833 to 2852, 2834 to 2853, 2835 to 2854, 2836 to 2855, 2837 to 2856, 2838 to 2857, 2839 to 2858, 2840 to 2859, 2841 to 2860, 2842 to 2861, 2843 to 2862, 2844 to 2863, 2847 to 2866, 2959 to 2978, 2962 to 2981, 2963 to 2982, 3032 to 3051, 3052 to 3071, 3136 to 3155, 3168 to 3187, 3188 to 3207, 3232 to 3251, 3251 to 3270, 3298 to 3317, 3302 to 3321, 3303 to 3322, 3304 to 3323, 3305 to 3324, 3306 to 3325, 3307 to 3326, 3308 to 3327, 3309 to 3328, 3310 to 3329, 3311 to 3330, 3312 to 3331, 3313 to 3332, 3314 to 3333, 3315 to 3334, 3316 to 3335, 3317 to 3336, 3318 to 3337, 3319 to 3338, 3320 to 3339, 3321 to 3340, 3322 to 3341, 3323 to 3342, 3324 to 3343, 3325 to 3344, 3408 to 3427, 3563 to 3582, 3590 to 3609, 3608 to 3627, 3617 to 3636, 3618 to 3637, 3619 to 3638, 3620 to 3639, 3621 to 3640, 3622 to 3641, 3623 to 3642, 3624 to 3643, 3625 to 3644, 3626 to 3645, 3627 to 3646, 3628 to 3647, 3629 to 3648, 3630 to 3649, 3631 to 3650, 3632 to 3651, 3633 to 3652, 3634 to 3653, 3635 to 3654, 3636 to 3655, 3637 to 3656, 3638 to 3657, 3639 to 3658, 3640 to 3659, 3641 to 3660, 3642 to 3661, 3643 to 3662, 3644 to 3663, 3645 to 3664, 3646 to 3665, 3647 to 3666, 3648 to 3667, 3649 to 3668, 3650 to 3669, 3651 to 3670, 3652 to 3671, 3653 to 3672, 3654 to 3673, 3671 to 3690, 3672 to 3691, 3673 to 3692, 3674 to 3693, 3675 to 3694, 3676 to 3695, 3677 to 3696, 3678 to 3697, 3679 to 3698, 3680 to 3699, 3681 to 3700, 3682 to 3701, 3683 to 3702, 3684 to 3703, 3685 to 3704, 3686 to 3705, 3687 to 3706, 3688 to 3707, 3689 to 3708, 3690 to 3709, 3691 to 3710, 3692 to 3711, 3693 to 3712, 3694 to 3713, 3695 to 3714, 3696 to 3715, 3697 to 3716, 3698 to 3717, 3699 to 3718, 3700 to 3719, 3701 to 3720, 3702 to 3721, 3703 to 3722, 3704 to 3723, 3705 to 3724, 3706 to 3725, 3707 to 3726, 3708 to 3727, 3709 to 3728, 3739 to 3758, 3740 to 3759, 3741 to 3760, 3742 to 3761, 3743 to 3762, 3744 to 3763, 3745 to 3764, 3750 to 3769, 3877 to 3896, 3949 to 3968, 3964 to 3983, 3965 to 3984, 3966 to 3985, 3967 to 3986, 3968 to 3987, 3969 to 3988, 3970 to 3989, 3971 to 3990, 3972 to 3991, 3973 to 3992, 3974 to 3993, 3975 to 3994, 3976 to 3995, 3977 to 3996, 3978 to 3997, 3979 to 3998, 3980 to 3999, 3981 to 4000, 3982 to 4001, 3983 to 4002, 3984 to 4003, 3985 to 4004, 3986 to 4005, 3987 to 4006, 3988 to 4007, 3989 to 4008, 3990 to 4009, 3991 to 4010, 3992 to 4011, 3993 to 4012, 3994 to 4013, 3995 to 4014, 3996 to 4015, 3997 to 4016, 3998 to 4017, 3999 to 4018, 4011 to 4030, 4170 to 4189, 4173 to 4192, 4176 to 4195, 4177 to 4196, 4178 to 4197, 4179 to 4198, 4180 to 4199, 4181 to 4200, 4182 to 4201, 4183 to 4202, 4184 to 4203, 4185 to 4204, 4186 to 4205, 4187 to 4206, 4188 to 4207, 4189 to 4208, 4190 to 4209, 4191 to 4210, 4192 to 4211, 4193 to 4212, 4194 to 4213, 4195 to 4214, 4196 to 4215, 4197 to 4216, 4198 to 4217, 4199 to 4218, 4200 to 4219, 4201 to 4220, 4202 to 4221, 4203 to 4222, 4204 to 4223, 4205 to 4224, and 4206 to 4225 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464;

(ii) a base sequence having addition, deletion, or substitution of one or several base(s) in a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464; or (iii) a base sequence having 90% or more sequence identity with a base sequence selected from the group consisting of SEQ ID NOs: 1 to 6, 8, 9, 11, 14 to 24, 26, 29, 31 to 60, 66 to 67, 73 to 75, 79 to 82, 86 to 89, 92 to 111, 115 to 136, 138 to 145, 147 to 158, and 160 to 464, e.g., the base sequence (i).

As used herein, the term "several" used in the phrase of "base sequence having addition, deletion, or substitution of one or several base (s)" means, two, three, four, five, six, seven, eight, nine, or ten.

In one embodiment, the antisense oligonucleotide of the present invention is complementary to a nucleic acid comprising at least 15 consecutive bases in a target region selected from the group consisting of positions 14 to 33, 34 to 53, 398 to 427, 723 to 742, 747 to 766, 1148 to 1167, 1289 to 1308, 1484 to 1564, 1578 to 1624, 1686 to 1705, 1748 to 1767, 1768 to 1787, 1794 to 1813, 1877 to 1906, 2093 to 2113, 2151 to 2170, 2206 to 2225, 2239 to 2272, 2287 to 2336, 2337 to 2373, 2387 to 2406, 2613 to 2752, 2775 to 2809, 2826 to 2863, 2962 to 2982, 3032 to 3051, 3052 to 3071, 3168 to 3187, 3232 to 3270, 3302 to 3343, 3408 to 3427, 3590 to 3728, 3739 to 3764, 3877 to 3896, 3949 to 4030, and 4177 to 4225 of the base sequence of SEQ ID NO: 471.

In one embodiment, the antisense oligonucleotide of the present invention is complementary to a nucleic acid comprising at least 15 consecutive bases in a target region selected from the group consisting of positions 14 to 33, 34 to 53, 398 to 417, 399 to 418, 400 to 419, 401 to 420, 402 to 421, 403 to 422, 404 to 423, 405 to 424, 406 to 425, 407 to 426, 408 to 427, 723 to 742, 747 to 766, 1148 to 1167, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1579 to 1598, 1580 to 1599, 1581 to 1600, 1582 to 1601, 1583 to 1602, 1584 to 1603, 1585 to 1604, 1586 to 1605, 1587 to 1606, 1588 to 1607, 1589 to 1608, 1590 to 1609, 1591 to 1610, 1592 to 1611, 1593 to 1612, 1594 to 1613, 1595 to 1614, 1596 to 1615, 1597 to 1616, 1598 to 1617, 1599 to 1618, 1600 to 1619, 1601 to 1620, 1602 to 1621, 1603 to 1622, 1604 to 1623, 1605 to 1624, 1686 to 1705, 1748 to 1767, 1768 to 1787, 1794 to 1813, 1877 to 1896, 1878 to 1897, 1879 to 1898, 1880 to 1899, 1881 to 1900, 1882 to 1901, 1883 to 1902, 1884 to 1903, 1885 to 1904, 1886 to 1905, 1887 to 1906, 2093 to 2112, 2094 to 2113, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2613 to 2632, 2614 to 2633, 2615 to 2634, 2616 to 2635, 2617 to 2636, 2618 to 2637, 2619 to 2638, 2620 to 2639, 2621 to 2640, 2622 to 2641, 2623 to 2642, 2624 to 2643, 2625 to 2644, 2626 to 2645, 2627 to 2646, 2628 to 2647, 2629 to 2648, 2630 to 2649, 2631 to 2650, 2632 to 2651, 2633 to 2652, 2634 to 2653, 2635 to 2654, 2636 to 2655, 2637 to 2656, 2638 to 2657, 2639 to 2658, 2640 to 2659, 2641 to 2660, 2642 to 2661, 2643 to 2662, 2644 to 2663, 2645 to 2664, 2646 to 2665, 2647 to 2666, 2648 to 2667, 2649 to 2668, 2663 to 2682, 2672 to 2691, 2673 to 2692, 2674 to 2693, 2675 to 2694, 2676 to 2695, 2677 to 2696, 2678 to 2697, 2679 to 2698, 2680 to 2699, 2681 to 2700, 2682 to 2701, 2683 to 2702, 2684 to 2703, 2685 to 2704, 2686 to 2705, 2687 to 2706, 2688 to 2707, 2689 to 2708, 2690 to 2709, 2691 to 2710, 2692 to 2711, 2693 to 2712, 2694 to 2713, 2695 to 2714, 2696 to 2715, 2697 to 2716, 2698 to 2717, 2699 to 2718, 2700 to 2719, 2701 to 2720, 2702 to 2721, 2703 to 2722, 2704 to 2723, 2705 to 2724, 2706 to 2725, 2707 to 2726, 2708 to 2727, 2709 to 2728, 2710 to 2729, 2711 to 2730, 2712 to 2731, 2713 to 2732, 2714 to 2733, 2715 to 2734, 2716 to 2735, 2717 to 2736, 2718 to 2737, 2719 to 2738, 2720 to 2739, 2721 to 2740, 2722 to 2741, 2723 to 2742, 2724 to 2743, 2725 to 2744, 2726 to 2745, 2727 to 2746, 2728 to 2747, 2729 to 2748, 2730 to 2749, 2731 to 2750, 2732 to 2751, 2733 to 2752, 2775 to 2794, 2790 to 2809, 2826 to 2845, 2827 to 2846, 2828 to 2847, 2829 to 2848, 2830 to 2849, 2831 to 2850, 2832 to 2851, 2833 to 2852, 2834 to 2853, 2835 to 2854, 2836 to 2855, 2837 to 2856, 2838 to 2857, 2839 to 2858, 2840 to 2859, 2841 to 2860, 2842 to 2861, 2843 to 2862, 2844 to 2863, 2962 to 2981, 2963 to 2982, 3032 to 3051, 3052 to 3071, 3168 to 3187, 3232 to 3251, 3251 to 3270, 3302 to 3321, 3303 to 3322, 3304 to 3323, 3305 to 3324, 3306 to 3325, 3307 to 3326, 3308 to 3327, 3309 to 3328, 3310 to 3329, 3311 to 3330, 3312 to 3331, 3313 to 3332, 3314 to 3333, 3315 to 3334, 3316 to 3335, 3317 to 3336, 3318 to 3337, 3319 to 3338, 3320 to 3339, 3321 to 3340, 3322 to 3341, 3323 to 3342, 3324 to 3343, 3408 to 3427, 3590 to 3609, 3608 to 3627, 3617 to 3636, 3618 to 3637, 3619 to 3638, 3620 to 3639, 3621 to 3640, 3622 to 3641, 3623 to 3642, 3624 to 3643, 3625 to 3644, 3626 to 3645, 3627 to 3646, 3628 to 3647, 3629 to 3648, 3630 to 3649, 3631 to 3650, 3632 to 3651, 3633 to 3652, 3634 to 3653, 3635 to 3654, 3636 to 3655, 3637 to 3656, 3638 to 3657, 3639 to 3658, 3640 to 3659, 3641 to 3660, 3642 to 3661, 3643 to 3662, 3644 to 3663, 3645 to 3664, 3646 to 3665, 3647 to 3666, 3648 to 3667, 3649 to 3668, 3650 to 3669, 3651 to 3670, 3652 to 3671, 3653 to 3672, 3654 to 3673, 3671 to 3690, 3672 to 3691, 3673 to 3692, 3674 to 3693, 3675 to 3694, 3676 to 3695, 3677 to 3696, 3678 to 3697, 3679 to 3698, 3680 to 3699, 3681 to 3700, 3682 to 3701, 3683 to 3702, 3684 to 3703, 3685 to 3704, 3686 to 3705, 3687 to 3706, 3688 to 3707, 3689 to 3708, 3690 to 3709, 3691 to 3710, 3692 to 3711, 3693 to 3712, 3694 to 3713, 3695 to 3714, 3696 to 3715, 3697 to 3716, 3698 to 3717, 3699 to 3718, 3700 to 3719, 3701 to 3720, 3702 to 3721, 3703 to 3722, 3704 to 3723, 3705 to 3724, 3706 to 3725, 3707 to 3726, 3708 to 3727, 3709 to 3728, 3739 to 3758, 3740 to 3759, 3741 to 3760, 3742 to 3761, 3743 to 3762, 3744 to 3763, 3745 to 3764, 3877 to 3896, 3949 to 3968, 3964 to 3983, 3965 to 3984, 3966 to 3985, 3967 to 3986, 3968 to 3987, 3969 to 3988, 3970 to 3989, 3971 to 3990, 3972 to 3991, 3973 to 3992, 3974 to 3993, 3975 to 3994, 3976 to 3995, 3977 to 3996, 3978 to 3997, 3979 to 3998, 3980 to 3999, 3981 to 4000, 3982 to 4001, 3983 to 4002, 3984 to 4003, 3985 to 4004, 3986 to 4005, 3987 to 4006, 3988 to 4007, 3989 to 4008, 3990 to 4009, 3991 to 4010, 3992 to 4011, 3993 to 4012, 3994 to 4013, 3995 to 4014, 3996 to 4015, 3997 to 4016, 3998 to 4017, 3999 to 4018, 4011 to 4030, 4177 to 4196, 4178 to 4197, 4179 to 4198, 4180 to 4199, 4181 to 4200, 4182 to 4201, 4183 to 4202, 4184 to 4203, 4185 to 4204, 4186 to 4205, 4187 to 4206, 4188 to 4207, 4189 to 4208, 4190 to 4209, 4191 to 4210, 4192 to 4211, 4193 to 4212, 4194 to 4213, 4195 to 4214, 4196 to 4215, 4197 to 4216, 4198 to 4217, 4199 to 4218, 4200 to 4219, 4201 to 4220, 4202 to 4221, 4203 to 4222, 4204 to 4223, 4205 to 4224, and 4206 to 4225 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464;

(ii) a base sequence having addition, deletion, or substitution of one or several base(s) in a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464; or (iii) a base sequence having 90% or more sequence identity with a base sequence selected from the group consisting of SEQ ID NOs: 1, 5, 6, 14 to 24, 31 to 35, 37 to 40, 42 to 45, 47 to 50, 52 to 59, 73, 92 to 100, 103, 107 to 110, 120 to 136, 138 to 143, 150 to 153, 155 to 158, and 163 to 464, e.g., the base sequence (i).

In one embodiment, the antisense oligonucleotide of the present invention is complementary to a nucleic acid comprising at least 15 consecutive bases in a target region selected from the group consisting of positions 14 to 33, 34 to 53, 54 to 73, 148 to 167, 397 to 432, 747 to 778, 965 to 984, 1127 to 1146, 1148 to 1173, 1182 to 1213, 1228 to 1254, 1270 to 1308, 1484 to 1564, 1578 to 1629, 1686 to 1705, 1748 to 1767, 1768 to 1787, 1794 to 1813, 1870 to 1913, 2015 to 2034, 2086 to 2118, 2129 to 2148, 2151 to 2170, 2206 to 2225, 2239 to 2272, 2287 to 2336, 2337 to 2373, 2387 to 2406, 2598 to 2632, 2633 to 2668, 2672 to 2691, 2699 to 2757, 2775 to 2809, 2826 to 2866, 2959 to 2978, 3032 to 3051, 3052 to 3071, 3136 to 3155, 3168 to 3187, 3188 to 3207, 3232 to 3270, 3298 to 3317, 3325 to 3344, 3408 to 3427, 3590 to 3690, 3691 to 3728, 3739 to 3769, 3877 to 3896, 3949 to 3983, 3984 to 4030, and 4170 to 4198 of the base sequence of SEQ ID NO: 471.

In one embodiment, the antisense oligonucleotide of the present invention is complementary to a nucleic acid comprising at least 15 consecutive bases in a target region selected from the group consisting of positions 14 to 33, 34 to 53, 54 to 73, 148 to 167, 397 to 416, 413 to 432, 747 to 766, 756 to 775, 759 to 778, 965 to 984, 1127 to 1146, 1148 to 1167, 1151 to 1170, 1154 to 1173, 1182 to 1201, 1185 to 1204, 1188 to 1207, 1191 to 1210, 1194 to 1213, 1228 to 1247, 1231 to 1250, 1235 to 1254, 1270 to 1289, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1586 to 1605, 1589 to 1608, 1592 to 1611, 1595 to 1614, 1598 to 1617, 1601 to 1620, 1604 to 1623, 1607 to 1626, 1610 to 1629, 1686 to 1705, 1748 to 1767, 1768 to 1787, 1794 to 1813, 1870 to 1889, 1871 to 1890, 1874 to 1893, 1877 to 1896, 1880 to 1899, 1883 to 1902, 1886 to 1905, 1889 to 1908, 1894 to 1913, 2015 to 2034, 2086 to 2105, 2097 to 2116, 2099 to 2118, 2129 to 2148, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2598 to 2617, 2613 to 2632, 2633 to 2652, 2649 to 2668, 2672 to 2691, 2699 to 2718, 2702 to 2721, 2705 to 2724, 2708 to 2727, 2711 to 2730, 2714 to 2733, 2717 to 2736, 2720 to 2739, 2723 to 2742, 2726 to 2745, 2729 to 2748, 2738 to 2757, 2775 to 2794, 2790 to 2809, 2826 to 2845, 2829 to 2848, 2832 to 2851, 2835 to 2854, 2838 to 2857, 2841 to 2860, 2847 to 2866, 2959 to 2978, 3032 to 3051, 3052 to 3071, 3136 to 3155, 3168 to 3187, 3188 to 3207, 3232 to 3251, 3251 to 3270, 3298 to 3317, 3325 to 3344, 3408 to 3427, 3590 to 3609, 3608 to 3627, 3617 to 3636, 3635 to 3654, 3654 to 3673, 3671 to 3690, 3691 to 3710, 3709 to 3728, 3739 to 3758, 3750 to 3769, 3877 to 3896, 3949 to 3968, 3964 to 3983, 3984 to 4003, 3999 to 4018, 4011 to 4030, 4170 to 4189, 4173 to 4192, 4176 to 4195, and 4179 to 4198 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163;

(ii) a base sequence having addition, deletion, or substitution of one or several base(s) in a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163; or (iii) a base sequence having 90% or more sequence identity with a base sequence selected from the group consisting of SEQ ID NOs: 1 to 4, 6, 8, 9, 11, 14 to 24, 26, 29, 31 to 37, 39 to 50, 52 to 60, 66 to 67, 73 to 75, 79 to 82, 86 to 89, 92 to 111, 115 to 118, 120 to 136, 138 to 145, 147 to 158, and 160 to 163, e.g., the base sequence (i).

In one embodiment, the antisense oligonucleotide of the present invention is complementary to a nucleic acid comprising at least 15 consecutive bases in a target region selected from the group consisting of positions 14 to 33, 34 to 53, 747 to 766, 1148 to 1167, 1289 to 1308, 1484 to 1564, 1578 to 1623, 1686 to 1705, 1748 to 1767, 1768 to 1787, 1794 to 1813, 1877 to 1905, 2151 to 2170, 2206 to 2225, 2239 to 2272, 2287 to 2336, 2337 to 2373, 2387 to 2406, 2613 to 2632, 2633 to 2668, 2672 to 2691, 2699 to 2748, 2775 to 2809, 2826 to 2860, 3032 to 3051, 3052 to 3071, 3168 to 3187, 3232 to 3270, 3408 to 3427, 3590 to 3690, 3691 to 3728, 3739 to 3758, 3877 to 3896, 3949 to 3983, 3984 to 4030, and 4179 to 4198 of the base sequence of SEQ ID NO: 471.

In one embodiment, the antisense oligonucleotide of the present invention is complementary to a nucleic acid comprising at least 15 consecutive bases in a target region selected from the group consisting of positions 14 to 33, 34 to 53, 747 to 766, 1148 to 1167, 1289 to 1308, 1484 to 1503, 1488 to 1507, 1491 to 1510, 1493 to 1512, 1506 to 1525, 1517 to 1536, 1531 to 1550, 1545 to 1564, 1578 to 1597, 1586 to 1605, 1589 to 1608, 1592 to 1611, 1595 to 1614, 1598 to 1617, 1601 to 1620, 1604 to 1623, 1686 to 1705, 1748 to 1767, 1768 to 1787, 1794 to 1813, 1877 to 1896, 1880 to 1899, 1883 to 1902, 1886 to 1905, 2151 to 2170, 2206 to 2225, 2239 to 2258, 2253 to 2272, 2287 to 2306, 2301 to 2320, 2317 to 2336, 2337 to 2356, 2354 to 2373, 2387 to 2406, 2613 to 2632, 2633 to 2652, 2649 to 2668, 2672 to 2691, 2699 to 2718, 2702 to 2721, 2705 to 2724, 2708 to 2727, 2711 to 2730, 2714 to 2733, 2717 to 2736, 2720 to 2739, 2723 to 2742, 2726 to 2745, 2729 to 2748, 2775 to 2794, 2790 to 2809, 2826 to 2845, 2829 to 2848, 2832 to 2851, 2835 to 2854, 2838 to 2857, 2841 to 2860, 3032 to 3051, 3052 to 3071, 3168 to 3187, 3232 to 3251, 3251 to 3270, 3408 to 3427, 3590 to 3609, 3608 to 3627, 3617 to 3636, 3635 to 3654, 3654 to 3673, 3671 to 3690, 3691 to 3710, 3709 to 3728, 3739 to 3758, 3877 to 3896, 3949 to 3968, 3964 to 3983, 3984 to 4003, 3999 to 4018, 4011 to 4030, and 4179 to 4198 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163;

(ii) a base sequence having addition, deletion, or substitution of one or several base(s) in a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163; or (iii) a base sequence having 90% or more sequence identity with a base sequence selected from the group consisting of SEQ ID NOs: 1, 6, 14 to 24, 31 to 35, 37, 39, 40, 42 to 45, 47 to 50, 52 to 59, 73, 92 to 100, 103, 107 to 110, 120 to 136, 138 to 143, 150 to 153, 155 to 158, and 163, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 1.0 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 397 to 416, 759 to 778, 1127 to 1146, 1148 to 1173, 1182 to 1213, 1488 to 1525, 1586 to 1629, 1686 to 1705, 1768 to 1787, 1870 to 1908, 2097 to 2118, 2151 to 2170, 2239 to 2258, 2287 to 2306, 2317 to 2336, 2633 to 2652, 2702 to 2745, 2832 to 2866, 2959 to 2978, 3298 to 3317, 3635 to 3654, 3671 to 3690, 3691 to 3710, 3750 to 3983, 3984 to 4003, and 4170 to 4198 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 397 to 416, 759 to 778, 1127 to 1146, 1148 to 1167, 1151 to 1170, 1154 to 1173, 1182 to 1201, 1185 to 1204, 1194 to 1213, 1488 to 1507, 1491 to 1510, 1506 to 1525, 1586 to 1605, 1589 to 1608, 1595 to 1614, 1598 to 1617, 1601 to 1620, 1604 to 1623, 1607 to 1626, 1610 to 1629, 1686 to 1705, 1768 to 1787, 1870 to 1889, 1871 to 1890, 1874 to 1893, 1877 to 1896, 1886 to 1905, 1889 to 1908, 2097 to 2116, 2099 to 2118, 2151 to 2170, 2239 to 2258, 2287 to 2306, 2317 to 2336, 2633 to 2652, 2702 to 2721, 2705 to 2724, 2708 to 2727, 2711 to 2730, 2714 to 2733, 2717 to 2736, 2720 to 2739, 2726 to 2745, 2832 to 2851, 2835 to 2854, 2841 to 2860, 2847 to 2866, 2959 to 2978, 3298 to 3317, 3635 to 3654, 3671 to 3690, 3691 to 3710, 3750 to 3769, 3964 to 3983, 3984 to 4003, 4170 to 4189, 4173 to 4192, 4176 to 4195, and 4179 to 4198 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163;

(ii) a base sequence having addition, deletion, or substitution of one or several base(s) in a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163; or (iii) a base sequence having 90% or more sequence identity with a base sequence selected from the group consisting of SEQ ID NOs: 9, 11, 16, 17, 22, 31, 60, 67, 73, 74, 75, 79, 80, 92, 95 to 107, 110, 111, 116, 117, 120 to 122, 126, 128 to 134, 136, 140, 141, 143 to 145, 148, 151 to 154, 156, 157, and 160 to 163, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 0.75 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 397 to 416, 1194 to 1213, 1506 to 1525, 1586 to 1626, 1870 to 1896, 2097 to 2116, 2317 to 2336, 2633 to 2652, 2702 to 2739, 2841 to 2978, 3298 to 3317, 3635 to 3654, 3691 to 3710, 3750 to 3769, 3984 to 4003, and 4170 to 4198 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 397 to 416, 1194 to 1213, 1506 to 1525, 1586 to 1605, 1595 to 1614, 1598 to 1617, 1604 to 1623, 1607 to 1626, 1870 to 1889, 1871 to 1890, 1874 to 1893, 1877 to 1896, 2097 to 2116, 2317 to 2336, 2633 to 2652, 2702 to 2721, 2708 to 2727, 2711 to 2730, 2714 to 2733, 2717 to 2736, 2720 to 2739, 2841 to 2860, 2959 to 2978, 3298 to 3317, 3635 to 3654, 3691 to 3710, 3750 to 3769, 3984 to 4003, 4170 to 4189, 4173 to 4192, 4176 to 4195, and 4179 to 4198 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163;

(ii) a base sequence having addition, deletion, or substitution of one or several base(s) in a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163; or (iii) a base sequence having 90% or more sequence identity with a base sequence selected from the group consisting of SEQ ID NOs: 11, 60, 92, 95, 97, 98, 100, 101, 104 to 107, 116, 122, 126, 128, 130 to 134, 143, 145, 148, 151, 153, 154, 157, and 160 to 163, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 0.5 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 1598 to 1626, 1870 to 1890, 2097 to 2116, 2711 to 2736, 2841 to 2860, and 4170 to 4198 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 1598 to 1617, 1604 to 1623, 1607 to 1626, 1870 to 1889, 1871 to 1890, 2097 to 2116, 2711 to 2730, 2714 to 2733, 2717 to 2736, 2841 to 2860, 4170 to 4189, 4173 to 4192, and 4179 to 4198 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 98, 100, 101, 104, 105, 116, 131 to 133, 143, 160, 161, and 163;

(ii) a base sequence having addition, deletion, or substitution of one or several base(s) in a base sequence selected from the group consisting of SEQ ID NOs: 98, 100, 101, 104, 105, 116, 131 to 133, 143, 160, 161, and 163; or (iii) a base sequence having 90% or more sequence identity with a base sequence selected from the group consisting of SEQ ID NOs: 98, 100, 101, 104, 105, 116, 131 to 133, 143, 160, 161, and 163, e.g., the base sequence (i).

In one embodiment, the antisense oligonucleotide of the present invention is complementary to a nucleic acid comprising at least 15 consecutive bases in a target region selected from the group consisting of positions 400 to 425, 1581 to 1624, 1878 to 1898, 2094 to 2113, 2629 to 2656, 2700 to 2741, 2839 to 2863, 2962 to 2981, 3302 to 3325, 3631 to 3658, 3687 to 3714, 3745 to 3764, 3980 to 4007, 4177 to 4199, and 4204 to 4223 of the base sequence of SEQ ID NO: 471.

In one embodiment, the antisense oligonucleotide of the present invention is complementary to a nucleic acid comprising at least 15 consecutive bases in a target region selected from the group consisting of positions 400 to 419, 403 to 422, 406 to 425, 1581 to 1600, 1582 to 1601, 1583 to 1602, 1584 to 1603, 1585 to 1604, 1587 to 1606, 1588 to 1607, 1590 to 1609, 1591 to 1610, 1592 to 1611, 1593 to 1612, 1594 to 1613, 1596 to 1615, 1597 to 1616, 1599 to 1618, 1600 to 1619, 1602 to 1621, 1603 to 1622, 1605 to 1624, 1878 to 1897, 1879 to 1898, 2094 to 2113, 2629 to 2648, 2637 to 2656, 2700 to 2719, 2701 to 2720, 2703 to 2722, 2704 to 2723, 2706 to 2725, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 2722 to 2741, 2839 to 2858, 2840 to 2859, 2842 to 2861, 2843 to 2862, 2844 to 2863, 2962 to 2981, 3302 to 3321, 3306 to 3325, 3631 to 3650, 3632 to 3651, 3633 to 3652, 3634 to 3653, 3636 to 3655, 3637 to 3656, 3638 to 3657, 3639 to 3658, 3687 to 3706, 3695 to 3714, 3745 to 3764, 3980 to 3999, 3988 to 4007, 4177 to 4196, 4178 to 4197, 4180 to 4199, and 4204 to 4223 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 21, 164 to 222, 233, 234, and 350 to 355;

(ii) a base sequence having addition, deletion, or substitution of one or several base(s) in a base sequence selected from the group consisting of SEQ ID NOs: 21, 164 to 222, 233, 234, and 350 to 355; or (iii) a base sequence having 90% or more sequence identity with a base sequence selected from the group consisting of SEQ ID NOs: 21, 164 to 222, 233, 234, and 350 to 355, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 1.0 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 400 to 425, 1581 to 1624, 1878 to 1898, 2637 to 2656, 2700 to 2741, 2839 to 2863, 2962 to 2981, 3302 to 3325, 3631 to 3658, 3687 to 3706, 3745 to 3764, 4177 to 4199, and 4204 to 4223 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 400 to 419, 403 to 422, 406 to 425, 1581 to 1600, 1582 to 1601, 1583 to 1602, 1584 to 1603, 1585 to 1604, 1587 to 1606, 1588 to 1607, 1591 to 1610, 1592 to 1611, 1593 to 1612, 1594 to 1613, 1596 to 1615, 1597 to 1616, 1600 to 1619, 1602 to 1621, 1603 to 1622, 1605 to 1624, 1878 to 1897, 1879 to 1898, 2637 to 2656, 2700 to 2719, 2701 to 2720, 2703 to 2722, 2704 to 2723, 2706 to 2725, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 2722 to 2741, 2839 to 2858, 2840 to 2859, 2842 to 2861, 2843 to 2862, 2844 to 2863, 2962 to 2981, 3302 to 3321, 3306 to 3325, 3631 to 3650, 3632 to 3651, 3633 to 3652, 3634 to 3653, 3636 to 3655, 3637 to 3656, 3638 to 3657, 3639 to 3658, 3687 to 3706, 3745 to 3764, 4177 to 4196, 4178 to 4197, 4180 to 4199, and 4204 to 4223 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 21, 164 to 171, 173 to 177, 179 to 184, 187 to 214, 216, 219 to 222, 233 to 234, and 350 to 355;

(ii) a base sequence having addition, deletion, or substitution of one or several base(s) in a base sequence selected from the group consisting of SEQ ID NOs: 21, 164 to 171, 173 to 177, 179 to 184, 187 to 214, 216, 219 to 222, 233 to 234, and 350 to 355; or (iii) a base sequence having 90% or more sequence identity with a base sequence selected from the group consisting of SEQ ID NOs: 21, 164 to 171, 173 to 177, 179 to 184, 187 to 214, 216, 219 to 222, 233 to 234, and 350 to 355, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 0.75 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 1581 to 1624, 2703 to 2740, 3633 to 3655, and 4177 to 4199 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 1581 to 1600, 1582 to 1601, 1584 to 1603, 1585 to 1604, 1587 to 1606, 1588 to 1607, 1594 to 1613, 1596 to 1615, 1597 to 1616, 1602 to 1621, 1603 to 1622, 1605 to 1624, 2703 to 2722, 2707 to 2726, 2709 to 2728, 2710 to 2729, 2712 to 2731, 2713 to 2732, 2715 to 2734, 2716 to 2735, 2718 to 2737, 2719 to 2738, 2721 to 2740, 3633 to 3652, 3634 to 3653, 3636 to 3655, 4177 to 4196, 4178 to 4197, and 4180 to 4199 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 167 to 171, 175 to 177, 180 to 182, 190, 193 to 202, 219 to 221, 233, and 351 to 353;

(ii) a base sequence having addition, deletion, or substitution of one or several base(s) in a base sequence selected from the group consisting of SEQ ID NOs: 167 to 171, 175 to 177, 180 to 182, 190, 193 to 202, 219 to 221, 233, and 351 to 353; or (iii) a base sequence having 90% or more sequence identity with a base sequence selected from the group consisting of SEQ ID NOs: 167 to 171, 175 to 177, 180 to 182, 190, 193 to 202, 219 to 221, 233, and 351 to 353, e.g., the base sequence (i).

In one embodiment, the antisense oligonucleotide of the present invention is selected from those having a ratio (average value) of the ATN-1 gene expression level obtained by administrating the antisense oligonucleotide to A204 cells to the ATN-1 gene expression level obtained by administrating OMe-6 or NRH-71, a positive control antisense oligonucleotide to A204 cells, of 0.5 or less in any of Examples, as measured by a method described in Examples of the present specification. Examples of such antisense oligonucleotides include antisense oligonucleotides consisting of 15 to 22 nucleotides complementary to a nucleic acid comprising at least 15 consecutive bases in a target region selected from the group consisting of positions 1587 to 1616, 2712 to 2735, and 4180 to 4199 of the base sequence of SEQ ID NO: 471. Other examples include antisense oligonucleotides consisting of 15 to 22 nucleotides complementary to a nucleic acid comprising at least 15 consecutive bases in a target region selected from the group consisting of positions 1587 to 1606, 1597 to 1616, 2712 to 2731, 2716 to 2735, and 4180 to 4199 of the base sequence of SEQ ID NO: 471.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 170, 177, 196, 199, and 221;

(ii) a base sequence having addition, deletion, or substitution of one or several base(s) in a base sequence selected from the group consisting of SEQ ID NOs: 170, 177, 196, 199, and 221; or (iii) a base sequence having 90% or more sequence identity with a base sequence selected from the group consisting of SEQ ID NOs: 170, 177, 196, 199, and 221, e.g., the base sequence (i).

In one embodiment, the present invention relates to an antisense oligonucleotide consisting of 15 to 22 nucleotides complementary to a nucleic acid comprising at least 15 consecutive bases in a target region selected from the group consisting of positions 468 to 487, 474 to 493, 583 to 602, 586 to 605, 619 to 638, 770 to 789, 774 to 793, 775 to 794, 778 to 797, 804 to 823, 851 to 870, 1160 to 1179, 1162 to 1181, 1170 to 1189, 1173 to 1192, 1205 to 1224, 1210 to 1229, 1216 to 1235, 1217 to 1236, 1219 to 1238, 1385 to 1404, 1441 to 1460, 1818 to 1837, 1902 to 1921, 1905 to 1924, 1908 to 1927, 1914 to 1933, 1931 to 1950, 2117 to 2136, 2749 to 2768, 3100 to 3119, and 4125 to 4144 of a base sequence of SEQ ID NO: 471, or a pharmaceutically acceptable salt thereof, or a hydrate thereof.

An example of the antisense oligonucleotide complementary to a nucleic acid comprising at least 15 consecutive bases in the target sequence includes an antisense oligonucleotide comprising or consisting of:

(i) a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159;

(ii) a base sequence having addition, deletion, or substitution of one or several base(s) in a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159; or (iii) a base sequence having 90% or more sequence identity with a base sequence selected from the group consisting of SEQ ID NOs: 7, 10, 12, 13, 25, 27, 28, 30, 61 to 65, 68 to 72, 76 to 78, 83 to 85, 90, 91, 112 to 114, 137, 146, and 159, e.g., the base sequence (i).

In one embodiment, the antisense oligonucleotide of the present invention inhibits the function of a target region. As used herein, the phrase "inhibit the function of a target region" encompasses one or more of cleaving with RNaseH of a genome RNA comprising the target region in which a double strand is formed by binding of the antisense oligonucleotide to the target region, inhibiting replication of the genome RNA comprising the target region, inhibiting translation when the target region is to be translated, and inhibiting transcription of the genome RNA comprising the target region. As used herein, the term "sub-genome RNA" refers to an RNA that is shorter than a genome RNA synthesized with the RNA-dependent RNA polymerase using a part of a negative-strand RNA as a template, which is synthesized with an RNA-dependent RNA polymerase using a positive-strand genome RNA as a template, and means an RNA working as an mRNA for viral protein synthesis (translation).

The antisense oligonucleotide of the present invention may be easily synthesized using various automated synthesizers (e.g., AKTA oligopilot plus 10/100 (GE Healthcare)). Alternatively, the synthesis may also be entrusted to a third-party organization (e.g., Promega Corp. or Takara Co.).

In one embodiment, the present invention relates to a pharmaceutical composition comprising an antisense oligonucleotide, or a pharmaceutically acceptable salt thereof, or a hydrate thereof. When the antisense nucleotide of the present invention is to be administered to a subject, the pharmaceutical composition of the present invention may comprise a carrier to promote delivery of the antisense nucleotide. Such a carrier is not particularly limited as far as it is pharmaceutically acceptable, and examples thereof include cationic carriers such as cationic liposomes, or cationic polymers, or carriers using viral envelope. The cationic liposomes include, for example, liposomes composed of 2-O-(2-diethylaminoethyl) carabamoyl-1,3-O-dioleoylglycerol and phospholipids as the essential constituents (hereinafter referred to as "liposome A"), Oligofectamine™ (manufactured by Invitrogen Corp.), Lipofectin™ (manufactured by Invitrogen Corp.), Lipofectamine™ (manufactured by Invitrogen Corp.), Lipofectamine™2000 (manufactured by Invitrogen Corp.), DMRIE-C (manufactured by Invitrogen Corp.), GeneSilencer® (manufactured by Gene Therapy Systems), TransMessenger® (manufactured by QIAGEN, Inc.), TransIT TKO® (manufactured by Mirus), and Nucleofector® II (Lonza). Examples of the cationic polymers include, for example, JetSI® (manufactured by Qbiogene, Inc.), and Jet-PEI® (polyethylenimine, manufactured by Qbiogene, Inc.). An example of carriers using viral envelop includes GenomeOne™ (HVJ-E liposome, manufactured by Ishihara Sangyo). Alternatively, the medical devices described in Japanese Patent No. 2924179, and the cationic carriers described in Japanese Domestic Re-Publication of PCT Application Nos. 2006/129594 and 2008/096690 may be used as well.

In one embodiment, the antisense oligonucleotide of the present invention may be in the form of a complex (conjugate) with a lipid or the like in the pharmaceutical composition to promote delivery of the antisense oligonucleotide. For example, as described in Bijsterbosch, M. K. et al., (2000) Nucleic Acid Res., 28, 2717-2725, the antisense oligonucleotide may be in the form of a conjugate with cholesterol.

The pharmaceutical composition of the present invention may comprise pharmaceutically acceptable additives in addition to the antisense oligonucleotide, or a pharmaceutically acceptable salt thereof, or a hydrate thereof and optionally the carrier described above. Examples of such additives are emulsification aids (e.g., fatty acids having 6 to 22 carbon atoms and their pharmaceutically acceptable salts, albumin and dextran), stabilizers (e.g., cholesterol, phosphatidic acid, mannitol, and sorbitol), isotonizing agents (e.g., sodium chloride, glucose, maltose, lactose, sucrose, and trehalose), and pH adjusting agents (e.g., hydrochloric acid, sulfuric acid, phosphoric acid, acetic acid, sodium hydroxide, potassium hydroxide, and triethanolamine). One or more of these additives can be used. The content of the additive in the composition of the present invention is appropriately 90 wt % or less, preferably 70 wt % or less, and more preferably 50 wt % or less.

The preparation method of the pharmaceutical composition of the present invention is not limited, and the preparation may be conducted by, for example, adding the antisense oligonucleotide of the present invention to a dispersion of the carrier, and appropriately stirring the resultant. The additive may be added in an appropriate step either before or after the addition of the antisense oligonucleotide of the present invention. An aqueous solvent used in adding the antisense oligonucleotide of the present invention is not particularly limited as long as it is pharmaceutically acceptable, and examples include injectable water, injectable distilled water, an electrolyte fluid such as physiological saline, and a sugar solution such as a glucose solution, or a maltose solution. Those skilled in the art can appropriately choose conditions for pH and temperature to be employed in this case.

The pharmaceutical composition of the present invention may be prepared into, for example, a liquid form or its lyophilized preparation. The lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions in a range of about −40° C. to −20° C., performing a primary drying in a range of about 0° C. to 10° C. under reduced pressure, and then performing a secondary drying in a range of about 15° C. to 25° C. under reduced pressure. In general, the lyophilized preparation of the composition of the present invention can be obtained by replacing the content of the vial with nitrogen gas and capping the resultant.

The lyophilized preparation of the pharmaceutical composition of the present invention can be used in general upon reconstitution by adding an optional suitable solution (reconstitution liquid). Examples of such a reconstitution liquid include injectable water, physiological saline and other general infusion fluids. A volume of the reconstitution liquid may vary depending on the intended use, etc., is not particularly limited, and is suitably 0.5-fold to 2-fold greater than the volume prior to the lyophilization or no more than 500 mL.

It is desired to control a dose of the pharmaceutical composition of the present invention to be administered by taking the following factors into account: the type and dosage form of the antisense oligonucleotide of the present invention contained; patients' conditions including age, body weight, etc.; administration route; and the characteristics and extent of the disease. A single dose for an adult calculated as the amount of the antisense oligonucleotide of the present invention can be 0.01 mg to 20 mg per kg body weight, preferably 0.03 mg to 10 mg per kg body weight, more preferably 0.05 mg to 4 mg per kg body weight, and further preferably 0.1 mg to 2 mg per kg body weight. The frequency of administration may be once per 1 to 3 days, once per week, or once per 2 to 3 weeks. This numerical range may vary occasionally depending on the type of the target disease, the administration form and the target molecule. Therefore, a dose or frequency of administration lower than these ranges may be sufficient in some occasion and conversely, a dose or frequency of administration higher than these ranges may be required occasionally.

The administration form of the pharmaceutical composition of the present invention is not particularly limited as long as it is pharmaceutically acceptable form of administration, and can be chosen depending upon method of treatment. Examples include intravenous administration, intraarterial administration, intramuscular administration, subcutaneous administration, oral administration, tissue administration, transdermal administration, pulmonary administration, nasal administration, and administration to central nerve. Examples of the administration to central nerve include intrathecal administration, intracranial administration, e.g., intracerebroventricular administration or lateral ventricle administration, intraparenchymal administration, and administration to leptomeninges (pia mater). Also, dosage forms which are available for the composition of the present invention are not particularly limited, and include, for example, various injections, oral agents, drips, inhalations, ointments, lotions, and poultices.

Examples of the subject to which the antisense oligonucleotide or the pharmaceutical composition of the present invention is administered include mammals, including primates such as a human, experimental animals such as a rat, a mouse, and a brown rat, and domestic animals such as a pig, a cow, a horse, and sheep, and the subject is preferably a human.

In one embodiment, the present invention relates to a method for treating and/or preventing dentatorubral-pallidoluysian atrophy (DRPLA), comprising administering, to a subject, the antisense oligonucleotide, or a pharmaceutically acceptable salt thereof, or a hydrate thereof, or the pharmaceutical composition of the present invention. The pharmaceutical composition, and the dose, the administration route and the like thereof in the present embodiment are the same as those described herein.

As used herein, treatment of dentatorubral-pallidoluysian atrophy (DRPLA) encompasses one or more of relief, improvement, and remission of dentatorubral-pallidoluysian atrophy or symptoms thereof (e.g., one or more of ataxia, myoclonus, epilepsy, and progressive intellectual deterioration in a child patient, and ataxia, choreoathetosis, dementia, and personality change in an adult patient). As used herein, prevention of DRPLA encompasses reduction of risks of causing DRPLA or the symptoms thereof.

EXAMPLES

Hereinafter, the present invention will be described in more detail with reference to Examples and Test Examples below, but the present invention is not limited thereto.

The term "gapmer" is defined as an oligomer compound, an oligonucleotide in general, having a center region of 2'-deoxyoligonucleotide flanked by two adjacent segments of non-deoxyoligonucleotides. The center region is called "gap", and the adjacent segments are called "wings". The gapmers used in the present examples have a gap of 10 nucleotides flanked by two adjacent wings of 5 nucleotides. These are called 5-10-5 gapmers.

Example 1: Synthesis of Gapmer (Oligonucleotide)

A gapmer (oligonucleotide) used in this example can be produced generally in accordance with a method described in W. Brad Wan et al., Nucleic Acid Research, Vol. 42, No. 22 13456 (2014), etc.

Among the gapmers used in the present example, some specific oligonucleotides having a 2'-methoxy (2'-OMe) group represented by the following formula (a) in a nucleoside of the wing were synthesized referring to the method described in W. Brad Wan et al., Nucleic Acid Research, Vol. 42, No. 22 13456 (2014) as described above. The others were obtained by entrusting the synthesis to GeneDesign Inc.

[Chem. 1]

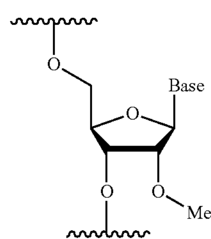

(a)

wherein Base represents cytosine (C), uracil (U), adenine (A), or guanine (G), and Me represents methyl.

Among the gapmers used in the present example, some specific oligonucleotides having a 2'-methoxyethyl (2'-O-MOE) group represented by the following formula (b) in a nucleoside of the wing were synthesized referring to the method described in W. Brad Wan et al., Nucleic Acid Research, Vol. 42, No. 22 13456 (2014) as described above.

[Chem. 2]

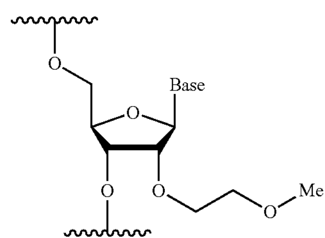

(b)

wherein Base represents 5-methylcytosine (C), thymine (T), adenine (A), or guanine (G), and Me represents methyl.

A 20 mer gapmer (oligonucleotide) to be tested having the 2'-OMe group represented by the formula (a) or the 2'-O-MOE group represented by the formula (b) in a nucleoside of the wing was synthesized at 1 μmol scale with an automated nucleic acid synthesizer, NTS M-8-MX DNA/RNA (NIHON TECHNO SERVICE CO., LTD.). The extension of chain length was performed in accordance with standard phosphoramidite protocol (solid-phase carrier: Glen UnySupport, DDTT ([(N,N-Dimethylaminomethylidene)amino]-3H-1,2,4-dithiazoline-3-thione), etc. was used for sulfuration, 0.02 M iodine/tetrahydrofuran:pyridine:water=7:1:2, etc. was used for oxidation). Thus, an oligonucleotide in which a hydroxyl group at the 5'-position at the end was protected with a dimethoxytrityl (DMTr) group, and the 3'-position was carried on a solid-phase was obtained. Subsequently, after removing the DMTr group by treatment with deblocking solution-1 obtained from FUJIFILM Wako Pure Chemical Corporation, the resultant was subjected to ammonia treatment, and thus, an objective product was cut out from the solid-phase carrier. The solvent was distilled off, and thus the obtained crude product was purified by reverse phase HPLC to give an objective product.

Example 2: Design of Gapmer (Oligonucleotide) to be Tested

A gapmer (oligonucleotide) to be tested was designed as an antisense oligonucleotide (ASO) targeting human atrophin-1 (ATN1) (Gen Bank: NM 001007026, SEQ ID NO: 471). Sequences of oligonucleotides expressed by DNA bases are shown in Tables 1, 2, 3, and 4.

In Tables 1 and 2, all oligonucleotides are 5-10-5 gapmers, and bonds between nucleosides are all phosphorothioates (P═S). In gapmers having a 2'-OMe group of Table 1, T (thymine) in the wing region is actually U (uracil). In gapmers having a 2'-O-MOE group of Table 2, C (cytosine) in the gap region and the wing regions is actually methyl C, and T in the wing regions is actually T.

TABLE 1

Table 1 Gapmer (oligonucleotide) to be tested having 2'-OMe group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| TCCTCCCACTTGGCGTCCAG | 1 | 14 | 33 | 1 | OMe-24 | 1 |
| AGAAGCAGAGCGGGAGGCCC | 2 | 54 | 73 | 1 | OMe-25 | 2 |
| TTCCCCACAGCTGTGGTCTG | 3 | 148 | 167 | 2 | OMe-97 | 3 |
| GTGGAGGCTTCCTCTACTCG | 4 | 413 | 432 | 4 | OMe-112 | 4 |
| AGGAGGAAAGAGTGGAGGTG | 5 | 723 | 742 | 5 | OMe-37 | 5 |
| GGTGCTGTCTGGCGGTTGAG | 6 | 747 | 766 | 5 | OMe-98 | 6 |
| TTCAAAGCTAGCCTCTGGCT | 7 | 774 | 793 | 5 | OMe-38 | 7 |
| TTAGGGCCCCCCACTGATGA | 8 | 965 | 984 | 5 | OMe-129 | 8 |
| GGCAGGTTCGGTGTCACATG | 9 | 1127 | 1146 | 5 | OMe-43 | 9 |
| AGAGGCTGATGCATTGTTGA | 10 | 1170 | 1189 | 5 | OMe-44 | 10 |
| TGGTTGGGCCCCCAGGCCAG | 11 | 1194 | 1213 | 5 | OMe-105 | 11 |

TABLE 1-continued

Table 1 Gapmer (oligonucleotide) to be tested having 2'-OMe group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GCAGATGACCAGGTAGTGGT | 12 | 1210 | 1229 | 5 | OMe-45 | 12 |
| GGAGAGGGCAGATGACCAGG | 13 | 1217 | 1236 | 5 | OMe-106 | 13 |
| GGTGAAGGAGCCAGAGTTGG | 14 | 1289 | 1308 | 5 | OMe-47 | 14 |
| GAGACAGAGAGGCTTGTTGG | 15 | 1484 | 1503 | 5 | OMe-23 | 15 |
| ATTGGAGACAGAGAGGCTTG | 16 | 1488 | 1507 | 5 | OMe-22 | 16 |
| CTGATTGGAGACAGAGAGGC | 17 | 1491 | 1510 | 5 | OMe-14 | 17 |
| GGCTGATTGGAGACAGAGAG | 18 | 1493 | 1512 | 5 | OMe-21 | 18 |
| AGAGAAGGCTGAGTATACTT | 19 | 1517 | 1536 | 5 | OMe-5 | 19 |
| ACCCTGGCTCCACACAGCCT | 20 | 1545 | 1564 | 5 | OMe-15 | 20 |
| GCATTGCTGTTGGCTAAGAG | 21 | 1592 | 1611 | 5 | OMe-50 | 21 |
| CTGTTGCTGTTGCTGGTGGT | 22 | 1686 | 1705 | 5 | OMe-131 | 22 |
| GGCCCAGAGTTTCCGTGATG | 23 | 1748 | 1767 | 5 | OMe-52 | 23 |
| GGAGCTACCGCCCTCCAGTG | 24 | 1794 | 1813 | 5 | OMc-53 | 24 |
| CATGGCGTAAGGGTGTGCGT | 25 | 1818 | 1837 | 5 | OMe-107 | 25 |
| AGGACACCTGGCTGTGAGGT | 26 | 1894 | 1913 | 5 | OMe-110 | 26 |
| GCCTGCTTGGCTGTAGGACA | 27 | 1908 | 1927 | 5 | OMe-55 | 27 |
| GAAGAGACTGGAGGGCCATT | 28 | 1931 | 1950 | 5 | OMe-111 | 28 |
| CCACGGTGGCAATGACCGTG | 29 | 2086 | 2105 | 5 | OMe-116 | 29 |
| GAGGCCGTTTTGTAGCCTGC | 30 | 2117 | 2136 | 5 | OMe-117 | 30 |
| GGCTCTCTTTCCGTACGGTG | 31 | 2151 | 2170 | 5 | OMe-60 | 31 |
| GCGACCCGGGTTTGTATCCG | 32 | 2206 | 2225 | 5 | OMe-118 | 32 |
| CGAGGTTCCTCGATAGCCCG | 33 | 2253 | 2272 | 5 | OMe-62 | 33 |
| TCCCACGGTGGGCGAGCCCG | 34 | 2301 | 2320 | 5 | OMe-63 | 34 |
| GGTGGTGGCAGCGATGGCAG | 35 | 2354 | 2373 | 5 | OMe-64 | 35 |
| CAGCTTGGAGCCCTCCAGTG | 36 | 2598 | 2617 | 6 | OMe-68 | 36 |
| CTGCTCGGCCTCGCGCCGCA | 37 | 2649 | 2668 | 6 | OMe-69 | 37 |
| TCTTCGCGCGCGCGCTGCTC | 38 | 2663 | 2682 | 6 | OMe-96 | 38 |
| TCTTTCTCGCGTTCCCGCTC | 39 | 2699 | 2718 | 6 | OMe-70 | 39 |
| TCAAGCTOGCGCTCCTTCT? | 40 | 2729 | 2748 | 6 | OMe-132 | 40 |
| ACGCTGCGTTCAAGCTCGCG | 41 | 2738 | 2757 | 6 | OMe-71 | 41 |
| GCATTCCACCGGAGCACGGC | 42 | 2775 | 2794 | 7 | OMe-133 | 42 |
| CGCACTGCCCGGTTCAAATG | 43 | 2826 | 2845 | 7 | OMe-73 | 43 |
| GCTTCCCGTTCCCTCTGCCG | 44 | 3032 | 3051 | 7 | OMe-77 | 44 |
| CACGGAGGTCTCGTTCACGG | 45 | 3052 | 3071 | 7 | OMe-135 | 45 |

TABLE 1-continued

Table 1 Gapmer (oligonucleotide) to be tested having 2'-OMe group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GAAAGGGATCCAAGCCCGGC | 46 | 3136 | 3155 | 7 | OMe-79 | 46 |
| GCCAGGCTGCAGAGCCAGGC | 47 | 3168 | 3187 | 7 | OMe-80 | 47 |
| CTAGACGTTCTCGCTCCAGG | 48 | 3232 | 3251 | 7 | OMe-136 | 48 |
| GCTGGCCCAGCTGCCAGCGC | 49 | 3251 | 3270 | 7 | OMe-82 | 49 |
| GTGCAGGTGCGAGTGGATGT | 50 | 3408 | 3427 | 7 | OMe-83 | 50 |
| AGAACTTCGTTCTCGTGCAG | 51 | 3563 | 3582 | 8 | OMe-86 | 51 |
| GAGGCCGGCAGGTCCCGGTA | 52 | 3608 | 3627 | 9 | OMe-87 | 52 |
| GCAGAAAGGGAGGCCGGCAG | 53 | 3617 | 3636 | 9 | OMe-123 | 53 |
| GTGCATGGCCTGCAGCTGAT | 54 | 3654 | 3673 | 9 | OMe-88 | 54 |
| CATGCAGCCACTGCTGCTGT | 55 | 3709 | 3728 | 9 | OMe-89 | 55 |
| GCAGCGGCACACTGTGCAGC | 56 | 3739 | 3758 | 9 | OMe-90 | 56 |
| CCCTCCCTCCCCCACTCTCT | 57 | 3949 | 3968 | 10 | OMe-9 | 57 |
| GCCACCTCCCCACCTCTGCA | 58 | 3999 | 4018 | 10 | OMe-10 | 58 |

TABLE 2

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GCAGGGGACAGCCTTGAAGT | 59 | 34 | 53 | 1 | DRA-3 | 59 |
| CTCGGGCCTTCTTGGCTGTC | 60 | 397 | 416 | 3 | DRA-29 | 60 |
| CTCACTTTCACTCTCTGAGA | 61 | 468 | 487 | 4 | DRA-9 | 61 |
| GGTCTCCTCACTTTCACTCT | 62 | 474 | 493 | 4 | DRA-96 | 62 |
| GGTCGCTGCTGCCATCATCA | 63 | 583 | 602 | 5 | DRA-105 | 63 |
| TAGGGTCGCTGCTGCCATCA | 64 | 586 | 605 | 5 | DRA-13 | 64 |
| GGGACGTGCTTCGGTTGTCC | 65 | 619 | 638 | 5 | DRA-14 | 65 |
| CTGTCGAGGGGTGCTGTCTG | 66 | 756 | 775 | 5 | DRA-108 | 66 |
| TGGCTGTOGAGGGGTGCTGT | 67 | 759 | 778 | 5 | DRA-109 | 67 |
| AAGCTAGCCTCTGGCTGTCG | 68 | 770 | 789 | 5 | DRA-112 | 68 |
| GTTCAAAGCTAGCCTCTGGC | 69 | 775 | 794 | 5 | NRH-156 | 69 |
| GGGGTTCAAAGCTAGCCTCT | 70 | 778 | 797 | 5 | DRA-113 | 70 |
| ATATCCAGTGGGTGTCACAG | 71 | 804 | 823 | 5 | DRA-16 | 71 |

TABLE 2-continued

| Table 2 Gapmer (oligonucleotide) to be tested having 2'-O-MOE group in wing nucleoside | | | | | | |
|---|---|---|---|---|---|---|
| ASO base sequence (DNA) 5' to 3' | ASO No. | Start position in SEQ ID NO: 471 | End position in SEQ ID NO: 471 | Target exon | ASO name | SEQ ID NO: |
| GGAGGAGCCTGGAACATTCG | 72 | 851 | 870 | 5 | DRA-17 | 72 |
| GGTCTCAGGGCAGGTGGGGG | 73 | 1148 | 1167 | 5 | DRA-128 | 73 |
| AGGGGTCTCAGGGCAGGTGG | 74 | 1151 | 1170 | 5 | DRA-129 | 74 |
| TTGAGGGGTCTCAGGGCAGG | 75 | 1154 | 1173 | 5 | DRA-130 | 75 |
| GCATTGTTGAGGGGTCTCAG | 76 | 1160 | 1179 | 5 | NRH-177 | 76 |
| ATGCATTGTTGAGGGGTCTC | 77 | 1162 | 1181 | 5 | NRH-171 | 77 |
| AGAGGCTGATGCATTGTTGA | 78 | 1170 | 1189 | 5 | NRH-178 | 10 |
| GGGAGAGGCTGATGCATTGT | 79 | 1173 | 1192 | 5 | NRH-174 | 78 |
| CAGGCCAGGGGGAGAGGCTG | 80 | 1182 | 1201 | 5 | NRH-175 | 79 |
| CCCCAGGCCAGGGGGAGAGG | 81 | 1185 | 1204 | 5 | NRH-176 | 80 |
| GGCCCCCAGGCCAGGGGGAG | 82 | 1188 | 1207 | 5 | NRH-181 | 81 |
| TTGGGCCCCCAGGCCAGGGG | 83 | 1191 | 1210 | 5 | NRH-182 | 82 |
| TGGTTGGGCCCCCAGGCCAG | 84 | 1194 | 1213 | 5 | NRH-179 | 11 |
| TGACCAGGTAGTGGTTGGGC | 85 | 1205 | 1224 | 5 | NRH-168 | 83 |
| GCAGATGACCAGGTAGTGGT | 86 | 1210 | 1229 | 5 | NRH-180 | 12 |
| GAGAGGGCAGATGACCAGGT | 88 | 1216 | 1235 | 5 | NRH-162 | 84 |
| GGAGAGGGCAGATGACCAGG | 89 | 1217 | 1236 | 5 | NRH-150 | 13 |
| GGGGAGAGGGCAGATGACCA | 90 | 1219 | 1238 | 5 | NRH-158 | 85 |
| CCATGGCGTGGGGAGAGGGC | 91 | 1228 | 1247 | 5 | DRA-133 | 85 |
| GTCCCATGGCGTGGGGAGAG | 92 | 1231 | 1250 | 5 | DRA-134 | 87 |
| CCCTGTCCCATGGCGTGGGG | 93 | 1235 | 1254 | 5 | DRA-21 | 88 |
| GGCCCTTCTCTGGGCCAGGA | 94 | 1270 | 1289 | 5 | DRA-31 | 89 |
| GAAGAGGAGGCTGCTGCAGA | 95 | 1385 | 1404 | 5 | DRA-24 | 90 |
| TGGGCAATGCCTGGGAAGCT | 96 | 1441 | 1460 | 5 | DRA-25 | 91 |
| AGTATACTTGGGGGGCTGAT | 97 | 1506 | 1525 | 5 | DRA-26 | 92 |
| CAGCCTGGGATGGGAGAGAA | 98 | 1531 | 1550 | 5 | DRA-32 | 93 |
| TAAGAGGCGGCCATAGGGAG | 99 | 1578 | 1597 | 5 | DRA-33 | 94 |
| CTGTTGGCTAAGAGGCGGCC | 100 | 1586 | 1605 | 5 | DRA-115 | 95 |
| TTGCTGTTGGCTAAGAGGCG | 101 | 1589 | 1608 | 5 | DRA-116 | 96 |
| TGGGCATTGCTGTTGGCTAA | 102 | 1595 | 1614 | 5 | DRA-117 | 97 |
| GGATGGGCATTGCTGTTGGC | 103 | 1598 | 1617 | 5 | DRA-118 | 98 |
| CCTGGATGGGCATTGCTGTT | 104 | 1601 | 1620 | 5 | DRA-119 | 99 |
| GGGCCTGGATGGGCATTGCT | 105 | 1604 | 1623 | 5 | DRA-34 | 100 |
| AAGGGGCCTGGATGGGCATT | 106 | 1607 | 1626 | 5 | DRA-120 | 101 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GGGAAGGGGCCTGGATGGGC | 107 | 1610 | 1629 | 5 | DRA-121 | 102 |
| GAAATGCTCCAGGAGGAGGG | 108 | 1768 | 1787 | 5 | DRA-36 | 103 |
| GCAGGTGTGCTGGCCCTGGT | 109 | 1870 | 1889 | 5 | NRH-154 | 104 |
| GGCAGGTGTGCTGGCCCTGG | 110 | 1871 | 1890 | 5 | NRH-160 | 105 |
| GGGGGCAGGTGTGCTGGCCC | 111 | 1874 | 1893 | 5 | DRA-140 | 106 |
| GGTGGGGGCAGGTGTGCTGG | 112 | 1877 | 1896 | 5 | DRA-141 | 107 |
| TGAGGTGGGGGCAGGTGTGC | 113 | 1880 | 1899 | 5 | DRA-142 | 108 |
| CTGTGAGGTGGGGGCAGGTG | 114 | 1883 | 1902 | 5 | DRA-143 | 109 |
| TGGCTGTGAGGTGGGGGCAG | 115 | 1886 | 1905 | 5 | DRA-144 | 110 |
| ACCTGGCTGTGAGGTGGGGG | 116 | 1889 | 1908 | 5 | DRA-145 | 111 |
| TTGGCTGTAGGACACCTGGC | 117 | 1902 | 1921 | 5 | DRA-148 | 112 |
| TGCTTGGCTGTAGGACACCT | 118 | 1905 | 1924 | 5 | DRA-149 | 113 |
| ATTGGGGCCTGCTTGGCTGT | 119 | 1914 | 1933 | 5 | DRA-152 | 114 |
| GGCGCCCCTTGAGGGCCCTG | 120 | 2015 | 2034 | 5 | DRA-42 | 115 |
| TGGCGAGGAAGCCACGGTGG | 121 | 2097 | 2116 | 5 | DRA-43 | 116 |
| GCTGGCGAGGAAGCCACGGT | 122 | 2099 | 2118 | 5 | DRA-185 | 117 |
| GAGGCCGTTTTGTAGCCTGC | 124 | 2117 | 2136 | 5 | DRA-191 | 30 |
| GGCCCAGGTGGGGAGGCCGT | 125 | 2129 | 2148 | 5 | DRA-195 | 118 |
| GCCCCCGGGGACGGGGCTCT | 126 | 2165 | 2184 | 5 | DRA-44 | 119 |
| AGCCCGGTGGGGTCCCCGTT | 127 | 2239 | 2258 | 5 | DRA-46 | 120 |
| AGCCCGGCTTGAAGGTCCCT | 128 | 2287 | 2306 | 5 | DRA-47 | 121 |
| GTGGCAGGGGCCCAGGTCCC | 129 | 2317 | 2336 | 5 | DRA-48 | 122 |
| CAGGCCTGAGGGCCCCGCAG | 130 | 2337 | 2356 | 5 | DRA-49 | 123 |
| CTCAGGGGCGGCCCTGAGGC | 131 | 2387 | 2406 | 5 | DRA-53 | 124 |
| GGCCCGCTTCTTGGCCAGCT | 132 | 2613 | 2632 | 6 | DRA-56 | 125 |
| CGCACCTTCTCCACCAGGTC | 133 | 2633 | 2652 | 6 | DRA-57 | 126 |
| CGCTCCTTTTCTTCGCGCGC | 134 | 2672 | 2691 | 6 | DRA-58 | 127 |
| CGCTCTTTCTCGCGTTCCCG | 135 | 2702 | 2721 | 6 | DRA-156 | 128 |
| TCGCGCTCTTTCTCGCGTTC | 136 | 2705 | 2724 | 6 | DRA-157 | 129 |
| CGCTCGCGCTCTTTCTCGCG | 137 | 2708 | 2727 | 6 | DRA-158 | 130 |
| TCGCGCTCGCGCTCTTTCTC | 138 | 2711 | 2730 | 6 | DRA-159 | 131 |
| TTCTCGCGCTCGCGCTCTTT | 139 | 2714 | 2733 | 6 | DRA-59 | 132 |
| TCCTTCTCGCGCTCGCGCTC | 140 | 2717 | 2736 | 6 | DRA-160 | 133 |
| CGCTCCTTCTCGCGCTCGCG | 141 | 2720 | 2739 | 6 | DRA-161 | 134 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| TCGCGCTCCTTCTCGCGCTC | 142 | 2723 | 2742 | 6 | DRA-162 | 135 |
| AGCTCGCGCTCCTTCTCGCG | 143 | 2726 | 2745 | 6 | DRA-163 | 136 |
| GAGCCAACTTCACGCTGCGT | 144 | 2749 | 2768 | 6 | DRA-60 | 137 |
| TGGGCCCAGAGATGGGCATT | 145 | 2790 | 2809 | 7 | DRA-61 | 138 |
| CACCGCACTGCCCGGTTCAA | 146 | 2829 | 2848 | 7 | DRA-122 | 139 |
| AGCCACCGCACTGCCCGGTT | 147 | 2832 | 2851 | 7 | DRA-123 | 140 |
| TGTAGCCACCGCACTGCCCG | 148 | 2835 | 2854 | 7 | DRA-124 | 141 |
| CACTGTAGCCACCGCACTGC | 149 | 2838 | 2857 | 7 | DRA-125 | 142 |
| GGGCACTGTAGCCACCGCAC | 150 | 2841 | 2860 | 7 | DRA-62 | 143 |
| GTAGGGGGGCACTGTAGCCA | 151 | 2847 | 2866 | 7 | DRA-126 | 144 |
| GGTCCACTGCCCCCAGGGGC | 152 | 2959 | 2978 | 7 | DRA-64 | 145 |
| GGGGTTCCAGCTCACTAGGC | 153 | 3100 | 3119 | 7 | DRA-66 | 146 |
| AAAGGGTGCAGGCCAGGTGG | 154 | 3188 | 3207 | 7 | DRA-68 | 147 |
| GCCTCTCAGCTGCCAGCCGC | 155 | 3298 | 3317 | 7 | DRA-69 | 148 |
| CCAGGGCCGCCACCCTTTCT | 156 | 3325 | 3344 | 7 | DRA-70 | 149 |
| TAAGGGGCAGCAAAGAGCTG | 157 | 3590 | 3609 | 8 | DRA-74 | 150 |
| TGAGCTGCTGACATCGGGGC | 158 | 3635 | 3654 | 9 | DRA-75 | 151 |
| AGCTCAGCTGACTGTGCGTG | 159 | 3671 | 3690 | 9 | DRA-76 | 152 |
| GTTCCAGCGCCAAGCGCTGC | 160 | 3691 | 3710 | 9 | DRA-77 | 153 |
| CTCCTGGGCAGGCAGCGGCA | 161 | 3750 | 3769 | 9 | DRA-78 | 154 |
| CAGGCCAAGGGCACGGTGGG | 162 | 3877 | 3896 | 10 | DRA-81 | 155 |
| TGGCCTTCTGTCTGTCCCTC | 163 | 3964 | 3983 | 10 | DRA-84 | 156 |
| CTGCACACCACATCGGGCCT | 164 | 3984 | 4003 | 10 | DRA-85 | 157 |
| GTCCCCATCCTCGCCACCTC | 165 | 4011 | 4030 | 10 | DRA-86 | 158 |
| AATCACACCAACGGGGCAGG | 166 | 4125 | 4144 | 10 | DRA-87 | 159 |
| TGGCACACGATGCTACGCAA | 167 | 4170 | 4189 | 10 | DRA-172 | 160 |
| GGGTGGCACACGATGCTACG | 168 | 4173 | 4192 | 10 | DRA-89 | 161 |
| CAGGGGTGGCACACGATGCT | 169 | 4176 | 4195 | 10 | DRA-173 | 162 |
| GGGCAGGGGTGGGACACGAT | 170 | 4179 | 4198 | 10 | DRA-174 | 163 |
| CTACTCGGGCCTTCTTGGCT | 171 | 400 | 419 | 3 | | 164 |
| CCTCTACTCGGGCCTTCTTG | 172 | 403 | 422 | 3 | | 165 |
| CTTCCTCTACTCGGGCCTTC | 173 | 406 | 425 | 3 | | 166 |
| GGCTAAGAGGCGGCCATAGG | 174 | 1581 | 1600 | 5 | | 167 |
| GTTGGCTAAGAGGCGGCCAT | 175 | 1584 | 1603 | 5 | | 168 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| TGTTGGCTAAGAGGCGGCCA | 176 | 1585 | 1604 | 5 | | 169 |
| GCTGTTGGCTAAGAGGCGGC | 177 | 1587 | 1606 | 5 | | 170 |
| TGCTGTTGGCTAAGAGGCGG | 178 | 1588 | 1607 | 5 | | 171 |
| ATTGCTGTTGGCTAAGAGGC | 179 | 1590 | 1609 | 5 | | 172 |
| CATTGCTGTTGGCTAAGAGG | 180 | 1591 | 1610 | 5 | | 173 |
| GCATTGCTGTTGGCTAAGAG | 181 | 1592 | 1611 | 5 | | 21 |
| GGCATTGCTGTTGGCTAAGA | 182 | 1593 | 1612 | 5 | | 174 |
| GGGCATTGCTGTTGGCTAAG | 183 | 1594 | 1613 | 5 | | 175 |
| ATGGGCATTGCTGTTGGCTA | 184 | 1596 | 1615 | 5 | | 176 |
| GATGGGCATTGCTGTTGGCT | 185 | 1597 | 1616 | 5 | | 177 |
| TGGATGGGCATTGCTGTTGG | 186 | 1599 | 1618 | 5 | | 178 |
| CTGGATGGGCATTGCTGTTG | 187 | 1600 | 1619 | 5 | | 179 |
| GCCTGGATGGGCATTGCTGT | 188 | 1602 | 1621 | 5 | | 180 |
| GGCCTGGATGGGCATTGCTG | 189 | 1603 | 1622 | 5 | | 181 |
| GGGGCCTGGATGGGCATTGC | 190 | 1605 | 1624 | 5 | | 182 |
| AGGTGGGGGCAGGTGTGCTG | 191 | 1878 | 1897 | 5 | | 183 |
| GAGGTGGGGGCAGGTGTGCT | 192 | 1879 | 1898 | 5 | | 184 |
| CGAGGAAGCCACGGTGGCAA | 193 | 2094 | 2113 | 5 | | 185 |
| CCTTCTCCACCAGGTCGGCC | 194 | 2629 | 2648 | 6 | | 186 |
| GCGCCGCACCTTCTCCACCA | 195 | 2637 | 2656 | 6 | | 187 |
| CTCTTTCTCGCGTTCCCGCT | 196 | 2700 | 2719 | 6 | | 188 |
| GCTCTTTCTCGCGTTCCCGC | 197 | 2701 | 2720 | 6 | | 189 |
| GCGCTCTTTCTCGCGTTCCC | 198 | 2703 | 2722 | 6 | | 190 |
| CGCGCTCTTTCTCGCGTTCC | 199 | 2704 | 2723 | 6 | | 191 |
| CTCGCGCTCTTTCTCGCGTT | 200 | 2706 | 2725 | 6 | | 192 |
| GCTCGCGCTCTTTCTCGCGT | 201 | 2707 | 2726 | 6 | | 193 |
| GCGCTCGCGCTCTTTCTOGC | 202 | 2709 | 2728 | 6 | | 194 |
| CGCGCTCGCGCTCTTTCTCG | 203 | 2710 | 2729 | 6 | | 195 |
| CTCGCGCTCGCGCTCTTTCT | 204 | 2712 | 2731 | 6 | | 196 |
| TCTCGCGCTCGCGCTCTTTC | 205 | 2713 | 2732 | 6 | | 197 |
| CTTCTCGCGCTCGCGCTCTT | 206 | 2715 | 2734 | 6 | | 198 |
| CCTTCTCGCGCTCGCGCTCT | 207 | 2716 | 2735 | 6 | | 199 |
| CTCCTTCTCGCGCTCGCGCT | 208 | 2718 | 2737 | 6 | | 200 |
| GCTCCTTCTCGCGCTCGCGC | 209 | 2719 | 2738 | 6 | | 201 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GCGCTCCTTCTCGCGCTCGC | 210 | 2721 | 2740 | 6 | | 202 |
| CGCGCTCCTTCTCGCGCTCG | 211 | 2722 | 2741 | 6 | | 203 |
| GCACTGTAGCCACCGCACTG | 212 | 2839 | 2858 | 7 | | 204 |
| GGCACTGTAGCCACCGCACT | 213 | 2840 | 2859 | 7 | | 205 |
| GGGGCACTGTAGCCACCGCA | 214 | 2842 | 2861 | 7 | | 206 |
| GGGGGCACTGTAGCCACCGC | 215 | 2843 | 2862 | 7 | | 207 |
| GGGGGGCACTGTAGCCACCG | 216 | 2844 | 2863 | 7 | | 208 |
| CCGGGTCCACTGCCCCCAGG | 217 | 2962 | 2981 | 7 | | 209 |
| TGCTGCCTCTCAGCTGCCAG | 218 | 3302 | 3321 | 7 | | 210 |
| TGCGTGCTGCCTCTCAGCTG | 219 | 3306 | 3325 | 7 | | 211 |
| CTGCTGACATCGGGGCAGAA | 220 | 3631 | 3650 | 9 | | 212 |
| CTGATGAGCTGCTGACATCG | 221 | 3639 | 3658 | 9 | | 213 |
| CAGCGCCAAGCGCTGCAGCT | 222 | 3687 | 3706 | 9 | | 214 |
| TGCTGTTCCAGCGCCAAGCG | 223 | 3695 | 3714 | 9 | | 215 |
| GGGCAGGCAGCGGCACACTG | 224 | 3745 | 3764 | 9 | | 216 |
| ACACCACATCGGGCCTTGGC | 225 | 3980 | 3999 | 10 | | 217 |
| ACCTCTGCACACCACATCGG | 226 | 3988 | 4007 | 10 | | 218 |
| GCAGGGGTGGCACACGATGC | 227 | 4177 | 4196 | 10 | | 219 |
| GGCAGGGGTGGCACACGATG | 228 | 4178 | 4197 | 10 | | 220 |
| GGGGCAGGGGTGGCACACGA | 229 | 4180 | 4199 | 10 | | 221 |
| GGGCGCGCACACAGGGATCG | 230 | 4204 | 4223 | 10 | | 222 |
| ACTCGGGCCTTCTTGGCTGT | 231 | 398 | 417 | 3 | | 223 |
| TACTCGGGCCTTCTTGGCTG | 232 | 399 | 418 | 3 | | 224 |
| TCTACTCGGGCCTTCTTGGC | 233 | 401 | 420 | 3 | | 225 |
| CTCTACTCGGGCCTTCTTGG | 234 | 402 | 421 | 3 | | 226 |
| TCCTCTACTCGGGCCTTCTT | 235 | 404 | 423 | 3 | | 227 |
| TTCCTCTACTCGGGCCTTCT | 236 | 405 | 424 | 3 | | 228 |
| GCTTCCTCTACTCGGGCCTT | 237 | 407 | 426 | 4 | | 229 |
| GGCTTCCTCTACTCGGGCCT | 238 | 408 | 427 | 4 | | 230 |
| CTAAGAGGCGGCCATAGGGA | 239 | 1579 | 1598 | 5 | | 231 |
| GCTAAGAGGCGGCCATAGGG | 240 | 1580 | 1599 | 5 | | 232 |
| TGGCTAAGAGGCGGCCATAG | 241 | 1582 | 1601 | 5 | | 233 |
| TTGGCTAAGAGGCGGCCATA | 242 | 1583 | 1602 | 5 | | 234 |
| GTGAGGTGGGGGCAGGTGTG | 243 | 1881 | 1900 | 5 | | 235 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| TGTGAGGTGGGGGCAGGTGT | 244 | 1882 | 1901 | 5 | | 236 |
| GCTGTGAGGTGGGGGCAGGT | 245 | 1884 | 1903 | 5 | | 237 |
| GGCTGTGAGGTGGGGGCAGG | 246 | 1885 | 1904 | 5 | | 238 |
| CTGGCTGTGAGGTGGGGGCA | 247 | 1887 | 1906 | 5 | | 239 |
| GAGGAAGCCACGGTGGCAAT | 248 | 2093 | 2112 | 5 | | 240 |
| CGGCCCGCTTCTTGGCCAGC | 249 | 2614 | 2633 | 6 | | 241 |
| TCGGCCCGCTTCTTGGCCAG | 250 | 2615 | 2634 | 6 | | 242 |
| GTCGGCCCGCTTCTTGGCCA | 251 | 2616 | 2635 | 6 | | 243 |
| GGTCGGCCCGCTTCTTGGCC | 252 | 2617 | 2636 | 6 | | 244 |
| AGGTCGGCCCGCTTCTTGGC | 253 | 2618 | 2637 | 6 | | 245 |
| CAGGTCGGCCCGCTTCTTGG | 254 | 2619 | 2638 | 6 | | 246 |
| CCAGGTCGGCCCGCTTCTTG | 255 | 2620 | 2639 | 6 | | 247 |
| ACCAGGTCGGCCCGCTTCTT | 256 | 2621 | 2640 | 6 | | 248 |
| CACCAGGTCGGCCCGCTTCT | 257 | 2622 | 2641 | 6 | | 249 |
| CCACCAGGTCGGCCCGCTTC | 258 | 2623 | 2642 | 6 | | 250 |
| TCCACCAGGTCGGCCCGCTT | 259 | 2624 | 2643 | 6 | | 251 |
| CTCCACCAGGTCGGCCCGCT | 260 | 2625 | 2644 | 6 | | 252 |
| TCTCCACCAGGTCGGCCCGC | 261 | 2626 | 2645 | 6 | | 253 |
| TTCTCCACCAGGTCGGCCCG | 262 | 2627 | 2646 | 6 | | 254 |
| CTTCTCCACCAGGTCGGCCC | 263 | 2628 | 2647 | 6 | | 255 |
| ACCTTCTCCACCAGGTCGGC | 264 | 2630 | 2649 | 6 | | 256 |
| CACCTTCTCCACCAGGTCGG | 265 | 2631 | 2650 | 6 | | 257 |
| GCACCTTCTCCACCAGGTCG | 266 | 2632 | 2651 | 6 | | 258 |
| CCGCACCTTCTCCACCAGGT | 267 | 2634 | 2653 | 6 | | 259 |
| GCCGCACCTTCTCCACCAGG | 268 | 2635 | 2654 | 6 | | 260 |
| CGCCGCACCTTCTCCACCAG | 269 | 2636 | 2655 | 6 | | 261 |
| CGCGCCGCACCTTCTCCACC | 270 | 2638 | 2657 | 6 | | 262 |
| TCGCGCCGCACCTTCTCCAC | 271 | 2639 | 2658 | 6 | | 263 |
| CTCGCGCCGCACCTTCTCCA | 272 | 2640 | 2659 | 6 | | 264 |
| CCTCGCGCCGCACCTTCTCC | 273 | 2641 | 2660 | 6 | | 265 |
| GCCTCGCGCCGCACCTTCTC | 274 | 2642 | 2661 | 6 | | 266 |
| GGCCTCGCGCCGCACCTTCT | 275 | 2643 | 2662 | 6 | | 267 |
| CGGCCTCGCGCCGCACCTTC | 276 | 2644 | 2663 | 6 | | 268 |
| TCGGCCTCGCGCCGCACCTT | 277 | 2645 | 2664 | 6 | | 269 |

TABLE 2-continued

| Table 2 Gapmer (oligonucleotide) to be tested having 2'-O-MOE group in wing nucleoside | | | | | | |
|---|---|---|---|---|---|---|
| ASO base sequence (DNA) 5' to 3' | ASO No. | Start position in SEQ ID NO: 471 | End position in SEQ ID NO: 471 | Target exon | ASO name | SEQ ID NO: |
| CTCGGCCTCGCGCCGCACCT | 278 | 2646 | 2665 | 6 | | 270 |
| GCTCGGCCTCGCGCCGCACC | 279 | 2647 | 2666 | 6 | | 271 |
| TGCTCGGCCTCGCGCCGCAC | 280 | 2648 | 2667 | 6 | | 272 |
| GCGCTCCTTTTCTTCGCGCG | 281 | 2673 | 2692 | 6 | | 273 |
| CGCGCTCCTTTTCTTCGCGC | 282 | 2674 | 2693 | 6 | | 274 |
| TCGCGCTCCTTTTCTTCGCG | 283 | 2675 | 2694 | 6 | | 275 |
| CTCGCGCTCCTTTTCTTCGC | 284 | 2676 | 2695 | 6 | | 276 |
| GCTCGCGCTCCTTTTCTTCG | 285 | 2677 | 2696 | 6 | | 277 |
| CGCTCGCGCTCCTTTTCTTC | 286 | 2678 | 2697 | 6 | | 278 |
| GCGCTCGCGCTCCTTTTCTT | 287 | 2679 | 2698 | 6 | | 279 |
| CGCGCTCGCGCTCCTTTTCT | 288 | 2680 | 2699 | 6 | | 280 |
| TCGCGCTCGCGCTCCTTTTC | 289 | 2681 | 2700 | 6 | | 281 |
| CTCGCGCTCGCGCTCCTTTT | 290 | 2682 | 2701 | 6 | | 282 |
| GCTCGCGCTCGCGCTCCTTT | 291 | 2683 | 2702 | 6 | | 283 |
| CGCTCGCGCTCGCGCTCCTT | 292 | 2684 | 2703 | 6 | | 284 |
| CCGCTCGCGCTCGCGCTCCT | 293 | 2685 | 2704 | 6 | | 285 |
| CCCGCTCGCGCTCGCGCTCC | 294 | 2686 | 2705 | 6 | | 286 |
| TCCCGCTCGCGCTCGCGCTC | 295 | 2687 | 2706 | 6 | | 287 |
| TTCCCGCTCGCGCTCGCGCT | 296 | 2688 | 2707 | 6 | | 288 |
| GTTCCCGCTCGCGCTCGCGC | 297 | 2689 | 2708 | 6 | | 289 |
| CGTTCCCGCTCGCGCTCGCG | 298 | 2690 | 2709 | 6 | | 290 |
| GCGTTCCCGCTCGCGCTCGC | 299 | 2691 | 2710 | 6 | | 291 |
| CGCGTTCCCGCTCGCGCTCG | 300 | 2692 | 2711 | 6 | | 292 |
| TCGCGTTCCCGCTCGCGCTC | 301 | 2693 | 2712 | 6 | | 293 |
| CTCGCGTTCCCGCTCGCGCT | 302 | 2694 | 2713 | 6 | | 294 |
| TCTCGCGTTCCCGCTCGCGC | 303 | 2695 | 2714 | 6 | | 295 |
| TTCTCGCGTTCCCGCTCGCG | 304 | 2696 | 2715 | 6 | | 296 |
| TTTCTCGCGTTCCCGCTCGC | 305 | 2697 | 2716 | 6 | | 297 |
| CTTTCTCGCGTTCCCGCTCG | 306 | 2698 | 2717 | 6 | | 298 |
| CTCGCGCTCCTTCTCGCGCT | 307 | 2724 | 2743 | 6 | | 299 |
| GCTCGCGCTCCTTCTCGCGC | 308 | 2725 | 2744 | 6 | | 300 |
| AAGCTCGCGCTCCTTCTCGC | 309 | 2727 | 2746 | 6 | | 301 |
| CAAGCTCGCGCTCCTTCTCG | 310 | 2728 | 2747 | 8 | | 302 |
| TTCAAGCTCGCGCTCCTTCT | 311 | 2730 | 2749 | 6 | | 303 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| GTTCAAGCTCGCGCTCCTTC | 312 | 2731 | 2750 | 6 | | 304 |
| CGTTCAAGCTCGCGCTCCTT | 313 | 2732 | 2751 | 6 | | 305 |
| GCGTTCAAGCTCGCGCTCCT | 314 | 2733 | 2752 | 6 | | 306 |
| CCGCACTGCCCGGTTCAAAT | 315 | 2827 | 2846 | 7 | | 307 |
| ACCGCACTGCCCGGTTCAAA | 316 | 2828 | 2847 | 7 | | 308 |
| CCACCGCACTGCCCGGTTCA | 317 | 2830 | 2849 | 7 | | 309 |
| GCCACCGCACTGCCCGGTTC | 318 | 2831 | 2850 | 7 | | 310 |
| TAGCCACCGCACTGCCCGGT | 319 | 2833 | 2852 | 7 | | 311 |
| GTAGCCACCGCACTGCCCGG | 320 | 2834 | 2853 | 7 | | 312 |
| CTGTAGCCACCGCACTGCCC | 321 | 2836 | 2855 | 7 | | 313 |
| ACTGTAGCCACCGCACTGCC | 322 | 2837 | 2856 | 7 | | 314 |
| CCCGGGTCCACTGCCCCCAG | 323 | 2963 | 2982 | 7 | | 315 |
| GTGCTGCCTCTCAGCTGCCA | 324 | 3303 | 3322 | 7 | | 316 |
| CGTGCTGCCTCTCAGCTGCC | 325 | 3304 | 3323 | 7 | | 317 |
| GCGTGCTGCCTCTCAGCTGC | 326 | 3305 | 3324 | 7 | | 318 |
| CTGCGTGCTGCCTCTCAGCT | 327 | 3307 | 3326 | 7 | | 319 |
| TCTGCGTGCTGCCTCTCAGC | 328 | 3308 | 3327 | 7 | | 320 |
| TTCTGCGTGCTGCCTCTCAG | 329 | 3309 | 3328 | 7 | | 321 |
| TTTCTGCGTGCTGCCTCTCA | 330 | 3310 | 3329 | 7 | | 322 |
| CTTTCTGCGTGCTGCCTCTC | 331 | 3311 | 3330 | 7 | | 323 |
| CCTTTCTGCGTGCTGCCTCT | 332 | 3312 | 3331 | 7 | | 324 |
| CCCTTTCTGCGTGCTGCCTC | 333 | 3313 | 3332 | 7 | | 325 |
| ACCCTTTCTGCGTGCTGCCT | 334 | 3314 | 3333 | 7 | | 326 |
| CACCCTTTCTGCGTGCTGCC | 335 | 3315 | 3334 | 7 | | 327 |
| CCACCCTTTCTGCGTGCTGC | 336 | 3316 | 3335 | 7 | | 328 |
| GCCACCCTTTCTGCGTGCTG | 337 | 3317 | 3336 | 7 | | 329 |
| CGCCACCCTTTCTGCGTGCT | 338 | 3318 | 3337 | 7 | | 330 |
| CCGCCACCCTTTCTGCGTGC | 339 | 3319 | 3338 | 7 | | 331 |
| GCCGCCACCCTTTCTGCGTG | 340 | 3320 | 3339 | 7 | | 332 |
| GGCCGCCACCCTTTCTGCGT | 341 | 3321 | 3340 | 7 | | 333 |
| GGGCCGCCACCCTTTCTGCG | 342 | 3322 | 3341 | 7 | | 334 |
| AGGGCCGCCACCCTTTCTGC | 343 | 3323 | 3342 | 7 | | 335 |
| CAGGGCCGCCACCCTTTCTG | 344 | 3324 | 3343 | 7 | | 336 |
| GGCAGAAAGGGAGGCCGGCA | 345 | 3618 | 3637 | 9 | | 337 |

TABLE 2-continued

| Table 2 Gapmer (oligonucleotide) to be tested having 2'-O-MOE group in wing nucleoside | | | | | | |
|---|---|---|---|---|---|---|
| ASO base sequence (DNA) 5' to 3' | ASO No. | Start position in SEQ ID NO: 471 | End position in SEQ ID NO: 471 | Target exon | ASO name | SEQ ID NO: |
| GGGCAGAAAGGGAGGCCGGC | 346 | 3619 | 3638 | 9 | | 338 |
| GGGGCAGAAAGGGAGGCCGG | 347 | 3620 | 3639 | 9 | | 339 |
| GGGGGCAGAAAGGGAGGCCG | 348 | 3621 | 3640 | 9 | | 340 |
| TCGGGGCAGAAAGGGAGGCC | 349 | 3622 | 3641 | 9 | | 341 |
| ATCGGGGCAGAAAGGGAGGC | 350 | 3623 | 3642 | 9 | | 342 |
| CATCGGGGCAGAAAGGGAGG | 351 | 3624 | 3643 | 9 | | 343 |
| ACATCGGGGCAGAAAGGGAG | 352 | 3625 | 3644 | 9 | | 344 |
| GACATCGGGGCAGAAAGGGA | 353 | 3626 | 3645 | 9 | | 345 |
| TGACATCGGGGCAGAAAGGG | 354 | 3627 | 3646 | 9 | | 346 |
| CTGACATCGGGGCAGAAAGG | 355 | 3628 | 3647 | 9 | | 347 |
| GCTGACATCGGGGCAGAAAG | 356 | 3629 | 3648 | 9 | | 348 |
| TGCTGACATCGGGGCAGAAA | 357 | 3630 | 3649 | 9 | | 349 |
| GCTGCTGACATCGGGGCAGA | 358 | 3632 | 3651 | 9 | | 350 |
| AGCTGCTGACATCGGGGCAG | 359 | 3633 | 3652 | 9 | | 351 |
| GAGCTGCTGACATCGGGGCA | 360 | 3634 | 3653 | 9 | | 352 |
| ATGAGCTGCTGACATCGGGG | 361 | 3636 | 3655 | 9 | | 353 |
| GATGAGCTGCTGACATCGGG | 362 | 3637 | 3656 | 9 | | 354 |
| TGATGAGCTGCTGACATCGG | 363 | 3638 | 3657 | 9 | | 355 |
| GCTGATGAGCTGCTGACATC | 364 | 3640 | 3659 | 9 | | 356 |
| AGCTGATGAGCTGCTGACAT | 365 | 3641 | 3660 | 9 | | 357 |
| CAGCTGATGAGCTGCTGACA | 366 | 3642 | 3661 | 9 | | 358 |
| GCAGCTGATGAGCTGCTGAC | 367 | 3643 | 3662 | 9 | | 359 |
| TGCAGCTGATGAGCTGCTGA | 368 | 3644 | 3663 | 9 | | 360 |
| CTGCAGCTGATGAGCTGCTG | 369 | 3645 | 3664 | 9 | | 361 |
| CCTGCAGCTGATGAGCTGCT | 370 | 3646 | 3665 | 9 | | 362 |
| GCCTGCAGCTGATGAGCTGC | 371 | 3647 | 3666 | 9 | | 363 |
| GGCCTGCAGCTGATGAGCTG | 372 | 3648 | 3667 | 9 | | 364 |
| TGGCCTGCAGCTGATGAGCT | 373 | 3649 | 3668 | 9 | | 365 |
| ATGGCCTGCAGCTGATGAGC | 374 | 3650 | 3669 | 9 | | 366 |
| CATGGCCTGCAGCTGATGAG | 375 | 3651 | 3670 | 9 | | 367 |
| GCATGGCCTGCAGCTGATGA | 376 | 3652 | 3671 | 9 | | 368 |
| TGCATGGCCTGCAGCTGATG | 377 | 3653 | 3672 | 9 | | 369 |
| CAGCTCAGCTGACTGTGCGT | 378 | 3672 | 3691 | 9 | | 370 |
| GCAGCTCAGCTGACTGTGCG | 379 | 3673 | 3692 | 9 | | 371 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| TGCAGCTCAGCTGACTGTGC | 380 | 3674 | 3693 | 9 | | 372 |
| CTGCAGCTCAGCTGACTGTG | 381 | 3675 | 3694 | 9 | | 373 |
| GCTGCAGCTCAGCTGACTGT | 382 | 3676 | 3695 | 9 | | 374 |
| CGCTGCAGCTCAGCTGACTG | 383 | 3677 | 3696 | 9 | | 375 |
| GCGCTGCAGCTCAGCTGACT | 384 | 3678 | 3697 | 9 | | 376 |
| AGCGCTGCAGCTCAGCTGAC | 385 | 3679 | 3698 | 9 | | 377 |
| AAGCGCTGCAGCTCAGCTGA | 386 | 3680 | 3699 | 9 | | 378 |
| CAAGCGCTGCAGCTCAGCTG | 387 | 3681 | 3700 | 9 | | 379 |
| CCAAGCGCTGCAGCTCAGCT | 388 | 3682 | 3701 | 9 | | 380 |
| GCCAAGCGCTGCAGCTCAGC | 389 | 3683 | 3702 | 9 | | 381 |
| CGCCAAGCGCTGCAGCTCAG | 390 | 3684 | 3703 | 9 | | 382 |
| GOGCCAAGCGCTGCAGCTCA | 391 | 3685 | 3704 | 9 | | 383 |
| AGCGCCAAGCGCTGCAGCTC | 392 | 3686 | 3705 | 9 | | 384 |
| CCAGCGCCAAGCGCTGCAGC | 393 | 3688 | 3707 | 9 | | 385 |
| TCCAGCGCCAAGCGCTGCAG | 394 | 3689 | 3708 | 9 | | 386 |
| TTCCAGCGCCAAGCGCTGCA | 395 | 3690 | 3709 | 9 | | 387 |
| TGTTCCAGCGCCAAGCGCTG | 396 | 3692 | 3711 | 9 | | 388 |
| CTGTTCCAGCGCCAAGCGCT | 397 | 3693 | 3712 | 9 | | 389 |
| GCTGTTCCAGCGCCAAGCGC | 398 | 3694 | 3713 | 9 | | 390 |
| CTGCTGTTCCAGCGCCAAGC | 399 | 3696 | 3715 | 9 | | 391 |
| GCTGCTGTTCCAGCGCCAAG | 400 | 3697 | 3716 | 9 | | 392 |
| TGCTGCTGTTCCAGCGCCAA | 401 | 3698 | 3717 | 9 | | 393 |
| CTGCTGCTGTTCCAGCGCCA | 402 | 3699 | 3718 | 9 | | 394 |
| ACTGCTGCTGTTCCAGCGCC | 403 | 3700 | 3719 | 9 | | 395 |
| CACTGCTGCTGTTCCAGCGC | 404 | 3701 | 3720 | 9 | | 396 |
| CCACTGCTGCTGTTCCAGCG | 405 | 3702 | 3721 | 9 | | 397 |
| GCCACTGCTGCTGTTCCAGC | 406 | 3703 | 3722 | 9 | | 398 |
| AGCCACTGCTGCTGITCCAG | 407 | 3704 | 3723 | 9 | | 399 |
| CAGCCACTGCTGCTGTTCCA | 408 | 3705 | 3724 | 9 | | 400 |
| GCAGCCACTGCTGCTGTTCC | 409 | 3706 | 3725 | 9 | | 401 |
| TGCAGCCACTGCTGCTGTTC | 410 | 3707 | 3726 | 9 | | 402 |
| ATGCAGCCACTGCTGCTGTT | 411 | 3708 | 3727 | 9 | | 403 |
| GGCAGCGGCACACTGTGCAG | 412 | 3740 | 3759 | 9 | | 404 |
| AGGCAGCGGCACACTGTGCA | 413 | 3741 | 3760 | 9 | | 405 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| CAGGCAGCGGCACACTGTGC | 414 | 3742 | 3761 | 9 | | 406 |
| GCAGGCAGCGGCACACTGTG | 415 | 3743 | 3762 | 9 | | 407 |
| GGCAGGCAGCGGCACACTGT | 416 | 3744 | 3763 | 9 | | 408 |
| TTGGCCTTCTGTCTGTCCCT | 417 | 3965 | 3984 | 10 | | 409 |
| CTTGGCCTTCTGTCTGTCCC | 418 | 3966 | 3985 | 10 | | 410 |
| CCTTGGCCTTCTGTCTGTCC | 419 | 3967 | 3986 | 10 | | 411 |
| GCCTTGGCCTTCTGTCTGTC | 420 | 3968 | 3987 | 10 | | 412 |
| GGCCTTGGCCTTCTGTCTGT | 421 | 3969 | 3988 | 10 | | 413 |
| GGGCCTTGGCCTTCTGTCTG | 422 | 3970 | 3989 | 10 | | 414 |
| CGGGCCTTGGCCTTCTGTCT | 423 | 3971 | 3990 | 10 | | 415 |
| TCGGGCCTTGGCCTTCTGTC | 424 | 3972 | 3991 | 10 | | 416 |
| ATCGGGCCTTGGCCTTCTGT | 425 | 3973 | 3992 | 10 | | 417 |
| CATCGGGCCTTGGCCTTCTG | 426 | 3974 | 3993 | 10 | | 418 |
| ACATCGGGCCTTGGCCTTCT | 427 | 3975 | 3994 | 10 | | 419 |
| CACATCGGGCCTTGGCCTTC | 428 | 3976 | 3995 | 10 | | 420 |
| CCACATCGGGCCTTGGCCTT | 429 | 3977 | 3996 | 10 | | 421 |
| ACCACATCGGGCCTTGGCCT | 430 | 3978 | 3997 | 10 | | 422 |
| CACCACATCGGGCCTTGGCC | 431 | 3979 | 3998 | 10 | | 423 |
| CACACCACATCGGGCCTTGG | 432 | 3981 | 4000 | 10 | | 424 |
| GCACACCACATCGGGCCTTG | 433 | 3982 | 4001 | 10 | | 425 |
| TGCACACCACATCGGGCCTT | 434 | 3983 | 4002 | 10 | | 426 |
| TCTGCACACCACATCGGGCC | 435 | 3985 | 4004 | 10 | | 427 |
| CTCTGCACACCACATCGGGC | 436 | 3986 | 4005 | 10 | | 428 |
| CCTCTGCACACCACATCGGG | 437 | 3987 | 4006 | 10 | | 429 |
| CACCTCTGCACACCACATCG | 438 | 3989 | 4008 | 10 | | 430 |
| CCACCTCTGCACACCACATC | 439 | 3990 | 4009 | 10 | | 431 |
| CCCACCTCTGCACACCACAT | 440 | 3991 | 4010 | 10 | | 432 |
| CCCCACCTCTGCACACCACA | 441 | 3992 | 4011 | 10 | | 433 |
| TCCCCACCTCTGCACACCAC | 442 | 3993 | 4012 | 10 | | 434 |
| CTCCCCACCTCTGCACACCA | 443 | 3994 | 4013 | 10 | | 435 |
| CCTCCCCACCTCTGCACACC | 444 | 3995 | 4014 | 10 | | 436 |
| ACCTCCCCACCTCTGCACAC | 445 | 3996 | 4015 | 10 | | 437 |
| CACCTCCCCACCTCTGCACA | 446 | 3997 | 4016 | 10 | | 438 |
| CCACCTCCCCACCTCTGCAC | 447 | 3998 | 4017 | 10 | | 439 |

TABLE 2-continued

Table 2 Gapmer (oligonucleotide) to be tested having 2'-O-MOE group in wing nucleoside

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| AGGGGCAGGGGTGGCACACG | 448 | 4181 | 4200 | 10 | | 440 |
| GAGGGGCAGGGGTGGCACAC | 449 | 4182 | 4201 | 10 | | 441 |
| GGAGGGGCAGGGGTGGCACA | 450 | 4183 | 4202 | 10 | | 442 |
| GGGAGGGGCAGGGGTGGCAC | 451 | 4184 | 4203 | 10 | | 443 |
| GGGGAGGGGCAGGGGTGGCA | 452 | 4185 | 4204 | 10 | | 444 |
| CGGGGAGGGGCAGGGGTGGC | 453 | 4186 | 4205 | 10 | | 445 |
| TCGGGGAGGGGCAGGGGTGG | 454 | 4187 | 4206 | 10 | | 446 |
| ATCGGGGAGGGGCAGGGGTG | 455 | 4188 | 4207 | 10 | | 447 |
| GATCGGGGAGGGGCAGGGGT | 456 | 4189 | 4208 | 10 | | 448 |
| GGATCGGGGAGGGGCAGGGG | 457 | 4190 | 4209 | 10 | | 449 |
| GGGATCGGGGAGGGGCAGGG | 458 | 4191 | 4210 | 10 | | 450 |
| AGGGATCGGGGAGGGGCAGG | 459 | 4192 | 4211 | 10 | | 451 |
| CAGGGATCGGGGAGGGGCAG | 460 | 4193 | 4212 | 10 | | 452 |
| ACAGGGATCGGGGAGGGGCA | 461 | 4194 | 4213 | 10 | | 453 |
| CACAGGGATCGGGGAGGGGC | 462 | 4195 | 4214 | 10 | | 454 |
| ACACAGGGATCGGGGAGGGG | 463 | 4196 | 4215 | 10 | | 455 |
| CACACAGGGATCGGGGAGGG | 464 | 4197 | 4216 | 10 | | 456 |
| GCACACAGGGATCGGGGAGG | 465 | 4198 | 4217 | 10 | | 457 |
| CGCACACAGGGATCGGGGAG | 466 | 4199 | 4218 | 10 | | 458 |
| GCGCACACAGGGATCGGGGA | 467 | 4200 | 4219 | 10 | | 459 |
| CGCGCACACAGGGATCGGGG | 468 | 4201 | 4220 | 10 | | 460 |
| GCGCGCACACAGGGATCGGG | 469 | 4202 | 4221 | 10 | | 461 |
| GGCGCGCACACAGGGATCGG | 470 | 4203 | 4222 | 10 | | 462 |
| GGGGCGCGCACACAGGGATC | 471 | 4205 | 4224 | 10 | | 463 |
| GGGGGCGCGCACACAGGGAT | 472 | 4206 | 4225 | 10 | | 464 |

In Table 3, all oligonucleotides are 5-10-5 gapmers having a 2'-O-MOE group, bonds between nucleosides in the 5' wing region and the 3' wing region are phosphorothioate (P═S) or phosphodiester (P═O), and bonds between nucleosides in the gap region are all phosphorothioate (P═S). In Table 3, each phosphodiester (P═O) bond is shown as "^". Besides, C in the gap region and the wing region is actually methyl C, and T in the wing region is actually T.

TABLE 3

| Table 3 Gapmer (oligonucleotide) to be tested containing phosphodiester bond in bonds between wing nucleosides | | | | | | |
|---|---|---|---|---|---|---|
| ASO base sequence (DNA) 5' to 3' | ASO No. | Start position in SEQ ID NO: 471 | End position in SEQ ID NO: 471 | Target exon | ASO name | SEQ ID NO: |
| AG^A^G^ACCTGGTCCAAG^A^T^TC | 473 | 4043 | 4062 | 10 | DRA-274 | 472 |
| AG^A^GACGTGGTCCAAGA^T^TC | 474 | 4043 | 4062 | 10 | DRA-275 | 472 |
| AG^AG^ACCTGGTCCAAG^AT^TC | 475 | 4043 | 4062 | 10 | DRA-276 | 472 |
| AGA^G^ACCTGGTCCAAG^A^TTC | 476 | 4043 | 4062 | 10 | DRA-277 | 472 |
| AG^AGACCTGGTCCAAGAT^TC | 477 | 4043 | 4062 | 10 | DRA-278 | 472 |
| AGA^GACCTGGTCCAAGA^TTC | 478 | 4043 | 4062 | 10 | DRA-279 | 472 |
| AGAG^ACCTGGTCCAAG^ATTC | 479 | 4043 | 4062 | 10 | DRA-280 | 472 |
| GA^T^G^GGCATTGCTGTT^G^G^CT | 480 | 1597 | 1616 | 5 | DRA-281 | 177 |
| GA^T^AGGGCATTGCTGTTG^G^CT | 481 | 1597 | 1616 | 5 | DRA-282 | 177 |
| GA^TG^GGCATTGCTGTT^GG^CT | 482 | 1597 | 1616 | 5 | DRA-283 | 177 |
| GAT^GAGGCATTGCTGTT^G^G^CT | 483 | 1597 | 1616 | 5 | DRA-284 | 177 |
| GA^TGGGCATTGCTGTTG^GCT | 484 | 1597 | 1616 | 5 | DRA-285 | 177 |
| GAT^GGGCATTGCTGTTG^GCT | 485 | 1597 | 1816 | 5 | DRA-286 | 177 |
| GATG^GGCATTGCTGTT^GGCT | 486 | 1597 | 1616 | 5 | DRA-287 | 177 |
| TC^C^T^TCTCGCGCTCGC^G^C^TC | 487 | 2717 | 2736 | 5 | DRA-298 | 133 |
| TC^C^TTCTCGCGCTCGCG^C^TC | 488 | 2717 | 2736 | 8 | DRA-308 | 133 |
| TC^CT^TCTCGCGCTCGCAGC^TC | 489 | 2717 | 2736 | 8 | DRA-299 | 133 |
| TCC^T^TCTCGCGCTCGC^G^CTC | 490 | 2717 | 2736 | 8 | DRA-309 | 133 |
| TC^CTTCTCGCGCTCGCGC^TC | 491 | 2717 | 2736 | 8 | DRA-310 | 133 |
| TCC^TTCTCGCGCTCGCG^CTC | 492 | 2717 | 2736 | 8 | DRA-311 | 133 |
| TCCT^TCTCGCGCTCGC^GCTC | 493 | 2717 | 2736 | 8 | DRA-312 | 133 |
| CT^C^G^CGCTCGCGCTCT^T^T^CT | 494 | 2712 | 2731 | 8 | DRA-300 | 196 |
| CT^CG^CGCTCGCGCTCT^TT^CT | 495 | 2712 | 2731 | 6 | DRA-301 | 196 |
| GC^T^G^TTGGCTAAGAGG^C^G^GC | 496 | 1587 | 1606 | 5 | DRA-302 | 170 |

^: Phosphodiester bond

In Table 4, oligonucleotides are all 5-10-5 gapmers having a 2'-O-MOE group, bonds between nucleosides in the 5' wing region and the 3' wing region are phosphorothioate (P═S) or phosphodiester (P═O), and bonds between nucleosides in the gap region are all phosphorothioate (P═S). In Table 4, each phosphodiester (P═O) bond is shown as "^". Besides, C in the gap region and the wing region is actually methyl C, T in the wing region is actually T, and underlined bases of the 3' wing region are bases different from those of SEQ ID NO: 196.

[Table 4]

TABLE 4

Table 4 Gapmer (oligonucleotide) to be tested different in one nucleotide in 3' wing from SEQ ID NO: 196

| ASO base sequence (DNA) 5' to 3' | ASO No. | Start position in SEQ ID NO: 471 | End position in SEQ ID NO: 471 | Target exon | ASO name | SEQ ID NO: |
|---|---|---|---|---|---|---|
| CTCGCGCTCGC GCTCCTTCT | 497 | 2712 | 2731 | 10 | DRA-303 | 473 |
| CT^C^G^CGCTC GCGCTCC^T^T^CT | 498 | 2712 | 2731 | 10 | DRA-304 | 473 |
| CT^CG^CGCTCG CGCTCC^TT^CT | 499 | 2712 | 2731 | 10 | DRA-306 | 473 |

^: Phosphodiester bond
underlined: bases different from SEQ ID NO: 196

[Test Example 1] Measurement of ATN-1 Gene Knockdown Activity (Inhibitory Activity) of Gapmer Using A204 Human Rhabdomyosarcoma Cell Line Into $3.0\times10^5$ A204 cells (obtained from ATCC), each of gapmers to be tested shown in Tables 1 and 2, or a positive control gapmer was introduced in a concentration of 1 μM or 2 μM with 4D-Nucleofector™ using SF Cell Line 4D-Nucleotector™ X KitS in accordance with the protocol attached to the kit. DS-130 was used as the program. After the introduction, the cells were cultured overnight in a 10% fetal bovine serum (FBS) (NICHIREI) and McCoy's 5A Medium (SIGMA) containing 1 mM L-glutamine (Gibco) under conditions of 37° C. and 5% $CO_2$. As the positive control gapmer, OMe-6 (5'-AGAGACCTGGTCCAAGATTC-3', SEQ ID NO: 472) having a 2'-OMe group in a nucleoside of the wing, or NRH-71 (5'-AGAGACCTGGTCCAAGATTC-3', SEQ ID NO: 472) having a 2'-O-MOE group in a nucleoside of the wing, both of which had been confirmed to have activity through a preliminary test (data not shown), was used. Both the oligonucleotides were 5-10-5 gapmers, and bonds between nucleosides were all phosphorothioate (P═S). Besides, in OMe-6, T (thymine) in the wing region was actually U (uracil). In NRH-71, C (cytosine) in the gap region and the wing region was actually methyl C, and T in the wing region was actually T. These positive control gapmers were synthesized in the same manner as the gapmers to be tested. On the next day, after washing the resultant cells with PBS (Nacalai Tesque, Inc.), RA1 (Takara Bio Inc.) containing 1% 2-mercaptoethanol (Nacalai Tesque, Inc.) was added thereto to dissolve the cells, which were collected on NucleoSpin® Filter (Takara Bio Inc.). After removing an insoluble fraction by centrifugation, total RNA was extracted in accordance with the protocol attached to NucleoSpin® RNA (Takara Bio Inc.). The concentration of the extracted total RNA was measured with NanoDrop (Thermo Fisher). 200 ng of the extracted total RNA was subjected to a reverse transcription (RT) reaction with High Capacity cDNA Reverse Transcription Kit (Applied Biosystems) and a random primer attached to the kit. Specifically, in accordance with the protocol attached to the kit, a reaction solution was prepared. TaKaRa PCR Thermal Cycler Dice Touch (Takara Bio Inc.) was used as the thermal cycler. The program of the RT reaction used was as follows.

25° C., 10 minutes: primer annealing

37° C., 120 minutes: reverse transcription reaction

85° C., 5 minutes: reverse transcriptase inactivation

Thereafter, qPCR was performed with Fast SYBR Green Master Mix (Thermo Fisher Scientific) using the RT reaction solution as a template, and the ATN1 RNA expression level endogenously expressed in the A204 cells was measured. In the qPCR reaction, sequences of 2 portions in ATN1 (exon 4 to exon 5, and exon 6 to exon 7) were used as templates. Specifically, in accordance with the protocol attached to the kit, a reaction solution was prepared. For the qPCR, QuantStudio 6 Flex Real-Time PCR System (Applied Biosystems) was used. The program of the qPCR used was as follows.

50° C., 2 minutes; and 95° C., 10 minutes: polymerase activation, cDNA thermal denaturation

[95° C., 15 seconds; and 60° C., 1 minute]×40 cycles: PCR Amplification

95° C., 15 seconds; and 60° C., 1 minute to 95° C., 15 seconds (Melting Curve 0.05° C./s): melting curve analysis Primers used in the detection of the ATN1 RNA are shown in Table 4. The ATN1 RNA expression level was corrected with β-actin RNA expression level of house keeping gene. Primers used in the detection of β-actin RNA are shown in Table 4. An inhibition ratio of ATN1 expression of the gampers to the ATN1 RNA expression level of cells having been subjected to the introduction operation only with 4D-Nucleofector™ without adding the gapmers was calculated based on a ratio of the ATN1 RNA expression level obtained by introducing the gapmers to be tested, and thus, the inhibitory activity of the gapmers to be tested was analyzed. Results are shown in Tables 5 to 9.

TABLE 5-1

Table 5-1 Endogenous ATN1 Primer used for RNA detection and recognized exon site

| | Primer set for detection | | | |
|---|---|---|---|---|
| Recognized exon | Sense primer 5' to 3' | SEQ ID NO: | Reverse primer 5' to 3' | SEQ ID NO: |
| exon4-5 | TCAACAAGCA GGGTCGGAGT | 465 | CTTCGGTTGTC CTGGTCGATA | 467 |
| exon6-7 | TTGAACGCAG CGTGAAGTTG | 466 | TTGCGATTGCC AGGAGACAT | 468 |

TABLE 5-2

Table 5-2 β-Actin used as gene for correction Primer used for RNA detection

| | Primer set for detection | | | |
|---|---|---|---|---|
| Gene for correction | Sense primer 5' to 3' | SEQ ID NO: | Reverse primer 5' to 3' | SEQ ID NO: |
| β-actin | GAAGATCAAGA TCATTGCTCCT | 469 | TACTCCTGCT TGCTGATCCA | 470 |

TABLE 6

Table 6 Ratio of ATN-1 gene expression level in A204 cell administered with gapmer (2.0 μM) having 2'-OMe group in wing nucleoside

| ASO No. | mRNA expression level (exon4-5) | Ratio of mRNA expression level/ OMe-6 (exon4-5) | mRNA expression level (exon6-7) | Ratio of mRNA expression level/ OMe-6 (exon6-7) | Average of ratio of mRNA expression level | SEQ ID NO: |
|---|---|---|---|---|---|---|
| 1 | 0.94 | 2.09 | 1.00 | 2.29 | 2.19 | 1 |
| 2 | 0.97 | 2.15 | 1.00 | 2.30 | 2.23 | 2 |
| 3 | 0.75 | 1.64 | 0.76 | 1.61 | 1.62 | 3 |
| 4 | 0.44 | 1.27 | 0.47 | 1.28 | 1.27 | 4 |
| 6 | 0.61 | 1.56 | 0.69 | 1.60 | 1.58 | 6 |
| 7 | 0.11 | 0.26 | 0.14 | 0.30 | 0.28 | 7 |
| 8 | 0.66 | 1.90 | 0.67 | 1.80 | 1.85 | 8 |
| 9 | 0.33 | 0.73 | 0.40 | 0.80 | 0.76 | 9 |
| 10 | 0.20 | 0.47 | 0.24 | 0.52 | 0.49 | 10 |
| 11 | 0.30 | 0.77 | 0.34 | 0.78 | 0.77 | 11 |
| 12 | 0.15 | 0.35 | 0.18 | 0.39 | 0.37 | 12 |
| 13 | 0.18 | 0.46 | 0.17 | 0.39 | 0.42 | 13 |
| 14 | 0.75 | 1.59 | 0.83 | 1.69 | 1.64 | 14 |
| 15 | 0.62 | 1.37 | 0.53 | 1.23 | 1.30 | 15 |
| 16 | 0.47 | 1.03 | 0.40 | 0.93 | 0.98 | 16 |
| 17 | 0.39 | 0.71 | 0.40 | 0.80 | 0.76 | 17 |
| 18 | 0.72 | 1.61 | 0.67 | 1.54 | 1.57 | 18 |
| 19 | 0.74 | 1.33 | 0.77 | 1.37 | 1.35 | 19 |
| 20 | 0.70 | 1.01 | 0.72 | 1.27 | 1.14 | 20 |
| 21 | 0.71 | 1.50 | 0.84 | 1.71 | 1.60 | 21 |
| 22 | 0.29 | 0.82 | 0.29 | 0.77 | 0.80 | 22 |
| 23 | 0.78 | 1.65 | 0.85 | 1.73 | 1.69 | 23 |
| 24 | 0.52 | 1.09 | 0.62 | 1.26 | 1.17 | 24 |
| 25 | 0.16 | 0.41 | 0.17 | 0.38 | 0.40 | 25 |
| 26 | 0.59 | 1.50 | 0.63 | 1.44 | 1.47 | 26 |
| 27 | 0.18 | 0.42 | 0.18 | 0.39 | 0.41 | 27 |
| 28 | 0.19 | 0.49 | 0.21 | 0.48 | 0.49 | 28 |
| 29 | 0.39 | 1.10 | 0.47 | 1.27 | 1.19 | 29 |
| 30 | 0.11 | 0.32 | 0.13 | 0.34 | 0.33 | 30 |
| 31 | 0.43 | 0.94 | 0.49 | 1.02 | 0.98 | 31 |
| 32 | 0.79 | 2.28 | 0.76 | 2.05 | 2.16 | 32 |
| 33 | 0.69 | 1.51 | 0.71 | 1.49 | 1.50 | 33 |
| 34 | 0.79 | 1.72 | 0.92 | 1.93 | 1.82 | 34 |
| 35 | 0.79 | 1.72 | 0.89 | 1.87 | 1.80 | 35 |
| 36 | 0.84 | 1.82 | 0.80 | 1.68 | 1.75 | 36 |
| 37 | 0.74 | 1.62 | 0.77 | 1.62 | 1.62 | 37 |
| 39 | 0.75 | 1.63 | 0.84 | 1.76 | 1.69 | 39 |
| 40 | 0.82 | 2.35 | 0.80 | 2.15 | 2.25 | 40 |
| 41 | 0.64 | 1.39 | 0.55 | 1.15 | 1.27 | 43 |
| 42 | 0.58 | 1.66 | 0.53 | 1.43 | 1.54 | 42 |
| 43 | 0.80 | 1.75 | 0.90 | 1.90 | 1.82 | 43 |
| 44 | 0.61 | 1.33 | 0.63 | 1.47 | 1.40 | 44 |
| 45 | 0.38 | 1.09 | 0.36 | 0.96 | 1.03 | 45 |
| 46 | 0.92 | 2.00 | 0.92 | 2.14 | 2.07 | 46 |
| 47 | 0.86 | 1.87 | 0.86 | 2.00 | 1.94 | 47 |
| 48 | 0.38 | 1.09 | 0.44 | 1.18 | 1.13 | 48 |
| 49 | 0.56 | 1.21 | 0.53 | 1.23 | 1.22 | 49 |
| 50 | 0.72 | 1.56 | 0.69 | 1.60 | 1.58 | 50 |
| 52 | 0.44 | 1.03 | 0.47 | 1.08 | 1.06 | 52 |
| 53 | 0.80 | 2.03 | 0.83 | 1.90 | 1.97 | 53 |
| 54 | 0.75 | 1.63 | 0.78 | 1.81 | 1.72 | 54 |
| 55 | 0.77 | 1.67 | 0.76 | 1.78 | 1.72 | 55 |
| 56 | 0.62 | 1.34 | 0.63 | 1.46 | 1.40 | 56 |
| 57 | 0.98 | 2.14 | 1.00 | 2.47 | 2.30 | 57 |
| 58 | 0.68 | 1.26 | 0.70 | 1.21 | 1.23 | 58 |

TABLE 7

Table 7 Ratio of ATN-1 gene expression level in A204 cell administered with gapmer (1.0 μM) having 2'-OMe group in wing nucleoside

| ASO No. | mRNA expression level (exon4-5) | Ratio of mRNA expression level/ OMe-6 (exon4-5) | mRNA expression level (exon6-7) | Ratio of mRNA expression level/ OMe-6 (exon6-7) | Average of ratio of mRNA expression level | SEQ ID NO: |
|---|---|---|---|---|---|---|
| 1 | 0.91 | 1.25 | 1.00 | 1.21 | 1.23 | 1 |
| 2 | 0.88 | 1.21 | 1.00 | 1.22 | 1.21 | 2 |
| 7 | 0.15 | 0.30 | 0.15 | 0.29 | 0.30 | 7 |
| 10 | 0.23 | 0.46 | 0.25 | 0.49 | 0.47 | 10 |
| 12 | 0.21 | 0.42 | 0.21 | 0.40 | 0.41 | 12 |
| 27 | 0.25 | 0.48 | 0.25 | 0.48 | 0.48 | 27 |

TABLE 8

Ratio of ATN-1 gene expression level in A204 cell administered with gapmer (2.0 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 59 | 1.00 | 3.18 | 0.88 | 2.44 | 2.81 | 59 |
| 60 | 0.23 | 0.46 | 0.23 | 0.58 | 0.52 | 60 |
| 61 | 0.04 | 0.11 | 0.07 | 0.20 | 0.15 | 61 |
| 64 | 0.04 | 0.12 | 0.13 | 0.35 | 0.23 | 64 |
| 65 | 0.11 | 0.34 | 0.22 | 0.62 | 0.48 | 65 |
| 69 | 0.05 | 0.18 | 0.04 | 0.24 | 0.21 | 69 |
| 71 | 0.11 | 0.32 | 0.12 | 0.34 | 0.33 | 71 |
| 72 | 0.15 | 0.32 | 0.13 | 0.31 | 0.31 | 72 |
| 88 | 0.03 | 0.09 | 0.03 | 0.16 | 0.12 | 84 |
| 89 | 0.06 | 0.19 | 0.06 | 0.33 | 0.26 | 13 |
| 93 | 0.63 | 1.33 | 0.64 | 1.50 | 1.42 | 88 |
| 94 | 0.87 | 1.77 | 0.89 | 2.27 | 2.02 | 89 |
| 95 | 0.12 | 0.26 | 0.14 | 0.33 | 0.30 | 90 |
| 96 | 0.16 | 0.33 | 0.14 | 0.32 | 0.32 | 91 |
| 97 | 0.35 | 0.75 | 0.23 | 0.55 | 0.65 | 92 |
| 98 | 0.67 | 1.36 | 0.71 | 1.82 | 1.59 | 93 |
| 99 | 0.65 | 1.31 | 0.63 | 1.62 | 1.46 | 94 |
| 105 | 0.09 | 0.19 | 0.09 | 0.23 | 0.21 | 100 |
| 108 | 0.45 | 0.92 | 0.43 | 1.09 | 1.00 | 103 |
| 109 | 0.07 | 0.24 | 0.06 | 0.35 | 0.29 | 104 |
| 110 | 0.10 | 0.34 | 0.09 | 0.51 | 0.43 | 105 |
| 120 | 1.00 | 2.06 | 0.89 | 2.26 | 2.16 | 115 |
| 121 | 0.22 | 0.45 | 0.21 | 0.53 | 0.49 | 116 |
| 127 | 0.44 | 0.89 | 0.41 | 1.06 | 0.97 | 120 |
| 128 | 0.35 | 0.83 | 0.39 | 0.93 | 0.88 | 121 |
| 129 | 0.30 | 0.71 | 0.34 | 0.80 | 0.75 | 122 |
| 130 | 0.53 | 1.28 | 0.56 | 1.33 | 1.31 | 123 |
| 131 | 0.89 | 2.14 | 0.76 | 1.81 | 1.98 | 124 |
| 132 | 0.42 | 1.00 | 0.48 | 1.13 | 1.07 | 125 |
| 133 | 0.23 | 0.56 | 0.24 | 0.57 | 0.56 | 126 |
| 134 | 0.43 | 1.04 | 0.43 | 1.02 | 1.03 | 127 |
| 139 | 0.13 | 0.31 | 0.10 | 0.24 | 0.27 | 132 |
| 144 | 0.23 | 0.56 | 0.06 | 0.14 | 0.35 | 137 |
| 145 | 0.65 | 1.55 | 0.56 | 1.34 | 1.44 | 138 |
| 150 | 0.14 | 0.35 | 0.05 | 0.12 | 0.24 | 143 |
| 152 | 0.23 | 0.56 | 0.23 | 0.53 | 0.55 | 145 |
| 153 | 0.17 | 0.41 | 0.23 | 0.54 | 0.48 | 146 |
| 154 | 0.51 | 1.35 | 0.51 | 1.35 | 1.35 | 147 |
| 155 | 0.24 | 0.65 | 0.22 | 0.59 | 0.62 | 148 |
| 156 | 0.36 | 0.96 | 0.41 | 1.09 | 1.03 | 149 |
| 157 | 0.58 | 1.55 | 0.51 | 1.35 | 1.45 | 150 |
| 158 | 0.22 | 0.59 | 0.20 | 0.52 | 0.56 | 151 |
| 159 | 0.32 | 0.86 | 0.27 | 0.72 | 0.79 | 152 |
| 160 | 0.23 | 0.61 | 0.21 | 0.54 | 0.58 | 153 |
| 161 | 0.20 | 0.53 | 0.20 | 0.53 | 0.53 | 154 |
| 162 | 0.45 | 1.19 | 0.44 | 1.17 | 1.18 | 155 |
| 163 | 0.38 | 1.00 | 0.33 | 0.87 | 0.93 | 156 |
| 164 | 0.24 | 0.63 | 0.21 | 0.55 | 0.59 | 157 |

TABLE 8-continued

Ratio of ATN-1 gene expression level in A204 cell administered with gapmer (2.0 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 165 | 0.58 | 1.53 | 0.59 | 1.57 | 1.55 | 158 |
| 166 | 0.12 | 0.31 | 0.11 | 0.28 | 0.29 | 159 |
| 168 | 0.15 | 0.39 | 0.14 | 0.37 | 0.38 | 161 |

TABLE 9

Ratio of ATN-1 gene expression level in A204 cell administered with gapmer (1.0 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 69 | 0.16 | 0.23 | 0.16 | 0.24 | 0.23 | 69 |
| 76 | 0.27 | 0.39 | 0.25 | 0.37 | 0.38 | 76 |
| 77 | 0.23 | 0.34 | 0.18 | 0.27 | 0.31 | 77 |
| 78 | 0.26 | 0.39 | 0.24 | 0.36 | 0.37 | 10 |
| 79 | 0.26 | 0.39 | 0.27 | 0.40 | 0.39 | 78 |
| 80 | 0.64 | 0.92 | 0.70 | 1.01 | 0.97 | 79 |
| 81 | 0.66 | 0.95 | 0.48 | 0.69 | 0.82 | 80 |
| 82 | 0.93 | 1.35 | 1.00 | 1.54 | 1.44 | 81 |
| 83 | 0.82 | 1.19 | 0.79 | 1.15 | 1.17 | 82 |
| 84 | 0.44 | 0.64 | 0.46 | 0.67 | 0.66 | 11 |
| 85 | 0.26 | 0.38 | 0.27 | 0.40 | 0.39 | 83 |
| 86 | 0.16 | 0.23 | 0.17 | 0.25 | 0.24 | 12 |
| 88 | 0.07 | 0.10 | 0.08 | 0.11 | 0.11 | 84 |
| 89 | 0.21 | 0.32 | 0.21 | 0.33 | 0.33 | 13 |
| 90 | 0.27 | 0.39 | 0.28 | 0.42 | 0.41 | 85 |
| 109 | 0.31 | 0.44 | 0.28 | 0.43 | 0.44 | 104 |
| 110 | 0.33 | 0.48 | 0.35 | 0.54 | 0.51 | 105 |
| 121 | 0.44 | 0.65 | 0.39 | 0.63 | 0.64 | 116 |
| 139 | 0.31 | 0.46 | 0.26 | 0.41 | 0.43 | 132 |
| 144 | 0.41 | 0.61 | 0.09 | 0.14 | 0.38 | 137 |
| 166 | 0.20 | 0.31 | 0.19 | 0.33 | 0.32 | 159 |
| 168 | 0.30 | 0.46 | 0.26 | 0.45 | 0.45 | 161 |

TABLE 10

Ratio of ATN-1 gene expression level in A204 cell administered with gapmer (0.5 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 62 | 0.24 | 0.31 | 0.39 | 0.52 | 0.41 | 62 |
| 63 | 0.30 | 0.38 | 0.42 | 0.56 | 0.47 | 63 |
| 66 | 0.88 | 1.12 | 0.72 | 0.94 | 1.03 | 66 |
| 67 | 0.79 | 1.00 | 0.72 | 0.96 | 0.98 | 67 |
| 68 | 0.16 | 0.19 | 0.20 | 0.23 | 0.21 | 68 |
| 70 | 0.26 | 0.31 | 0.29 | 0.33 | 0.32 | 70 |
| 73 | 0.72 | 0.87 | 0.77 | 0.89 | 0.88 | 73 |
| 74 | 0.83 | 1.00 | 0.87 | 1.00 | 1.00 | 74 |
| 75 | 0.82 | 0.99 | 0.87 | 0.99 | 0.99 | 75 |
| 91 | 0.93 | 1.18 | 0.96 | 1.34 | 1.26 | 86 |
| 92 | 0.79 | 1.01 | 0.84 | 1.16 | 1.09 | 87 |
| 100 | 0.50 | 0.60 | 0.58 | 0.67 | 0.63 | 95 |
| 101 | 0.72 | 0.87 | 0.69 | 0.79 | 0.83 | 96 |
| 102 | 0.55 | 0.66 | 0.55 | 0.63 | 0.64 | 97 |

TABLE 10-continued

Ratio of ATN-1 gene expression level in A204 cell administered with gapmer (0.5 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 103 | 0.41 | 0.50 | 0.42 | 0.48 | 0.49 | 98 |
| 104 | 0.73 | 0.88 | 0.80 | 0.92 | 0.90 | 99 |
| 106 | 0.28 | 0.33 | 0.33 | 0.37 | 0.35 | 101 |
| 107 | 0.72 | 0.87 | 0.72 | 0.82 | 0.85 | 102 |
| 111 | 0.52 | 0.66 | 0.51 | 0.72 | 0.69 | 106 |
| 112 | 0.46 | 0.58 | 0.47 | 0.66 | 0.62 | 107 |
| 113 | 0.89 | 1.10 | 0.84 | 0.95 | 1.03 | 108 |
| 114 | 0.94 | 1.16 | 0.86 | 0.97 | 1.07 | 109 |
| 115 | 0.73 | 0.91 | 0.73 | 0.83 | 0.87 | 110 |
| 116 | 0.76 | 0.94 | 0.68 | 0.77 | 0.86 | 111 |
| 117 | 0.11 | 0.14 | 0.11 | 0.13 | 0.13 | 112 |
| 118 | 0.18 | 0.22 | 0.20 | 0.23 | 0.22 | 113 |
| 119 | 0.35 | 0.43 | 0.37 | 0.42 | 0.43 | 114 |
| 122 | 0.67 | 0.80 | 0.66 | 0.90 | 0.85 | 117 |
| 124 | 0.31 | 0.37 | 0.29 | 0.39 | 0.38 | 30 |
| 125 | 0.97 | 1.17 | 0.80 | 1.09 | 1.13 | 118 |
| 135 | 0.56 | 0.69 | 0.51 | 0.58 | 0.64 | 128 |
| 136 | 0.79 | 0.98 | 0.74 | 0.83 | 0.91 | 129 |
| 137 | 0.47 | 0.58 | 0.47 | 0.53 | 0.56 | 130 |
| 138 | 0.38 | 0.46 | 0.38 | 0.43 | 0.45 | 131 |
| 140 | 0.25 | 0.30 | 0.22 | 0.25 | 0.28 | 133 |
| 141 | 0.45 | 0.56 | 0.47 | 0.54 | 0.55 | 134 |
| 142 | 0.92 | 1.14 | 0.86 | 0.97 | 1.06 | 135 |
| 143 | 0.65 | 0.84 | 0.67 | 0.79 | 0.82 | 136 |
| 146 | 0.96 | 1.16 | 0.95 | 1.09 | 1.12 | 139 |
| 147 | 0.64 | 0.77 | 0.72 | 0.83 | 0.80 | 140 |
| 148 | 0.85 | 1.02 | 0.85 | 0.98 | 1.00 | 141 |
| 149 | 0.90 | 1.13 | 0.91 | 1.12 | 1.13 | 142 |
| 151 | 0.80 | 0.97 | 0.82 | 0.95 | 0.96 | 144 |
| 161 | 0.50 | 0.72 | 0.59 | 0.73 | 0.73 | 154 |
| 167 | 0.25 | 0.32 | 0.25 | 0.30 | 0.31 | 160 |
| 169 | 0.49 | 0.63 | 0.51 | 0.60 | 0.61 | 162 |
| 170 | 0.39 | 0.50 | 0.42 | 0.50 | 0.50 | 163 |

TABLE 11

Ratio of ATN-1 gene expression level in A204 cell administered with gapmer (0.5 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 171 | 0.63 | 0.89 | 0.68 | 0.83 | 0.86 | 164 |
| 172 | 0.73 | 1.03 | 0.73 | 0.89 | 0.96 | 165 |
| 173 | 0.68 | 0.96 | 0.64 | 0.78 | 0.87 | 166 |
| 174 | 0.61 | 0.72 | 0.65 | 0.79 | 0.75 | 167 |
| 175 | 0.50 | 0.59 | 0.48 | 0.58 | 0.58 | 168 |
| 176 | 0.52 | 0.58 | 0.57 | 0.64 | 0.61 | 169 |
| 177 | 0.32 | 0.39 | 0.35 | 0.39 | 0.39 | 170 |
| 178 | 0.57 | 0.78 | 0.61 | 0.71 | 0.74 | 171 |
| 179 | 1.01 | 1.42 | 1.10 | 1.35 | 1.39 | 172 |
| 180 | 0.57 | 0.81 | 0.68 | 0.83 | 0.82 | 173 |
| 181 | 0.86 | 0.87 | 0.85 | 1.00 | 0.93 | 21 |
| 182 | 0.73 | 0.74 | 0.67 | 0.78 | 0.76 | 174 |
| 183 | 0.60 | 0.62 | 0.57 | 0.63 | 0.63 | 175 |
| 184 | 0.50 | 0.52 | 0.53 | 0.59 | 0.56 | 176 |
| 185 | 0.31 | 0.35 | 0.33 | 0.38 | 0.37 | 177 |
| 186 | 0.93 | 0.95 | 0.92 | 1.07 | 1.01 | 178 |
| 187 | 0.82 | 0.83 | 0.75 | 0.88 | 0.86 | 179 |
| 188 | 0.63 | 0.64 | 0.59 | 0.69 | 0.67 | 180 |
| 189 | 0.52 | 0.54 | 0.58 | 0.64 | 0.59 | 181 |
| 190 | 0.48 | 0.46 | 0.57 | 0.55 | 0.51 | 182 |
| 191 | 0.96 | 0.97 | 0.88 | 1.03 | 1.00 | 183 |

TABLE 11-continued

Ratio of ATN-1 gene expression level in A204 cell administered with gapmer (0.5 μM) having 2'-O-MOE group in wing nucleoside

| ASO No. | mRNA expression level (exon4-5) | Ratio of mRNA expression level/ NRH-71 (exon4-5) | mRNA expression level (exon6-7) | Ratio of mRNA expression level/ NRH-71 (exon6-7) | Average of ratio of mRNA expression level | SEQ ID NO: |
|---|---|---|---|---|---|---|
| 192 | 0.79 | 0.80 | 0.76 | 0.89 | 0.84 | 184 |
| 193 | 0.77 | 1.09 | 0.84 | 1.03 | 1.06 | 185 |
| 194 | 0.81 | 0.96 | 0.88 | 1.05 | 1.01 | 186 |
| 195 | 0.73 | 0.87 | 0.81 | 0.97 | 0.92 | 187 |
| 196 | 0.79 | 0.76 | 0.81 | 0.79 | 0.78 | 188 |
| 197 | 0.86 | 0.86 | 0.84 | 0.87 | 0.87 | 189 |
| 198 | 0.60 | 0.59 | 0.71 | 0.69 | 0.64 | 190 |
| 199 | 1.03 | 1.03 | 0.92 | 0.95 | 0.99 | 191 |
| 200 | 0.82 | 0.83 | 0.80 | 0.94 | 0.88 | 192 |
| 201 | 0.55 | 0.56 | 0.56 | 0.66 | 0.61 | 193 |
| 202 | 0.60 | 0.62 | 0.63 | 0.69 | 0.66 | 194 |
| 203 | 0.62 | 0.60 | 0.69 | 0.67 | 0.64 | 195 |
| 204 | 0.31 | 0.34 | 0.32 | 0.34 | 0.34 | 196 |
| 205 | 0.45 | 0.51 | 0.46 | 0.52 | 0.52 | 197 |
| 206 | 0.65 | 0.74 | 0.67 | 0.76 | 0.75 | 198 |
| 207 | 0.36 | 0.41 | 0.41 | 0.42 | 0.41 | 199 |
| 208 | 0.55 | 0.57 | 0.62 | 0.68 | 0.63 | 200 |
| 209 | 0.53 | 0.55 | 0.63 | 0.69 | 0.62 | 201 |
| 210 | 0.67 | 0.65 | 0.75 | 0.73 | 0.69 | 202 |
| 211 | 0.91 | 0.88 | 0.91 | 0.88 | 0.88 | 203 |
| 212 | 1.00 | 0.97 | 0.92 | 0.90 | 0.93 | 204 |
| 213 | 0.80 | 0.90 | 0.74 | 0.77 | 0.83 | 205 |
| 214 | 0.76 | 0.84 | 0.78 | 0.80 | 0.82 | 206 |
| 215 | 0.81 | 0.78 | 0.81 | 0.79 | 0.79 | 207 |
| 216 | 0.90 | 0.87 | 0.77 | 0.75 | 0.81 | 208 |
| 217 | 0.67 | 0.95 | 0.78 | 0.96 | 0.95 | 209 |
| 218 | 0.65 | 0.92 | 0.79 | 0.96 | 0.94 | 210 |
| 219 | 0.62 | 0.87 | 0.68 | 0.83 | 0.85 | 211 |
| 220 | 0.69 | 0.86 | 0.70 | 0.80 | 0.83 | 212 |
| 221 | 0.75 | 0.89 | 0.85 | 1.02 | 0.95 | 213 |
| 222 | 0.79 | 0.93 | 0.81 | 0.97 | 0.95 | 214 |
| 223 | 0.82 | 0.97 | 0.88 | 1.06 | 1.02 | 215 |
| 224 | 0.67 | 0.95 | 0.74 | 0.90 | 0.93 | 216 |
| 225 | 0.80 | 1.13 | 0.88 | 1.08 | 1.11 | 217 |
| 226 | 0.86 | 1.21 | 0.96 | 1.18 | 1.19 | 218 |
| 227 | 0.48 | 0.56 | 0.49 | 0.54 | 0.55 | 219 |
| 228 | 0.51 | 0.63 | 0.53 | 0.61 | 0.62 | 220 |
| 229 | 0.39 | 0.47 | 0.39 | 0.45 | 0.46 | 221 |
| 230 | 0.81 | 0.96 | 0.85 | 1.02 | 0.99 | 222 |
| 241 | 0.69 | 0.67 | 0.69 | 0.67 | 0.67 | 233 |
| 242 | 0.80 | 0.77 | 0.90 | 0.87 | 0.82 | 234 |
| 358 | 0.72 | 0.81 | 0.72 | 0.74 | 0.78 | 350 |
| 359 | 0.73 | 0.71 | 0.67 | 0.65 | 0.68 | 351 |
| 360 | 0.75 | 0.72 | 0.71 | 0.69 | 0.71 | 352 |
| 361 | 0.73 | 0.71 | 0.69 | 0.67 | 0.69 | 353 |
| 362 | 0.82 | 0.80 | 0.80 | 0.78 | 0.79 | 354 |
| 363 | 0.88 | 0.85 | 0.90 | 0.88 | 0.86 | 355 |
| 473 | 0.45 | 0.58 | 0.45 | 0.58 | 0.58 | 472 |
| 474 | 0.48 | 0.62 | 0.41 | 0.54 | 0.58 | 472 |
| 475 | 0.55 | 0.71 | 0.44 | 0.58 | 0.64 | 472 |
| 476 | 0.43 | 0.56 | 0.47 | 0.61 | 0.59 | 472 |
| 477 | 0.64 | 0.83 | 0.61 | 0.80 | 0.82 | 472 |
| 478 | 0.58 | 0.74 | 0.51 | 0.66 | 0.70 | 472 |
| 479 | 0.57 | 0.74 | 0.48 | 0.62 | 0.68 | 472 |
| 480 | 0.09 | 0.11 | 0.10 | 0.13 | 0.12 | 177 |
| 481 | 0.10 | 0.13 | 0.14 | 0.18 | 0.16 | 177 |
| 482 | 0.13 | 0.17 | 0.13 | 0.17 | 0.17 | 177 |
| 483 | 0.07 | 0.09 | 0.07 | 0.09 | 0.09 | 177 |
| 484 | 0.19 | 0.25 | 0.17 | 0.23 | 0.24 | 177 |
| 485 | 0.16 | 0.20 | 0.13 | 0.16 | 0.18 | 177 |
| 486 | 0.10 | 0.13 | 0.08 | 0.10 | 0.12 | 177 |
| 487 | 0.44 | 0.44 | 0.41 | 0.42 | 0.43 | 133 |
| 488 | 0.26 | 0.26 | 0.28 | 0.29 | 0.28 | 133 |
| 489 | 0.39 | 0.39 | 0.44 | 0.45 | 0.42 | 133 |
| 490 | 0.32 | 0.32 | 0.24 | 0.24 | 0.28 | 133 |
| 491 | 0.43 | 0.43 | 0.43 | 0.45 | 0.44 | 133 |
| 492 | 0.36 | 0.36 | 0.40 | 0.41 | 0.39 | 133 |
| 493 | 0.37 | 0.37 | 0.36 | 0.37 | 0.37 | 133 |
| 494 | 0.13 | 0.14 | 0.10 | 0.11 | 0.13 | 196 |
| 495 | 0.14 | 0.16 | 0.11 | 0.12 | 0.14 | 196 |
| 497 | 0.29 | 0.31 | 0.30 | 0.32 | 0.31 | 473 |
| 498 | 0.15 | 0.16 | 0.13 | 0.14 | 0.15 | 473 |
| 499 | 0.20 | 0.21 | 0.18 | 0.19 | 0.20 | 473 |

The invention claimed is:

1. An antisense oligonucleotide, or a pharmaceutically acceptable salt thereof, or a hydrate thereof, comprising the nucleic acid sequence of SEQ ID NO: 133, wherein the antisense oligonucleotide is 20 nucleotides long.

2. An antisense oligonucleotide, or a pharmaceutically acceptable salt thereof, or a hydrate thereof, comprising the nucleic acid sequence of SEQ ID NO: 196, wherein the antisense oligonucleotide is 20 nucleotides long.

3. The antisense oligonucleotide, or a pharmaceutically acceptable salt thereof, or a hydrate thereof according to claim 1, wherein a sugar moiety and/or a phosphate-bond moiety of at least one nucleotide of the antisense oligonucleotide is modified.

4. The antisense oligonucleotide, or a pharmaceutically acceptable salt thereof, or a hydrate thereof according to claim 3, wherein the antisense oligonucleotide is a gapmer comprising from 5' to 3': a 5' wing region, a gap region and a 3' wing region.

5. The antisense oligonucleotide, or a pharmaceutically acceptable salt thereof, or a hydrate thereof according to claim 4, wherein internucleotide bonds between nucleosides are all phosphorothioate bonds.

6. The antisense oligonucleotide, or a pharmaceutically acceptable salt thereof, or a hydrate thereof according to claim 4, wherein one or more internucleotide bonds between the 2nd and 3rd nucleosides, the 3rd and 4th nucleosides, and/or the 4th and 5th nucleosides from the 5' side of the 5' wing region are phosphodiester bonds; and/or one or more internucleotide bonds-between the 1st and 2nd nucleosides, the 2nd and 3rd nucleosides, and/or the 3rd and 4th nucleosides from the 5' side of the 3' wing region are phosphodiester bonds; and wherein internucleotide bonds between the other nucleosides are all phosphorothioate bonds.

7. The antisense oligonucleotide, or a pharmaceutically acceptable salt thereof, or a hydrate thereof according to claim 6, wherein the internucleotide bond between the 2nd and 3rd nucleosides, and the internucleotide bond between the 4th and 5th nucleosides from the 5' side of the 5' wing region are phosphodiester bonds; and/or the internucleotide bond between the 1st and 2nd nucleosides, and the internucleotide bond between the 3rd and 4th nucleosides from the 5' side of the 3' wing region are phosphodiester bonds; and wherein internucleotide bonds between the other nucleosides are all phosphorothioate bonds.

8. The antisense oligonucleotide, or a pharmaceutically acceptable salt thereof, or a hydrate thereof according to claim 6, wherein the internucleotide bond between the 2nd and 3rd nucleosides, the internucleotide bond between the 3rd and 4th nucleosides, and the internucleotide bond between the 4th and 5th nucleosides from the 5' side of the 5' wing region are phosphodiester bonds; and/or the internucleotide bond between the 1st and 2nd nucleosides, the internucleotide bond between the 2nd and 3rd nucleosides, and the internucleotide bond between the 3rd and 4th nucleosides from the 5' side of the 3' wing region are phosphodiester bonds; and wherein internucleotide bonds between the other nucleosides are all phosphorothioate bonds.

9. The antisense oligonucleotide, or a pharmaceutically acceptable salt thereof, or a hydrate thereof according to claim 4, wherein the 5' wing region and/or 3' wing region comprises a 2'-OMe (2'-O—$CH_3$) group and/or a 2'-O-MOE (2'-O—$CH_2CH_2OCH_3$) group.

10. The antisense oligonucleotide, or a pharmaceutically acceptable salt thereof, or a hydrate thereof according to claim 1, wherein the antisense oligonucleotide is a gapmer comprising, from 5' to 3', a 5' wing region of 5 nucleotides, a gap region of 10 nucleotides, and a 3' wing region of 5 nucleotides; wherein at least one nucleoside of the 5' wing region and 3' wing region comprises a 2'-O-MOE (2'-O—$CH_2CH_2OCH_3$) group; and wherein internucleotide bonds between nucleosides are all phosphorothioate bonds.

11. The antisense oligonucleotide, or a pharmaceutically acceptable salt thereof, or a hydrate thereof according to claim 2, wherein the antisense oligonucleotide is a gapmer comprising, from 5' to 3', a 5' wing region of 5 nucleotides, a gap region of 10 nucleotides, and a 3' wing region of 5 nucleotides; wherein at least one nucleoside of the 5' wing region and 3' wing region comprises a 2'-O-MOE (2'-O—$CH_2CH_2OCH_3$) group; wherein the internucleotide bond between the 2nd and 3rd nucleosides, the internucleotide bond between the 3rd and 4th nucleosides, and the internucleotide bond between the 4th and 5th nucleosides from the 5' side of the 5' wing region are phosphodiester bonds, and the internucleotide bond between the 1st and 2nd nucleosides, the internucleotide bond between the 2nd and 3rd nucleosides, and the internucleotide bond between the 3rd and 4th nucleosides from the 5' side of the 3' wing region are phosphodiester bonds; and wherein internucleotide bonds between the other nucleosides are all phosphorothioate bonds.

12. The antisense oligonucleotide, or a pharmaceutically acceptable salt thereof, or a hydrate thereof according to claim 2, wherein the antisense oligonucleotide is a gapmer comprising, from 5' to 3', a 5' wing region of 5 nucleotides, a gap region of 10 nucleotides, and a 3' wing region of 5 nucleotides; wherein at least one nucleoside of the 5' wing region and 3' wing region region comprises a 2'-O-MOE (2'-O—$CH_2CH_2OCH_3$) group; wherein the internucleotide bond between the 2nd and 3rd nucleosides, and the internucleotide bond between the 4th and 5th nucleosides from the 5' side of the 5' wing region are phosphodiester bonds, and the internucleotide bond between the 1st and 2nd nucleosides, and the internucleotide bond between the 3rd and 4th nucleosides from the 5' side of the 3' wing region are phosphodiester bonds; and wherein internucleotide bonds between the other nucleosides are all phosphorothioate bonds.

13. The antisense oligonucleotide, or a pharmaceutically acceptable salt thereof, or a hydrate thereof according to claim 10, wherein all nucleosides of the 5' wing region and 3' wing region comprise a 2'-O-MOE (2'-O—$CH_2CH_2OCH_3$) group.

14. The antisense oligonucleotide, or a pharmaceutically acceptable salt thereof, or a hydrate thereof according to claim 11, wherein all nucleosides of the 5' wing region and 3' wing region comprise a 2'-O-MOE (2'-O—$CH_2CH_2OCH_3$) group.

15. The antisense oligonucleotide, or a pharmaceutically acceptable salt thereof, or a hydrate thereof according to claim 12, wherein all nucleosides of the 5' wing region and 3' wing region comprise a 2'-O-MOE (2'-O—$CH_2CH_2OCH_3$) group.

16. A pharmaceutical composition comprising the antisense oligonucleotide, or a pharmaceutically acceptable salt thereof, or a hydrate thereof according to claim 1.

17. A method for treating dentatorubral-pallidoluysian atrophy (DRPLA) by reducing ATN1 expression, comprising administering to a subject the antisense oligonucleotide, or a pharmaceutically acceptable salt thereof, or a hydrate thereof according to claim 1.

18. An antisense oligonucleotide composition comprising the nucleic acid sequence of SEQ ID NO: 133 or the nucleic acid sequence of SEQ ID NO: 196, wherein the antisense oligonucleotide is 20 nucleotides long.

* * * * *

SEQUENCE LISTING

```
Sequence total quantity: 473
SEQ ID NO: 1            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 1
tcctcccact tggcgtccag                                              20

SEQ ID NO: 2            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 2
agaagcagag cgggaggccc                                              20

SEQ ID NO: 3            moltype = DNA  length = 20
FEATURE                 Location/Qualifiers
misc_feature            1..20
                        note = Synthetic
source                  1..20
```

```
                        mol_type = other DNA
                        organism = synthetic construct
SEQUENCE: 3
ttccccacag ctgtggtctg                                            20

SEQ ID NO: 4            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 4
gtggaggctt cctctactcg                                            20

SEQ ID NO: 5            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 5
aggaggaaag agtggaggtg                                            20

SEQ ID NO: 6            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 6
ggtgctgtct ggcggttgag                                            20

SEQ ID NO: 7            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 7
ttcaaagcta gcctctggct                                            20

SEQ ID NO: 8            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 8
ttagggcccc ccactgatga                                            20

SEQ ID NO: 9            moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 9
ggcaggttcg gtgtcacatg                                            20

SEQ ID NO: 10           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 10
agaggctgat gcattgttga                                            20

SEQ ID NO: 11           moltype = DNA  length = 20
FEATURE                 Location/Qualifiers
misc_feature            1..20
                        note = Synthetic
```

```
source                  1..20
                        mol_type = other DNA
                        organism = synthetic construct
SEQUENCE: 11
tggttgggcc cccaggccag                                           20

SEQ ID NO: 12           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 12
gcagatgacc aggtagtggt                                           20

SEQ ID NO: 13           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 13
ggagagggca gatgaccagg                                           20

SEQ ID NO: 14           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 14
ggtgaaggag ccagagttgg                                           20

SEQ ID NO: 15           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 15
gagacagaga ggcttgttgg                                           20

SEQ ID NO: 16           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 16
attggagaca gagaggcttg                                           20

SEQ ID NO: 17           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 17
ctgattggag acagagaggc                                           20

SEQ ID NO: 18           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 18
ggctgattgg agacagagag                                           20

SEQ ID NO: 19           moltype = DNA  length = 20
FEATURE                 Location/Qualifiers
misc_feature            1..20
```

```
                        note = Synthetic
source                  1..20
                        mol_type = other DNA
                        organism = synthetic construct
SEQUENCE: 19
agagaaggct gagtatactt                                                20

SEQ ID NO: 20           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 20
accctggctc cacacagcct                                                20

SEQ ID NO: 21           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 21
gcattgctgt tggctaagag                                                20

SEQ ID NO: 22           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 22
ctgttgctgt tgctggtggt                                                20

SEQ ID NO: 23           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 23
ggcccagagt ttccgtgatg                                                20

SEQ ID NO: 24           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 24
ggagctaccg ccctccagtg                                                20

SEQ ID NO: 25           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 25
catggcgtaa gggtgtgcgt                                                20

SEQ ID NO: 26           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 26
aggacacctg gctgtgaggt                                                20

SEQ ID NO: 27           moltype = DNA  length = 20
FEATURE                 Location/Qualifiers
```

```
misc_feature          1..20
                      note = Synthetic
source                1..20
                      mol_type = other DNA
                      organism = synthetic construct
SEQUENCE: 27
gcctgcttgg ctgtaggaca                                              20

SEQ ID NO: 28         moltype = DNA  length = 20
FEATURE               Location/Qualifiers
misc_feature          1..20
                      note = Synthetic
source                1..20
                      mol_type = other DNA
                      organism = synthetic construct
SEQUENCE: 28
gaagagactg gagggccatt                                              20

SEQ ID NO: 29         moltype = DNA  length = 20
FEATURE               Location/Qualifiers
misc_feature          1..20
                      note = Synthetic
source                1..20
                      mol_type = other DNA
                      organism = synthetic construct
SEQUENCE: 29
ccacggtggc aatgaccgtg                                              20

SEQ ID NO: 30         moltype = DNA  length = 20
FEATURE               Location/Qualifiers
misc_feature          1..20
                      note = Synthetic
source                1..20
                      mol_type = other DNA
                      organism = synthetic construct
SEQUENCE: 30
gaggccgttt tgtagcctgc                                              20

SEQ ID NO: 31         moltype = DNA  length = 20
FEATURE               Location/Qualifiers
misc_feature          1..20
                      note = Synthetic
source                1..20
                      mol_type = other DNA
                      organism = synthetic construct
SEQUENCE: 31
ggctctcttt ccgtacggtg                                              20

SEQ ID NO: 32         moltype = DNA  length = 20
FEATURE               Location/Qualifiers
misc_feature          1..20
                      note = Synthetic
source                1..20
                      mol_type = other DNA
                      organism = synthetic construct
SEQUENCE: 32
gcgacccggg tttgtatccg                                              20

SEQ ID NO: 33         moltype = DNA  length = 20
FEATURE               Location/Qualifiers
misc_feature          1..20
                      note = Synthetic
source                1..20
                      mol_type = other DNA
                      organism = synthetic construct
SEQUENCE: 33
cgaggttcct cgatagcccg                                              20

SEQ ID NO: 34         moltype = DNA  length = 20
FEATURE               Location/Qualifiers
misc_feature          1..20
                      note = Synthetic
source                1..20
                      mol_type = other DNA
                      organism = synthetic construct
SEQUENCE: 34
tcccacggtg ggcgagcccg                                              20

SEQ ID NO: 35         moltype = DNA  length = 20
```

```
FEATURE                 Location/Qualifiers
misc_feature            1..20
                        note = Synthetic
source                  1..20
                        mol_type = other DNA
                        organism = synthetic construct
SEQUENCE: 35
ggtggtggca gcgatggcag                                                      20

SEQ ID NO: 36           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 36
cagcttggag ccctccagtg                                                      20

SEQ ID NO: 37           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 37
ctgctcggcc tcgcgccgca                                                      20

SEQ ID NO: 38           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 38
tcttcgcgcg cgcgctgctc                                                      20

SEQ ID NO: 39           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 39
tctttctcgc gttcccgctc                                                      20

SEQ ID NO: 40           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 40
tcaagctcgc gctccttctc                                                      20

SEQ ID NO: 41           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 41
acgctgcgtt caagctcgcg                                                      20

SEQ ID NO: 42           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 42
gcattccacc ggagcacggc                                                      20
```

```
SEQ ID NO: 43           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 43
cgcactgccc ggttcaaatg                                              20

SEQ ID NO: 44           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 44
gcttcccgtt ccctctcccg                                              20

SEQ ID NO: 45           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 45
cacggaggtc tcgttcacgg                                              20

SEQ ID NO: 46           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 46
gaaagggatc caagcccggc                                              20

SEQ ID NO: 47           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 47
gccaggctgc agagccaggc                                              20

SEQ ID NO: 48           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 48
ctagacgttc tcgctccagg                                              20

SEQ ID NO: 49           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 49
gctggcccag ctgccagcgc                                              20

SEQ ID NO: 50           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 50
gtgcaggtgc gagtggatgt                                              20
```

```
SEQ ID NO: 51          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 51
agaacttcgt tctcgtgcag                                              20

SEQ ID NO: 52          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 52
gaggccggca ggtcccggta                                              20

SEQ ID NO: 53          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 53
gcagaaaggg aggccggcag                                              20

SEQ ID NO: 54          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 54
gtgcatggcc tgcagctgat                                              20

SEQ ID NO: 55          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 55
catgcagcca ctgctgctgt                                              20

SEQ ID NO: 56          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 56
gcagcggcac actgtgcagc                                              20

SEQ ID NO: 57          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 57
ccctccctcc cccactctct                                              20

SEQ ID NO: 58          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 58
```

```
gccacctccc cacctctgca                                                   20

SEQ ID NO: 59           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 59
gcaggggaca gccttgaagt                                                   20

SEQ ID NO: 60           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 60
ctcgggcctt cttggctgtc                                                   20

SEQ ID NO: 61           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 61
ctcactttca ctctctgaga                                                   20

SEQ ID NO: 62           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 62
ggtctcctca ctttcactct                                                   20

SEQ ID NO: 63           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 63
ggtcgctgct gccatcatca                                                   20

SEQ ID NO: 64           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 64
tagggtcgct gctgccatca                                                   20

SEQ ID NO: 65           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 65
gggacgtgct tcggttgtcc                                                   20

SEQ ID NO: 66           moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 66
ctgtcgaggg gtgctgtctg                                         20

SEQ ID NO: 67          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 67
tggctgtcga ggggtgctgt                                         20

SEQ ID NO: 68          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 68
aagctagcct ctggctgtcg                                         20

SEQ ID NO: 69          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 69
gttcaaagct agcctctggc                                         20

SEQ ID NO: 70          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 70
ggggttcaaa gctagcctct                                         20

SEQ ID NO: 71          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 71
atatccagtg ggtgtcacag                                         20

SEQ ID NO: 72          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 72
ggaggagcct ggaacattcg                                         20

SEQ ID NO: 73          moltype = DNA  length = 20
FEATURE                Location/Qualifiers
misc_feature           1..20
                       note = Synthetic
source                 1..20
                       mol_type = other DNA
                       organism = synthetic construct
SEQUENCE: 73
ggtctcaggg caggtggggg                                         20

SEQ ID NO: 74          moltype = DNA  length = 20
FEATURE                Location/Qualifiers
misc_feature           1..20
                       note = Synthetic
source                 1..20
                       mol_type = other DNA
```

```
                         organism = synthetic construct
SEQUENCE: 74
aggggtctca gggcaggtgg                                              20

SEQ ID NO: 75            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 75
ttgaggggtc tcagggcagg                                              20

SEQ ID NO: 76            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 76
gcattgttga ggggtctcag                                              20

SEQ ID NO: 77            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 77
atgcattgtt gaggggtctc                                              20

SEQ ID NO: 78            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 78
gggagaggct gatgcattgt                                              20

SEQ ID NO: 79            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 79
caggccaggg ggagaggctg                                              20

SEQ ID NO: 80            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 80
ccccaggcca gggggagagg                                              20

SEQ ID NO: 81            moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 81
ggcccccagg ccagggggag                                              20

SEQ ID NO: 82            moltype = DNA  length = 20
FEATURE                  Location/Qualifiers
misc_feature             1..20
                         note = Synthetic
source                   1..20
```

```
                        mol_type = other DNA
                        organism = synthetic construct
SEQUENCE: 82
ttgggccccc aggccagggg                                                20

SEQ ID NO: 83           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 83
tgaccaggta gtggttgggc                                                20

SEQ ID NO: 84           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 84
gagagggcag atgaccaggt                                                20

SEQ ID NO: 85           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 85
ggggagaggg cagatgacca                                                20

SEQ ID NO: 86           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 86
ccatggcgtg gggagagggc                                                20

SEQ ID NO: 87           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 87
gtcccatggc gtggggagag                                                20

SEQ ID NO: 88           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 88
ccctgtccca tggcgtgggg                                                20

SEQ ID NO: 89           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 89
ggcccttctc tgggccagga                                                20

SEQ ID NO: 90           moltype = DNA  length = 20
FEATURE                 Location/Qualifiers
misc_feature            1..20
                        note = Synthetic
```

```
source                  1..20
                        mol_type = other DNA
                        organism = synthetic construct
SEQUENCE: 90
gaagaggagg ctgctgcaga                                              20

SEQ ID NO: 91           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 91
tgggcaatgc ctgggaagct                                              20

SEQ ID NO: 92           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 92
agtatacttg gggggctgat                                              20

SEQ ID NO: 93           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 93
cagcctggga tgggagagaa                                              20

SEQ ID NO: 94           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 94
taagaggcgg ccatagggag                                              20

SEQ ID NO: 95           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 95
ctgttggcta agaggcggcc                                              20

SEQ ID NO: 96           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 96
ttgctgttgg ctaagaggcg                                              20

SEQ ID NO: 97           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 97
tgggcattgc tgttggctaa                                              20

SEQ ID NO: 98           moltype = DNA  length = 20
FEATURE                 Location/Qualifiers
misc_feature            1..20
```

```
                        note = Synthetic
source                  1..20
                        mol_type = other DNA
                        organism = synthetic construct
SEQUENCE: 98
ggatgggcat tgctgttggc                                           20

SEQ ID NO: 99           moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 99
cctggatggg cattgctgtt                                           20

SEQ ID NO: 100          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 100
gggcctggat gggcattgct                                           20

SEQ ID NO: 101          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 101
aaggggcctg gatgggcatt                                           20

SEQ ID NO: 102          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 102
gggaaggggc ctggatgggc                                           20

SEQ ID NO: 103          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 103
gaaatgctcc aggaggaggg                                           20

SEQ ID NO: 104          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 104
gcaggtgtgc tggccctggt                                           20

SEQ ID NO: 105          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 105
ggcaggtgtg ctggccctgg                                           20

SEQ ID NO: 106          moltype = DNA  length = 20
FEATURE                 Location/Qualifiers
```

```
misc_feature          1..20
                      note = Synthetic
source                1..20
                      mol_type = other DNA
                      organism = synthetic construct
SEQUENCE: 106
gggggcaggt gtgctggccc                                             20

SEQ ID NO: 107        moltype = DNA  length = 20
FEATURE               Location/Qualifiers
misc_feature          1..20
                      note = Synthetic
source                1..20
                      mol_type = other DNA
                      organism = synthetic construct
SEQUENCE: 107
ggtgggggca ggtgtgctgg                                             20

SEQ ID NO: 108        moltype = DNA  length = 20
FEATURE               Location/Qualifiers
misc_feature          1..20
                      note = Synthetic
source                1..20
                      mol_type = other DNA
                      organism = synthetic construct
SEQUENCE: 108
tgaggtgggg gcaggtgtgc                                             20

SEQ ID NO: 109        moltype = DNA  length = 20
FEATURE               Location/Qualifiers
misc_feature          1..20
                      note = Synthetic
source                1..20
                      mol_type = other DNA
                      organism = synthetic construct
SEQUENCE: 109
ctgtgaggtg ggggcaggtg                                             20

SEQ ID NO: 110        moltype = DNA  length = 20
FEATURE               Location/Qualifiers
misc_feature          1..20
                      note = Synthetic
source                1..20
                      mol_type = other DNA
                      organism = synthetic construct
SEQUENCE: 110
tggctgtgag gtgggggcag                                             20

SEQ ID NO: 111        moltype = DNA  length = 20
FEATURE               Location/Qualifiers
misc_feature          1..20
                      note = Synthetic
source                1..20
                      mol_type = other DNA
                      organism = synthetic construct
SEQUENCE: 111
acctggctgt gaggtggggg                                             20

SEQ ID NO: 112        moltype = DNA  length = 20
FEATURE               Location/Qualifiers
misc_feature          1..20
                      note = Synthetic
source                1..20
                      mol_type = other DNA
                      organism = synthetic construct
SEQUENCE: 112
ttggctgtag gacacctggc                                             20

SEQ ID NO: 113        moltype = DNA  length = 20
FEATURE               Location/Qualifiers
misc_feature          1..20
                      note = Synthetic
source                1..20
                      mol_type = other DNA
                      organism = synthetic construct
SEQUENCE: 113
tgcttggctg taggacacct                                             20

SEQ ID NO: 114        moltype = DNA  length = 20
```

```
FEATURE                Location/Qualifiers
misc_feature           1..20
                       note = Synthetic
source                 1..20
                       mol_type = other DNA
                       organism = synthetic construct
SEQUENCE: 114
attggggcct gcttggctgt                                                   20

SEQ ID NO: 115         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 115
ggcgcccctt gagggccctg                                                   20

SEQ ID NO: 116         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 116
tggcgaggaa gccacggtgg                                                   20

SEQ ID NO: 117         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 117
gctggcgagg aagccacggt                                                   20

SEQ ID NO: 118         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 118
ggcccaggtg gggaggccgt                                                   20

SEQ ID NO: 119         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 119
gcccccgggg acggggctct                                                   20

SEQ ID NO: 120         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 120
agcccggtgg ggtccccgtt                                                   20

SEQ ID NO: 121         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 121
agcccggctt gaaggtccct                                                   20
```

```
SEQ ID NO: 122          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 122
gtggcagggg cccaggtccc                                              20

SEQ ID NO: 123          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 123
caggcctgag ggccccgcag                                              20

SEQ ID NO: 124          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 124
ctcaggggcg gccctgaggc                                              20

SEQ ID NO: 125          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 125
ggcccgcttc ttggccagct                                              20

SEQ ID NO: 126          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 126
cgcaccttct ccaccaggtc                                              20

SEQ ID NO: 127          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 127
cgctcctttt cttcgcgcgc                                              20

SEQ ID NO: 128          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 128
cgctctttct cgcgttcccg                                              20

SEQ ID NO: 129          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 129
tcgcgctctt tctcgcgttc                                              20
```

```
SEQ ID NO: 130          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 130
cgctcgcgct ctttctcgcg                                              20

SEQ ID NO: 131          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 131
tcgcgctcgc gctctttctc                                              20

SEQ ID NO: 132          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 132
ttctcgcgct cgcgctcttt                                              20

SEQ ID NO: 133          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 133
tccttctcgc gctcgcgctc                                              20

SEQ ID NO: 134          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 134
cgctccttct cgcgctcgcg                                              20

SEQ ID NO: 135          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 135
tcgcgctcct tctcgcgctc                                              20

SEQ ID NO: 136          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 136
agctcgcgct ccttctcgcg                                              20

SEQ ID NO: 137          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 137
```

```
gagccaactt cacgctgcgt                                                  20

SEQ ID NO: 138          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 138
tgggcccaga gatgggcatt                                                  20

SEQ ID NO: 139          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 139
caccgcactg cccggttcaa                                                  20

SEQ ID NO: 140          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 140
agccaccgca ctgcccggtt                                                  20

SEQ ID NO: 141          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 141
tgtagccacc gcactgcccg                                                  20

SEQ ID NO: 142          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 142
cactgtagcc accgcactgc                                                  20

SEQ ID NO: 143          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 143
gggcactgta gccaccgcac                                                  20

SEQ ID NO: 144          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 144
gtagggggc actgtagcca                                                   20

SEQ ID NO: 145          moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 145
ggtccactgc ccccaggggc                                               20

SEQ ID NO: 146          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 146
ggggttccag ctcactaggc                                               20

SEQ ID NO: 147          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 147
aaagggtgca ggccaggtgg                                               20

SEQ ID NO: 148          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 148
gcctctcagc tgccagccgc                                               20

SEQ ID NO: 149          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 149
ccagggccgc cacccttct                                                20

SEQ ID NO: 150          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 150
taaggggcag caaagagctg                                               20

SEQ ID NO: 151          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 151
tgagctgctg acatcggggc                                               20

SEQ ID NO: 152          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 152
agctcagctg actgtgcgtg                                               20

SEQ ID NO: 153          moltype = DNA  length = 20
FEATURE                 Location/Qualifiers
misc_feature            1..20
                        note = Synthetic
source                  1..20
                        mol_type = other DNA
```

```
                         organism = synthetic construct
SEQUENCE: 153
gttccagcgc caagcgctgc                                                20

SEQ ID NO: 154           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 154
ctcctgggca ggcagcggca                                                20

SEQ ID NO: 155           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 155
caggccaagg gcacggtggg                                                20

SEQ ID NO: 156           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 156
tggccttctg tctgtccctc                                                20

SEQ ID NO: 157           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 157
ctgcacacca catcgggcct                                                20

SEQ ID NO: 158           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 158
gtccccatcc tcgccacctc                                                20

SEQ ID NO: 159           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 159
aatcacacca acggggcagg                                                20

SEQ ID NO: 160           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 160
tggcacacga tgctacgcaa                                                20

SEQ ID NO: 161           moltype = DNA  length = 20
FEATURE                  Location/Qualifiers
misc_feature             1..20
                         note = Synthetic
source                   1..20
```

```
                          mol_type = other DNA
                          organism = synthetic construct
SEQUENCE: 161
gggtggcaca cgatgctacg                                                 20

SEQ ID NO: 162            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 162
caggggtggc acacgatgct                                                 20

SEQ ID NO: 163            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 163
gggcaggggt ggcacacgat                                                 20

SEQ ID NO: 164            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 164
ctactcgggc cttcttggct                                                 20

SEQ ID NO: 165            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 165
cctctactcg ggccttcttg                                                 20

SEQ ID NO: 166            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 166
cttcctctac tcgggccttc                                                 20

SEQ ID NO: 167            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 167
ggctaagagg cggccatagg                                                 20

SEQ ID NO: 168            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 168
gttggctaag aggcggccat                                                 20

SEQ ID NO: 169            moltype = DNA  length = 20
FEATURE                   Location/Qualifiers
misc_feature              1..20
                          note = Synthetic
```

```
source                  1..20
                        mol_type = other DNA
                        organism = synthetic construct
SEQUENCE: 169
tgttggctaa gaggcggcca                                          20

SEQ ID NO: 170          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 170
gctgttggct aagaggcggc                                          20

SEQ ID NO: 171          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 171
tgctgttggc taagaggcgg                                          20

SEQ ID NO: 172          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 172
attgctgttg gctaagaggc                                          20

SEQ ID NO: 173          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 173
cattgctgtt ggctaagagg                                          20

SEQ ID NO: 174          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 174
ggcattgctg ttggctaaga                                          20

SEQ ID NO: 175          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 175
gggcattgct gttggctaag                                          20

SEQ ID NO: 176          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 176
atgggcattg ctgttggcta                                          20

SEQ ID NO: 177          moltype = DNA  length = 20
FEATURE                 Location/Qualifiers
misc_feature            1..20
```

```
                        note = Synthetic
source                  1..20
                        mol_type = other DNA
                        organism = synthetic construct
SEQUENCE: 177
gatgggcatt gctgttggct                                              20

SEQ ID NO: 178          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 178
tggatgggca ttgctgttgg                                              20

SEQ ID NO: 179          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 179
ctggatgggc attgctgttg                                              20

SEQ ID NO: 180          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 180
gcctggatgg gcattgctgt                                              20

SEQ ID NO: 181          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 181
ggcctggatg ggcattgctg                                              20

SEQ ID NO: 182          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 182
ggggcctgga tgggcattgc                                              20

SEQ ID NO: 183          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 183
aggtgggggc aggtgtgctg                                              20

SEQ ID NO: 184          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 184
gaggtggggg caggtgtgct                                              20

SEQ ID NO: 185          moltype = DNA  length = 20
FEATURE                 Location/Qualifiers
```

```
misc_feature          1..20
                      note = Synthetic
source                1..20
                      mol_type = other DNA
                      organism = synthetic construct
SEQUENCE: 185
cgaggaagcc acggtggcaa                                          20

SEQ ID NO: 186        moltype = DNA  length = 20
FEATURE               Location/Qualifiers
misc_feature          1..20
                      note = Synthetic
source                1..20
                      mol_type = other DNA
                      organism = synthetic construct
SEQUENCE: 186
ccttctccac caggtcggcc                                          20

SEQ ID NO: 187        moltype = DNA  length = 20
FEATURE               Location/Qualifiers
misc_feature          1..20
                      note = Synthetic
source                1..20
                      mol_type = other DNA
                      organism = synthetic construct
SEQUENCE: 187
gcgccgcacc ttctccacca                                          20

SEQ ID NO: 188        moltype = DNA  length = 20
FEATURE               Location/Qualifiers
misc_feature          1..20
                      note = Synthetic
source                1..20
                      mol_type = other DNA
                      organism = synthetic construct
SEQUENCE: 188
ctctttctcg cgttcccgct                                          20

SEQ ID NO: 189        moltype = DNA  length = 20
FEATURE               Location/Qualifiers
misc_feature          1..20
                      note = Synthetic
source                1..20
                      mol_type = other DNA
                      organism = synthetic construct
SEQUENCE: 189
gctctttctc gcgttcccgc                                          20

SEQ ID NO: 190        moltype = DNA  length = 20
FEATURE               Location/Qualifiers
misc_feature          1..20
                      note = Synthetic
source                1..20
                      mol_type = other DNA
                      organism = synthetic construct
SEQUENCE: 190
gcgctctttc tcgcgttccc                                          20

SEQ ID NO: 191        moltype = DNA  length = 20
FEATURE               Location/Qualifiers
misc_feature          1..20
                      note = Synthetic
source                1..20
                      mol_type = other DNA
                      organism = synthetic construct
SEQUENCE: 191
cgcgctcttt ctcgcgttcc                                          20

SEQ ID NO: 192        moltype = DNA  length = 20
FEATURE               Location/Qualifiers
misc_feature          1..20
                      note = Synthetic
source                1..20
                      mol_type = other DNA
                      organism = synthetic construct
SEQUENCE: 192
ctcgcgctct ttctcgcgtt                                          20

SEQ ID NO: 193        moltype = DNA  length = 20
```

```
FEATURE                Location/Qualifiers
misc_feature           1..20
                       note = Synthetic
source                 1..20
                       mol_type = other DNA
                       organism = synthetic construct
SEQUENCE: 193
gctcgcgctc tttctcgcgt                                              20

SEQ ID NO: 194         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 194
gcgctcgcgc tctttctcgc                                              20

SEQ ID NO: 195         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 195
cgcgctcgcg ctctttctcg                                              20

SEQ ID NO: 196         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 196
ctcgcgctcg cgctctttct                                              20

SEQ ID NO: 197         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 197
tctcgcgctc gcgctctttc                                              20

SEQ ID NO: 198         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 198
cttctcgcgc tcgcgctctt                                              20

SEQ ID NO: 199         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 199
ccttctcgcg ctcgcgctct                                              20

SEQ ID NO: 200         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 200
ctccttctcg cgctcgcgct                                              20
```

```
SEQ ID NO: 201          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 201
gctccttctc gcgctcgcgc                                              20

SEQ ID NO: 202          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 202
gcgctccttc tcgcgctcgc                                              20

SEQ ID NO: 203          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 203
cgcgctcctt ctcgcgctcg                                              20

SEQ ID NO: 204          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 204
gcactgtagc caccgcactg                                              20

SEQ ID NO: 205          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 205
ggcactgtag ccaccgcact                                              20

SEQ ID NO: 206          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 206
ggggcactgt agccaccgca                                              20

SEQ ID NO: 207          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 207
gggggcactg tagccaccgc                                              20

SEQ ID NO: 208          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 208
ggggggcact gtagccaccg                                              20
```

```
SEQ ID NO: 209          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 209
ccgggtccac tgcccccagg                                              20

SEQ ID NO: 210          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 210
tgctgcctct cagctgccag                                              20

SEQ ID NO: 211          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 211
tgcgtgctgc ctctcagctg                                              20

SEQ ID NO: 212          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 212
ctgctgacat cggggcagaa                                              20

SEQ ID NO: 213          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 213
ctgatgagct gctgacatcg                                              20

SEQ ID NO: 214          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 214
cagcgccaag cgctgcagct                                              20

SEQ ID NO: 215          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 215
tgctgttcca gcgccaagcg                                              20

SEQ ID NO: 216          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 216
```

```
gggcaggcag cggcacactg                                              20

SEQ ID NO: 217          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 217
acaccacatc gggccttggc                                              20

SEQ ID NO: 218          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 218
acctctgcac accacatcgg                                              20

SEQ ID NO: 219          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 219
gcaggggtgg cacacgatgc                                              20

SEQ ID NO: 220          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 220
ggcaggggtg gcacacgatg                                              20

SEQ ID NO: 221          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 221
ggggcagggg tggcacacga                                              20

SEQ ID NO: 222          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 222
gggcgcgcac acagggatcg                                              20

SEQ ID NO: 223          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 223
actcgggcct tcttggctgt                                              20

SEQ ID NO: 224          moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 224
tactcgggcc ttcttggctg                                        20

SEQ ID NO: 225          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 225
tctactcggg ccttcttggc                                        20

SEQ ID NO: 226          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 226
ctctactcgg gccttcttgg                                        20

SEQ ID NO: 227          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 227
tcctctactc gggccttctt                                        20

SEQ ID NO: 228          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 228
ttcctctact cgggccttct                                        20

SEQ ID NO: 229          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 229
gcttcctcta ctcgggcctt                                        20

SEQ ID NO: 230          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 230
ggcttcctct actcgggcct                                        20

SEQ ID NO: 231          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 231
ctaagaggcg gccataggga                                        20

SEQ ID NO: 232          moltype = DNA  length = 20
FEATURE                 Location/Qualifiers
misc_feature            1..20
                        note = Synthetic
source                  1..20
                        mol_type = other DNA
```

```
                       organism = synthetic construct
SEQUENCE: 232
gctaagaggc ggccataggg                                                20

SEQ ID NO: 233         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 233
tggctaagag gcggccatag                                                20

SEQ ID NO: 234         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 234
ttggctaaga ggcggccata                                                20

SEQ ID NO: 235         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 235
gtgaggtggg ggcaggtgtg                                                20

SEQ ID NO: 236         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 236
tgtgaggtgg gggcaggtgt                                                20

SEQ ID NO: 237         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 237
gctgtgaggt gggggcaggt                                                20

SEQ ID NO: 238         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 238
ggctgtgagg tgggggcagg                                                20

SEQ ID NO: 239         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 239
ctggctgtga ggtgggggca                                                20

SEQ ID NO: 240         moltype = DNA  length = 20
FEATURE                Location/Qualifiers
misc_feature           1..20
                       note = Synthetic
source                 1..20
```

```
                        mol_type = other DNA
                        organism = synthetic construct
SEQUENCE: 240
gaggaagcca cggtggcaat                                               20

SEQ ID NO: 241          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 241
cggcccgctt cttggccagc                                               20

SEQ ID NO: 242          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 242
tcggcccgct tcttggccag                                               20

SEQ ID NO: 243          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 243
gtcggcccgc ttcttggcca                                               20

SEQ ID NO: 244          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 244
ggtcggcccg cttcttggcc                                               20

SEQ ID NO: 245          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 245
aggtcggccc gcttcttggc                                               20

SEQ ID NO: 246          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 246
caggtcggcc cgcttcttgg                                               20

SEQ ID NO: 247          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 247
ccaggtcggc ccgcttcttg                                               20

SEQ ID NO: 248          moltype = DNA  length = 20
FEATURE                 Location/Qualifiers
misc_feature            1..20
                        note = Synthetic
```

```
source                  1..20
                        mol_type = other DNA
                        organism = synthetic construct
SEQUENCE: 248
accaggtcgg cccgcttctt                                                20

SEQ ID NO: 249          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 249
caccaggtcg gcccgcttct                                                20

SEQ ID NO: 250          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 250
ccaccaggtc ggcccgcttc                                                20

SEQ ID NO: 251          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 251
tccaccaggt cggcccgctt                                                20

SEQ ID NO: 252          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 252
ctccaccagg tcggcccgct                                                20

SEQ ID NO: 253          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 253
tctccaccag gtcggcccgc                                                20

SEQ ID NO: 254          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 254
ttctccacca ggtcggcccg                                                20

SEQ ID NO: 255          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 255
cttctccacc aggtcggccc                                                20

SEQ ID NO: 256          moltype = DNA  length = 20
FEATURE                 Location/Qualifiers
misc_feature            1..20
```

```
                         note = Synthetic
source                   1..20
                         mol_type = other DNA
                         organism = synthetic construct
SEQUENCE: 256
accttctcca ccaggtcggc                                              20

SEQ ID NO: 257           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 257
caccttctcc accaggtcgg                                              20

SEQ ID NO: 258           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 258
gcaccttctc caccaggtcg                                              20

SEQ ID NO: 259           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 259
ccgcaccttc tccaccaggt                                              20

SEQ ID NO: 260           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 260
gccgcacctt ctccaccagg                                              20

SEQ ID NO: 261           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 261
cgccgcacct tctccaccag                                              20

SEQ ID NO: 262           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 262
cgcgccgcac cttctccacc                                              20

SEQ ID NO: 263           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 263
tcgcgccgca ccttctccac                                              20

SEQ ID NO: 264           moltype = DNA  length = 20
FEATURE                  Location/Qualifiers
```

```
misc_feature          1..20
                      note = Synthetic
source                1..20
                      mol_type = other DNA
                      organism = synthetic construct
SEQUENCE: 264
ctcgcgccgc accttctcca                                              20

SEQ ID NO: 265        moltype = DNA  length = 20
FEATURE               Location/Qualifiers
misc_feature          1..20
                      note = Synthetic
source                1..20
                      mol_type = other DNA
                      organism = synthetic construct
SEQUENCE: 265
cctcgcgccg caccttctcc                                              20

SEQ ID NO: 266        moltype = DNA  length = 20
FEATURE               Location/Qualifiers
misc_feature          1..20
                      note = Synthetic
source                1..20
                      mol_type = other DNA
                      organism = synthetic construct
SEQUENCE: 266
gcctcgcgcc gcaccttctc                                              20

SEQ ID NO: 267        moltype = DNA  length = 20
FEATURE               Location/Qualifiers
misc_feature          1..20
                      note = Synthetic
source                1..20
                      mol_type = other DNA
                      organism = synthetic construct
SEQUENCE: 267
ggcctcgcgc cgcaccttct                                              20

SEQ ID NO: 268        moltype = DNA  length = 20
FEATURE               Location/Qualifiers
misc_feature          1..20
                      note = Synthetic
source                1..20
                      mol_type = other DNA
                      organism = synthetic construct
SEQUENCE: 268
cggcctcgcg ccgcaccttc                                              20

SEQ ID NO: 269        moltype = DNA  length = 20
FEATURE               Location/Qualifiers
misc_feature          1..20
                      note = Synthetic
source                1..20
                      mol_type = other DNA
                      organism = synthetic construct
SEQUENCE: 269
tcggcctcgc gccgcacctt                                              20

SEQ ID NO: 270        moltype = DNA  length = 20
FEATURE               Location/Qualifiers
misc_feature          1..20
                      note = Synthetic
source                1..20
                      mol_type = other DNA
                      organism = synthetic construct
SEQUENCE: 270
ctcggcctcg cgccgcacct                                              20

SEQ ID NO: 271        moltype = DNA  length = 20
FEATURE               Location/Qualifiers
misc_feature          1..20
                      note = Synthetic
source                1..20
                      mol_type = other DNA
                      organism = synthetic construct
SEQUENCE: 271
gctcggcctc gcgccgcacc                                              20

SEQ ID NO: 272        moltype = DNA  length = 20
```

```
FEATURE                 Location/Qualifiers
misc_feature            1..20
                        note = Synthetic
source                  1..20
                        mol_type = other DNA
                        organism = synthetic construct
SEQUENCE: 272
tgctcggcct cgcgccgcac                                              20

SEQ ID NO: 273          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 273
gcgctccttt tcttcgcgcg                                              20

SEQ ID NO: 274          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 274
cgcgctcctt ttcttcgcgc                                              20

SEQ ID NO: 275          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 275
tcgcgctcct tttcttcgcg                                              20

SEQ ID NO: 276          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 276
ctcgcgctcc ttttcttcgc                                              20

SEQ ID NO: 277          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 277
gctcgcgctc cttttcttcg                                              20

SEQ ID NO: 278          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 278
cgctcgcgct ccttttcttc                                              20

SEQ ID NO: 279          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 279
gcgctcgcgc tccttttctt                                              20
```

```
SEQ ID NO: 280          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 280
cgcgctcgcg ctccttttct                                             20

SEQ ID NO: 281          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 281
tcgcgctcgc gctccttttc                                             20

SEQ ID NO: 282          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 282
ctcgcgctcg cgctcctttt                                             20

SEQ ID NO: 283          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 283
gctcgcgctc gcgctccttt                                             20

SEQ ID NO: 284          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 284
cgctcgcgct cgcgctcctt                                             20

SEQ ID NO: 285          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 285
ccgctcgcgc tcgcgctcct                                             20

SEQ ID NO: 286          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 286
cccgctcgcg ctcgcgctcc                                             20

SEQ ID NO: 287          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 287
tcccgctcgc gctcgcgctc                                             20
```

```
SEQ ID NO: 288          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 288
ttcccgctcg cgctcgcgct                                              20

SEQ ID NO: 289          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 289
gttcccgctc gcgctcgcgc                                              20

SEQ ID NO: 290          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 290
cgttcccgct cgcgctcgcg                                              20

SEQ ID NO: 291          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 291
gcgttcccgc tcgcgctcgc                                              20

SEQ ID NO: 292          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 292
cgcgttcccg ctcgcgctcg                                              20

SEQ ID NO: 293          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 293
tcgcgttccc gctcgcgctc                                              20

SEQ ID NO: 294          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 294
ctcgcgttcc cgctcgcgct                                              20

SEQ ID NO: 295          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 295
```

```
tctcgcgttc ccgctcgcgc                                              20

SEQ ID NO: 296          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 296
ttctcgcgtt cccgctcgcg                                              20

SEQ ID NO: 297          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 297
tttctcgcgt tcccgctcgc                                              20

SEQ ID NO: 298          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 298
ctttctcgcg ttcccgctcg                                              20

SEQ ID NO: 299          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 299
ctcgcgctcc ttctcgcgct                                              20

SEQ ID NO: 300          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 300
gctcgcgctc cttctcgcgc                                              20

SEQ ID NO: 301          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 301
aagctcgcgc tccttctcgc                                              20

SEQ ID NO: 302          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 302
caagctcgcg ctccttctcg                                              20

SEQ ID NO: 303          moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 303
ttcaagctcg cgctccttct                                            20

SEQ ID NO: 304          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 304
gttcaagctc gcgctccttc                                            20

SEQ ID NO: 305          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 305
cgttcaagct cgcgctcctt                                            20

SEQ ID NO: 306          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 306
gcgttcaagc tcgcgctcct                                            20

SEQ ID NO: 307          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 307
ccgcactgcc cggttcaaat                                            20

SEQ ID NO: 308          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 308
accgcactgc ccggttcaaa                                            20

SEQ ID NO: 309          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 309
ccaccgcact gcccggttca                                            20

SEQ ID NO: 310          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 310
gccaccgcac tgcccggttc                                            20

SEQ ID NO: 311          moltype = DNA  length = 20
FEATURE                 Location/Qualifiers
misc_feature            1..20
                        note = Synthetic
source                  1..20
                        mol_type = other DNA
```

```
                        organism = synthetic construct
SEQUENCE: 311
tagccaccgc actgcccggt                                          20

SEQ ID NO: 312          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 312
gtagccaccg cactgcccgg                                          20

SEQ ID NO: 313          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 313
ctgtagccac cgcactgccc                                          20

SEQ ID NO: 314          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 314
actgtagcca ccgcactgcc                                          20

SEQ ID NO: 315          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 315
cccgggtcca ctgcccccag                                          20

SEQ ID NO: 316          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 316
gtgctgcctc tcagctgcca                                          20

SEQ ID NO: 317          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 317
cgtgctgcct ctcagctgcc                                          20

SEQ ID NO: 318          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 318
gcgtgctgcc tctcagctgc                                          20

SEQ ID NO: 319          moltype = DNA  length = 20
FEATURE                 Location/Qualifiers
misc_feature            1..20
                        note = Synthetic
source                  1..20
```

```
                          mol_type = other DNA
                          organism = synthetic construct
SEQUENCE: 319
ctgcgtgctg cctctcagct                                                20

SEQ ID NO: 320            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 320
tctgcgtgct gcctctcagc                                                20

SEQ ID NO: 321            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 321
ttctgcgtgc tgcctctcag                                                20

SEQ ID NO: 322            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 322
tttctgcgtg ctgcctctca                                                20

SEQ ID NO: 323            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 323
ctttctgcgt gctgcctctc                                                20

SEQ ID NO: 324            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 324
cctttctgcg tgctgcctct                                                20

SEQ ID NO: 325            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 325
ccctttctgc gtgctgcctc                                                20

SEQ ID NO: 326            moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 326
accctttctg cgtgctgcct                                                20

SEQ ID NO: 327            moltype = DNA  length = 20
FEATURE                   Location/Qualifiers
misc_feature              1..20
                          note = Synthetic
```

```
source                  1..20
                        mol_type = other DNA
                        organism = synthetic construct
SEQUENCE: 327
caccctttct gcgtgctgcc                                              20

SEQ ID NO: 328          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 328
ccaccctttc tgcgtgctgc                                              20

SEQ ID NO: 329          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 329
gccacccttt ctgcgtgctg                                              20

SEQ ID NO: 330          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 330
cgccaccctt tctgcgtgct                                              20

SEQ ID NO: 331          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 331
ccgccaccct ttctgcgtgc                                              20

SEQ ID NO: 332          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 332
gccgccaccc tttctgcgtg                                              20

SEQ ID NO: 333          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 333
ggccgccacc ctttctgcgt                                              20

SEQ ID NO: 334          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 334
gggccgccac cctttctgcg                                              20

SEQ ID NO: 335          moltype = DNA  length = 20
FEATURE                 Location/Qualifiers
misc_feature            1..20
```

```
                        note = Synthetic
source                  1..20
                        mol_type = other DNA
                        organism = synthetic construct
SEQUENCE: 335
agggccgcca ccctttctgc                                              20

SEQ ID NO: 336          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 336
cagggccgcc accctttctg                                              20

SEQ ID NO: 337          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 337
ggcagaaagg gaggccggca                                              20

SEQ ID NO: 338          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 338
gggcagaaag ggaggccggc                                              20

SEQ ID NO: 339          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 339
ggggcagaaa gggaggccgg                                              20

SEQ ID NO: 340          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 340
cggggcagaa agggaggccg                                              20

SEQ ID NO: 341          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 341
tcggggcaga aagggaggcc                                              20

SEQ ID NO: 342          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 342
atcggggcag aaagggaggc                                              20

SEQ ID NO: 343          moltype = DNA  length = 20
FEATURE                 Location/Qualifiers
```

```
misc_feature          1..20
                      note = Synthetic
source                1..20
                      mol_type = other DNA
                      organism = synthetic construct
SEQUENCE: 343
catcggggca gaaagggagg                                          20

SEQ ID NO: 344        moltype = DNA  length = 20
FEATURE               Location/Qualifiers
misc_feature          1..20
                      note = Synthetic
source                1..20
                      mol_type = other DNA
                      organism = synthetic construct
SEQUENCE: 344
acatcggggc agaaagggag                                          20

SEQ ID NO: 345        moltype = DNA  length = 20
FEATURE               Location/Qualifiers
misc_feature          1..20
                      note = Synthetic
source                1..20
                      mol_type = other DNA
                      organism = synthetic construct
SEQUENCE: 345
gacatcgggg cagaaaggga                                          20

SEQ ID NO: 346        moltype = DNA  length = 20
FEATURE               Location/Qualifiers
misc_feature          1..20
                      note = Synthetic
source                1..20
                      mol_type = other DNA
                      organism = synthetic construct
SEQUENCE: 346
tgacatcggg gcagaaaggg                                          20

SEQ ID NO: 347        moltype = DNA  length = 20
FEATURE               Location/Qualifiers
misc_feature          1..20
                      note = Synthetic
source                1..20
                      mol_type = other DNA
                      organism = synthetic construct
SEQUENCE: 347
ctgacatcgg ggcagaaagg                                          20

SEQ ID NO: 348        moltype = DNA  length = 20
FEATURE               Location/Qualifiers
misc_feature          1..20
                      note = Synthetic
source                1..20
                      mol_type = other DNA
                      organism = synthetic construct
SEQUENCE: 348
gctgacatcg gggcagaaag                                          20

SEQ ID NO: 349        moltype = DNA  length = 20
FEATURE               Location/Qualifiers
misc_feature          1..20
                      note = Synthetic
source                1..20
                      mol_type = other DNA
                      organism = synthetic construct
SEQUENCE: 349
tgctgacatc ggggcagaaa                                          20

SEQ ID NO: 350        moltype = DNA  length = 20
FEATURE               Location/Qualifiers
misc_feature          1..20
                      note = Synthetic
source                1..20
                      mol_type = other DNA
                      organism = synthetic construct
SEQUENCE: 350
gctgctgaca tcggggcaga                                          20

SEQ ID NO: 351        moltype = DNA  length = 20
```

```
FEATURE               Location/Qualifiers
misc_feature          1..20
                      note = Synthetic
source                1..20
                      mol_type = other DNA
                      organism = synthetic construct
SEQUENCE: 351
agctgctgac atcggggcag                                              20

SEQ ID NO: 352        moltype = DNA  length = 20
FEATURE               Location/Qualifiers
misc_feature          1..20
                      note = Synthetic
source                1..20
                      mol_type = other DNA
                      organism = synthetic construct
SEQUENCE: 352
gagctgctga catcggggca                                              20

SEQ ID NO: 353        moltype = DNA  length = 20
FEATURE               Location/Qualifiers
misc_feature          1..20
                      note = Synthetic
source                1..20
                      mol_type = other DNA
                      organism = synthetic construct
SEQUENCE: 353
atgagctgct gacatcgggg                                              20

SEQ ID NO: 354        moltype = DNA  length = 20
FEATURE               Location/Qualifiers
misc_feature          1..20
                      note = Synthetic
source                1..20
                      mol_type = other DNA
                      organism = synthetic construct
SEQUENCE: 354
gatgagctgc tgacatcggg                                              20

SEQ ID NO: 355        moltype = DNA  length = 20
FEATURE               Location/Qualifiers
misc_feature          1..20
                      note = Synthetic
source                1..20
                      mol_type = other DNA
                      organism = synthetic construct
SEQUENCE: 355
tgatgagctg ctgacatcgg                                              20

SEQ ID NO: 356        moltype = DNA  length = 20
FEATURE               Location/Qualifiers
misc_feature          1..20
                      note = Synthetic
source                1..20
                      mol_type = other DNA
                      organism = synthetic construct
SEQUENCE: 356
gctgatgagc tgctgacatc                                              20

SEQ ID NO: 357        moltype = DNA  length = 20
FEATURE               Location/Qualifiers
misc_feature          1..20
                      note = Synthetic
source                1..20
                      mol_type = other DNA
                      organism = synthetic construct
SEQUENCE: 357
agctgatgag ctgctgacat                                              20

SEQ ID NO: 358        moltype = DNA  length = 20
FEATURE               Location/Qualifiers
misc_feature          1..20
                      note = Synthetic
source                1..20
                      mol_type = other DNA
                      organism = synthetic construct
SEQUENCE: 358
cagctgatga gctgctgaca                                              20
```

```
SEQ ID NO: 359          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 359
gcagctgatg agctgctgac                                              20

SEQ ID NO: 360          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 360
tgcagctgat gagctgctga                                              20

SEQ ID NO: 361          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 361
ctgcagctga tgagctgctg                                              20

SEQ ID NO: 362          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 362
cctgcagctg atgagctgct                                              20

SEQ ID NO: 363          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 363
gcctgcagct gatgagctgc                                              20

SEQ ID NO: 364          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 364
ggcctgcagc tgatgagctg                                              20

SEQ ID NO: 365          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 365
tggcctgcag ctgatgagct                                              20

SEQ ID NO: 366          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 366
atggcctgca gctgatgagc                                              20
```

```
SEQ ID NO: 367          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 367
catggcctgc agctgatgag                                              20

SEQ ID NO: 368          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 368
gcatggcctg cagctgatga                                              20

SEQ ID NO: 369          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 369
tgcatggcct gcagctgatg                                              20

SEQ ID NO: 370          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 370
cagctcagct gactgtgcgt                                              20

SEQ ID NO: 371          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 371
gcagctcagc tgactgtgcg                                              20

SEQ ID NO: 372          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 372
tgcagctcag ctgactgtgc                                              20

SEQ ID NO: 373          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 373
ctgcagctca gctgactgtg                                              20

SEQ ID NO: 374          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 374
```

```
gctgcagctc agctgactgt                                                20

SEQ ID NO: 375          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 375
cgctgcagct cagctgactg                                                20

SEQ ID NO: 376          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 376
gcgctgcagc tcagctgact                                                20

SEQ ID NO: 377          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 377
agcgctgcag ctcagctgac                                                20

SEQ ID NO: 378          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 378
aagcgctgca gctcagctga                                                20

SEQ ID NO: 379          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 379
caagcgctgc agctcagctg                                                20

SEQ ID NO: 380          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 380
ccaagcgctg cagctcagct                                                20

SEQ ID NO: 381          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 381
gccaagcgct gcagctcagc                                                20

SEQ ID NO: 382          moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 382
cgccaagcgc tgcagctcag                                              20

SEQ ID NO: 383          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 383
gcgccaagcg ctgcagctca                                              20

SEQ ID NO: 384          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 384
agcgccaagc gctgcagctc                                              20

SEQ ID NO: 385          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 385
ccagcgccaa gcgctgcagc                                              20

SEQ ID NO: 386          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 386
tccagcgcca agcgctgcag                                              20

SEQ ID NO: 387          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 387
ttccagcgcc aagcgctgca                                              20

SEQ ID NO: 388          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 388
tgttccagcg ccaagcgctg                                              20

SEQ ID NO: 389          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 389
ctgttccagc gccaagcgct                                              20

SEQ ID NO: 390          moltype = DNA  length = 20
FEATURE                 Location/Qualifiers
misc_feature            1..20
                        note = Synthetic
source                  1..20
                        mol_type = other DNA
```

```
                        organism = synthetic construct
SEQUENCE: 390
gctgttccag cgccaagcgc                                                 20

SEQ ID NO: 391          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 391
ctgctgttcc agcgccaagc                                                 20

SEQ ID NO: 392          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 392
gctgctgttc cagcgccaag                                                 20

SEQ ID NO: 393          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 393
tgctgctgtt ccagcgccaa                                                 20

SEQ ID NO: 394          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 394
ctgctgctgt tccagcgcca                                                 20

SEQ ID NO: 395          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 395
actgctgctg ttccagcgcc                                                 20

SEQ ID NO: 396          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 396
cactgctgct gttccagcgc                                                 20

SEQ ID NO: 397          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 397
ccactgctgc tgttccagcg                                                 20

SEQ ID NO: 398          moltype = DNA  length = 20
FEATURE                 Location/Qualifiers
misc_feature            1..20
                        note = Synthetic
source                  1..20
```

```
                         mol_type = other DNA
                         organism = synthetic construct
SEQUENCE: 398
gccactgctg ctgttccagc                                                   20

SEQ ID NO: 399           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 399
agccactgct gctgttccag                                                   20

SEQ ID NO: 400           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 400
cagccactgc tgctgttcca                                                   20

SEQ ID NO: 401           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 401
gcagccactg ctgctgttcc                                                   20

SEQ ID NO: 402           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 402
tgcagccact gctgctgttc                                                   20

SEQ ID NO: 403           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 403
atgcagccac tgctgctgtt                                                   20

SEQ ID NO: 404           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 404
ggcagcggca cactgtgcag                                                   20

SEQ ID NO: 405           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 405
aggcagcggc acactgtgca                                                   20

SEQ ID NO: 406           moltype = DNA  length = 20
FEATURE                  Location/Qualifiers
misc_feature             1..20
                         note = Synthetic
```

```
source                  1..20
                        mol_type = other DNA
                        organism = synthetic construct
SEQUENCE: 406
caggcagcgg cacactgtgc                                              20

SEQ ID NO: 407          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 407
gcaggcagcg gcacactgtg                                              20

SEQ ID NO: 408          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 408
ggcaggcagc ggcacactgt                                              20

SEQ ID NO: 409          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 409
ttggccttct gtctgtccct                                              20

SEQ ID NO: 410          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 410
cttggccttc tgtctgtccc                                              20

SEQ ID NO: 411          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 411
ccttggcctt ctgtctgtcc                                              20

SEQ ID NO: 412          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 412
gccttggcct tctgtctgtc                                              20

SEQ ID NO: 413          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 413
ggccttggcc ttctgtctgt                                              20

SEQ ID NO: 414          moltype = DNA  length = 20
FEATURE                 Location/Qualifiers
misc_feature            1..20
```

```
                        note = Synthetic
source                  1..20
                        mol_type = other DNA
                        organism = synthetic construct
SEQUENCE: 414
gggccttggc cttctgtctg                                            20

SEQ ID NO: 415          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 415
cgggccttgg ccttctgtct                                            20

SEQ ID NO: 416          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 416
tcgggccttg gccttctgtc                                            20

SEQ ID NO: 417          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 417
atcgggcctt ggccttctgt                                            20

SEQ ID NO: 418          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 418
catcgggcct tggccttctg                                            20

SEQ ID NO: 419          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 419
acatcgggcc ttggccttct                                            20

SEQ ID NO: 420          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 420
cacatcgggc cttggccttc                                            20

SEQ ID NO: 421          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 421
ccacatcggg ccttggcctt                                            20

SEQ ID NO: 422          moltype = DNA  length = 20
FEATURE                 Location/Qualifiers
```

```
misc_feature          1..20
                      note = Synthetic
source                1..20
                      mol_type = other DNA
                      organism = synthetic construct
SEQUENCE: 422
accacatcgg gccttggcct                                              20

SEQ ID NO: 423        moltype = DNA  length = 20
FEATURE               Location/Qualifiers
misc_feature          1..20
                      note = Synthetic
source                1..20
                      mol_type = other DNA
                      organism = synthetic construct
SEQUENCE: 423
caccacatcg ggccttggcc                                              20

SEQ ID NO: 424        moltype = DNA  length = 20
FEATURE               Location/Qualifiers
misc_feature          1..20
                      note = Synthetic
source                1..20
                      mol_type = other DNA
                      organism = synthetic construct
SEQUENCE: 424
cacaccacat cgggccttgg                                              20

SEQ ID NO: 425        moltype = DNA  length = 20
FEATURE               Location/Qualifiers
misc_feature          1..20
                      note = Synthetic
source                1..20
                      mol_type = other DNA
                      organism = synthetic construct
SEQUENCE: 425
gcacaccaca tcgggccttg                                              20

SEQ ID NO: 426        moltype = DNA  length = 20
FEATURE               Location/Qualifiers
misc_feature          1..20
                      note = Synthetic
source                1..20
                      mol_type = other DNA
                      organism = synthetic construct
SEQUENCE: 426
tgcacaccac atcgggcctt                                              20

SEQ ID NO: 427        moltype = DNA  length = 20
FEATURE               Location/Qualifiers
misc_feature          1..20
                      note = Synthetic
source                1..20
                      mol_type = other DNA
                      organism = synthetic construct
SEQUENCE: 427
tctgcacacc acatcgggcc                                              20

SEQ ID NO: 428        moltype = DNA  length = 20
FEATURE               Location/Qualifiers
misc_feature          1..20
                      note = Synthetic
source                1..20
                      mol_type = other DNA
                      organism = synthetic construct
SEQUENCE: 428
ctctgcacac cacatcgggc                                              20

SEQ ID NO: 429        moltype = DNA  length = 20
FEATURE               Location/Qualifiers
misc_feature          1..20
                      note = Synthetic
source                1..20
                      mol_type = other DNA
                      organism = synthetic construct
SEQUENCE: 429
cctctgcaca ccacatcggg                                              20

SEQ ID NO: 430        moltype = DNA  length = 20
```

```
FEATURE                Location/Qualifiers
misc_feature           1..20
                       note = Synthetic
source                 1..20
                       mol_type = other DNA
                       organism = synthetic construct
SEQUENCE: 430
cacctctgca caccacatcg                                        20

SEQ ID NO: 431         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 431
ccacctctgc acaccacatc                                        20

SEQ ID NO: 432         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 432
cccacctctg cacaccacat                                        20

SEQ ID NO: 433         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 433
ccccacctct gcacaccaca                                        20

SEQ ID NO: 434         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 434
tccccacctc tgcacaccac                                        20

SEQ ID NO: 435         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 435
ctccccacct ctgcacacca                                        20

SEQ ID NO: 436         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 436
cctccccacc tctgcacacc                                        20

SEQ ID NO: 437         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 437
acctccccac ctctgcacac                                        20
```

```
SEQ ID NO: 438          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 438
cacctcccca cctctgcaca                                              20

SEQ ID NO: 439          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 439
ccacctcccc acctctgcac                                              20

SEQ ID NO: 440          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 440
aggggcaggg gtggcacacg                                              20

SEQ ID NO: 441          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 441
gaggggcagg ggtggcacac                                              20

SEQ ID NO: 442          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 442
ggaggggcag gggtggcaca                                              20

SEQ ID NO: 443          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 443
gggaggggca ggggtggcac                                              20

SEQ ID NO: 444          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 444
ggggaggggc aggggtggca                                              20

SEQ ID NO: 445          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 445
cggggagggg caggggtggc                                              20
```

```
SEQ ID NO: 446          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 446
tcggggaggg gcaggggtgg                                              20

SEQ ID NO: 447          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 447
atcggggagg ggcaggggtg                                              20

SEQ ID NO: 448          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 448
gatcggggag gggcaggggt                                              20

SEQ ID NO: 449          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 449
ggatcgggga ggggcagggg                                              20

SEQ ID NO: 450          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 450
gggatcgggg aggggcaggg                                              20

SEQ ID NO: 451          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 451
agggatcggg gaggggcagg                                              20

SEQ ID NO: 452          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 452
cagggatcgg ggaggggcag                                              20

SEQ ID NO: 453          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 453
```

```
acagggatcg gggaggggca                                              20

SEQ ID NO: 454          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 454
cacagggatc ggggaggggc                                              20

SEQ ID NO: 455          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 455
acacagggat cggggagggg                                              20

SEQ ID NO: 456          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 456
cacacaggga tcggggaggg                                              20

SEQ ID NO: 457          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 457
gcacacaggg atcggggagg                                              20

SEQ ID NO: 458          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 458
cgcacacagg gatcggggag                                              20

SEQ ID NO: 459          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 459
gcgcacacag ggatcgggga                                              20

SEQ ID NO: 460          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 460
cgcgcacaca gggatcgggg                                              20

SEQ ID NO: 461          moltype = DNA  length = 20
FEATURE                 Location/Qualifiers
misc_feature            1..20
                        note = Synthetic
source                  1..20
                        mol_type = other DNA
                        organism = synthetic construct
```

```
SEQUENCE: 461
gcgcgcacac agggatcggg                                         20

SEQ ID NO: 462          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 462
ggcgcgcaca cagggatcgg                                         20

SEQ ID NO: 463          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 463
ggggcgcgca cacagggatc                                         20

SEQ ID NO: 464          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 464
gggggcgcgc acacagggat                                         20

SEQ ID NO: 465          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 465
tcaacaagca gggtcggagt                                         20

SEQ ID NO: 466          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 466
ttgaacgcag cgtgaagttg                                         20

SEQ ID NO: 467          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 467
cttcggttgt cctggtcgat a                                       21

SEQ ID NO: 468          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 468
ttgcgattgc caggagacat                                         20

SEQ ID NO: 469          moltype = DNA  length = 22
FEATURE                 Location/Qualifiers
misc_feature            1..22
                        note = Synthetic
source                  1..22
                        mol_type = other DNA
```

```
                         organism = synthetic construct
SEQUENCE: 469
gaagatcaag atcattgctc ct                                          22

SEQ ID NO: 470           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 470
tactcctgct tgctgatcca                                             20

SEQ ID NO: 471           moltype = DNA  length = 4355
FEATURE                  Location/Qualifiers
source                   1..4355
                         mol_type = genomic DNA
                         organism = Homo sapiens
SEQUENCE: 471
gcaggacgcc atactggacg ccaagtggga ggaacttcaa ggctgtcccc tgcgggcctc  60
ccgctctgct tctgcgaagg tttcattgaa aacagatcct gcaaaagttc caggtgccca  120
cactggaaac ttggagatcc tgcttcccag accacagctg tggggaactt ggggtggagc  180
agagaagttt ctgtattcag ctgcccaggc agaggagaat ggggtctcca cagcctgaag  240
aatgaagaca cgacagaata aagactcgat gtcaatgagg agtggacgga agaaagaggc  300
ccctgggccc cgggaagaac tgagatcgag gggccgggcc tcccctggag gggtcagcac  360
gtccagcagt gatggcaaag ctgagaagtc caggcagaca gccaagaagg cccgagtaga  420
ggaagcctcc accccaaagg tcaacaagca gggtcggagt gaggagatct cagagagtga  480
aagtgaggag accaatgcac caaaaaagac caaaactgag caggaactcc ctcggccaca  540
gtctccctcc gatctggata gcttggacgg gcggagcctt aatgatgatg gcagcagcga  600
ccctagggat atcgaccagg acaaccgaag cacgtccccc agtatctaca gccctggaag  660
tgtggagaat gactctgact catcttctgg cctgtcccag ggcccagccc gcccctacca  720
cccacctcca ctctttcctc cttcccctca accgccagac agcacccctc gacagccaga  780
ggctagcttt gaaccccatc cttctgtgac acccactgga tatcatgctc ccatggagcc  840
ccccacatct cgaatgttcc aggctcctcc tggggcccct ccccctcacc cacagctcta  900
tcctgggggc actggtggag ttttgtctgg acccccaatg ggtcccaagg ggggaggggc  960
tgcctcatca gtggggggcc ctaatggggg taagcagcac cccccaccca ctactcccat  1020
ttcagtatca agctctgggg ctagtggtgc tcccccaaca aagccgccta ccactccagt  1080
gggtggtggg aacctacctt ctgctccacc accagccaac ttcccccatg tgacaccgaa  1140
cctgcctccc ccacctgccc tgagacccct caacaatgca tcagcctctc cccctggcct  1200
gggggcccaa ccactacctg gtcatctgcc ctctccccac gccatgggac agggtatggg  1260
tggacttcct cctggcccag agaagggccc aactctggct ccttcacccc actctctgcc  1320
tcctgcttcc tcttctgctc cagcgccccc catgaggttt ccttattcat cctctagtag  1380
tagctctgca gcagcctcct cttccagttc ttcctcctct tcctctgcct ccccccttccc  1440
agcttcccag gcattgccca gctacccccca ctctttccct ccccccaacaa gcctctctgt  1500
ctccaatcag ccccccaagt atactcagcc ttctctccca tcccaggctg tgtggagcca  1560
gggtccccca ccacctcctc cctatggccg cctcttagcc aacagcaatg cccatccagg  1620
ccccttccct ccctctactg gggcccagtc caccgcccac ccaccagtct caacacatca  1680
ccatcaccac cagcaacagc aacagcagca gcagcagcag cagcagcagc agcagcagca  1740
gcagcagcat cacggaaact ctgggccccc tcctcctgga gcatttcccc acccactgga  1800
gggcggtagc tcccaccacg cacaccctta cgccatgtct ccctccctgg ggtctctgag  1860
gccctaccca ccagggccag cacacctgcc cccacctcac agccaggtgt cctacagcca  1920
agcaggcccc aatggccctc cagtctcttc ctcttccaac tcttcctctt ccacttctca  1980
agggtcctac ccatgttcac acccctcccc ttcccagggc cctcaagggg cgccctaccc  2040
tttcccaccg gtgcctacgg tcaccacctc ttcggctacc ctttccacgg tcattgccac  2100
cgtggcttcc tcgccagcag gctacaaaac ggcctcccca cctgggcccc caccgtacgg  2160
aaagagagcc ccgtccccgg gggcctacaa gacagccacc ccacccggat acaaacccgg  2220
gtcgcctccc tccttccgaa cggggacccc accgggctat cgaggaacct cgccacctgc  2280
aggcccaggg accttcaagc cgggctcgcc caccgtggga cctgggcccc tgccacctgc  2340
ggggccctca ggcctgccat cgctgccacc accacctgcg gcccctgcct cagggccgcc  2400
cctgagcgcc acgcagatca aacaggagcc ggctgaggag tatgagaccc ccgagagccc  2460
ggtgccccca gcccgcagcc cctcgccccc tcccaaggtg gtagatgtac ccagccatgc  2520
cagtcagtct gccaggttca acaaacacct ggatcgcggc ttcaactcgt gcgcgcgcag  2580
cgacctgtac ttcgtgccac tggagggctc caagctggcc aagaagcggg ccgacctggt  2640
ggagaaggtg cggcgcgagg ccgagcagcg cgcgcgcgaa gaaaaggagc gcgagcgcga  2700
gcgggaacgc gagaaagagc gcgagcgcga gaaggagcgc gagcttgaac gcagcgtgaa  2760
gttggctcag gagggccgtg ctccggtgga atgcccatct ctgggcccag tgccccatcg  2820
ccctccattt gaaccgggca gtgcggtggc tacagtgccc ccctacctgg gtcctgacac  2880
tccagccttg cgcactctca gtgaatatgc ccggcctcat gtcatgtctc ctggcaatcg  2940
caaccatcca ttctacgtgc ccctgggggc agtggacccg gggctcctgg gttacaatgt  3000
cccggccctg tacagcagtg atccagctgc ccgggagagg gaacgggaag cccgtgaacg  3060
agacctccgt gaccgcctca agcctggctt tgaggtgaag cctagtgagc tggaacccct  3120
acatggggtc cctgggccgg gcttggatcc ctttccccga catggggggcc tggctctgca  3180
gcctggccca cctggcctgc accctttccc ctttcatccg agcctggggc ccctggagcg  3240
agaacgtcta gcgctggcag ctgggccagc cctgcggcct gacatgtcct atgctgagcg  3300
gctggcagct gagaggcagc acgcagaaag ggtggcggcc ctgggcaatg acccactggc  3360
ccggctgcag atgctcaatg tgactcccca tcaccaccag cactcccaca tccactcgca  3420
cctgcacctg caccagcaag atgctatcca tgcagcctct gcctcggtgc accctctcat  3480
tgacccccctg gcctcagggt ctcaccttac ccggatcccc tacccagctg gaactctccc  3540
```

-continued

```
taacccctg cttcctcacc ctctgcacga gaacgaagtt cttcgtcacc agctctttgc  3600
tgccccttac cgggacctgc cggcctccct ttctgccccg atgtcagcag ctcatcagct  3660
gcaggccatg cacgcacagt cagctgagct gcagcgcttg gcgctggaac agcagcagtg  3720
gctgcatgcc catcacccgc tgcacagtgt gccgctgcct gcccaggagg actactacag  3780
tcacctgaag aaggaaagcg acaagccact gtagaacctg cgatcaagag agcaccatgg  3840
ctcctacatt ggaccttgga gcacccccac cctcccccca ccgtgccctt ggcctgccac  3900
ccagagccaa gagggtgctg ctcagttgca gggcctccgc agctggacag agagtggggg  3960
agggagggac agacagaagg ccaaggcccg atgtggtgtg cagaggtggg gaggtggcga  4020
ggatggggac agaaagcgca cagaatcttg gaccaggtct ctcttccttg tccccccctgc  4080
ttttctcctc ccccatgccc aacccctgtg gccgccgccc ctcccctgcc ccgttggtgt  4140
gattatttca tctgttagat gtggctgttt tgcgtagcat cgtgtgccac ccctgcccct  4200
ccccgatccc tgtgtgcgcg ccccctctgc aatgtatgcc ccttgcccct tccccacact  4260
aataatttat atatataaat atctatatga cgctcttaaa aaaacatccc aaccaaaacc  4320
aaccaaacaa aaacatcctc acaactcccc aggaa                             4355

SEQ ID NO: 472          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 472
agagacctgg tccaagattc                                              20

SEQ ID NO: 473          moltype = DNA  length = 20
FEATURE                 Location/Qualifiers
source                  1..20
                        mol_type = other DNA
                        organism = synthetic construct
SEQUENCE: 473
ctcgcgctcg cgctccttct                                              20
```